(12) United States Patent
Gephart et al.

(10) Patent No.: US 8,506,601 B2
(45) Date of Patent: Aug. 13, 2013

(54) LOW PROFILE DUAL LOCKING FIXATION SYSTEM AND OFFSET ANCHOR MEMBER

(75) Inventors: Matthew P. Gephart, Marquette, MI (US); Troy D. Knapp, Butler, IN (US); Phillip J. Berman, Negaunee, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 565 days.

(21) Appl. No.: 12/579,345

(22) Filed: Oct. 14, 2009

(65) Prior Publication Data

US 2010/0160977 A1 Jun. 24, 2010

Related U.S. Application Data

(60) Provisional application No. 61/105,047, filed on Oct. 14, 2008, provisional application No. 61/105,048, filed on Oct. 14, 2008.

(51) Int. Cl.
*A61B 17/70* (2006.01)

(52) U.S. Cl.
USPC ............................................ 606/266; 606/305

(58) Field of Classification Search
USPC ................................................. 606/250–279
See application file for complete search history.

(56) References Cited

U.S. PATENT DOCUMENTS

| | | |
|---|---|---|
| 4,805,602 A | 2/1989 | Puno et al. |
| 4,946,458 A | 8/1990 | Harms et al. |
| 4,950,269 A | 8/1990 | Gaines, Jr. |
| 5,042,982 A | 8/1991 | Harms et al. |
| 5,120,171 A | 6/1992 | Lasner |
| 5,176,680 A | 1/1993 | Vignaud et al. |
| 5,207,678 A | 5/1993 | Harms et al. |
| 5,226,766 A | 7/1993 | Lasner |
| 5,257,993 A | 11/1993 | Asher et al. |
| 5,261,913 A | 11/1993 | Marnay |
| 5,306,275 A | 4/1994 | Bryan |
| 5,346,493 A | 9/1994 | Stahurski et al. |
| 5,360,431 A | 11/1994 | Puno et al. |
| 5,368,594 A | 11/1994 | Martin et al. |
| 5,385,583 A | 1/1995 | Cotrel |
| 5,443,467 A | 8/1995 | Biedermann et al. |
| 5,492,442 A | 2/1996 | Lasner |
| 5,520,690 A | 5/1996 | Errico et al. |
| 5,545,228 A | 8/1996 | Kambin |
| 5,549,608 A | 8/1996 | Errico et al. |

(Continued)

FOREIGN PATENT DOCUMENTS

| | | |
|---|---|---|
| DE | 10005386 | 8/2001 |
| EP | 0947174 A2 | 6/1999 |

(Continued)

*Primary Examiner* — Mary Hoffman
(74) *Attorney, Agent, or Firm* — Fitch, Even, Tabin & Flannery LLP

(57) ABSTRACT

A coupling device for securing an elongate member to the spine is provided. The coupling device comprises a compressible inner member that secures an anchor member therein when the inner member is axially shifted within an outer member. The elongate member is retained within the device by an axially inserted locking member, and may be secured independently of the anchor member. The coupling device and anchor may be configured to provide increased angulation of the anchor with respect to the coupling device. For instance, anchor member may have an offset head portion in order to provide normal pivoting of the coupling device when the anchor is attached to bone at an angle.

4 Claims, 70 Drawing Sheets

(56) References Cited

U.S. PATENT DOCUMENTS

| | | |
|---|---|---|
| 5,586,984 A | 12/1996 | Errico et al. |
| 5,628,740 A | 5/1997 | Mullane |
| 5,630,817 A | 5/1997 | Rokegem et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,392 A | 11/1997 | Richelsoph et al. |
| 5,690,630 A | 11/1997 | Errico et al. |
| 5,702,393 A | 12/1997 | Pfaifer |
| 5,728,098 A | 3/1998 | Sherman et al. |
| 5,733,285 A | 3/1998 | Errico et al. |
| 5,810,819 A | 9/1998 | Errico et al. |
| 5,817,094 A | 10/1998 | Errico et al. |
| 5,863,293 A | 1/1999 | Richelsoph |
| 5,879,350 A | 3/1999 | Sherman et al. |
| 5,885,286 A | 3/1999 | Sherman et al. |
| 5,910,142 A | 6/1999 | Tatar |
| 5,961,517 A | 10/1999 | Biedermann et al. |
| 5,964,760 A | 10/1999 | Richelsoph |
| 5,989,250 A | 11/1999 | Wagner et al. |
| 5,997,539 A | 12/1999 | Errico et al. |
| 6,010,503 A | 1/2000 | Richelsoph et al. |
| 6,043,917 A | 3/2000 | Sonderegger et al. |
| 6,053,917 A | 4/2000 | Sherman et al. |
| 6,063,090 A | 5/2000 | Schlapfer |
| 6,132,432 A | 10/2000 | Richelsoph |
| 6,187,005 B1 | 2/2001 | Brace et al. |
| 6,254,602 B1 | 7/2001 | Justis |
| 6,280,442 B1 | 8/2001 | Barker et al. |
| 6,296,642 B1 | 10/2001 | Morrison et al. |
| 6,355,040 B1 | 3/2002 | Richelsoph |
| RE37,665 E | 4/2002 | Ralph et al. |
| 6,371,957 B1 | 4/2002 | Amrein et al. |
| 6,379,356 B1 | 4/2002 | Jackson |
| 6,402,752 B2 | 6/2002 | Schaffler-Wachter et al. |
| 6,451,021 B1 | 9/2002 | Ralph et al. |
| 6,478,797 B1 | 11/2002 | Paul |
| 6,485,491 B1 | 11/2002 | Farris et al. |
| 6,485,492 B1 | 11/2002 | Halm et al. |
| 6,488,681 B2 | 12/2002 | Martin et al. |
| 6,565,565 B1 | 5/2003 | Yuan et al. |
| 6,660,004 B2 | 12/2003 | Barker et al. |
| 6,726,689 B2 | 4/2004 | Jackson |
| 6,736,820 B2 | 5/2004 | Biedermann et al. |
| 6,740,086 B2 | 5/2004 | Richelsoph |
| 6,755,289 B2 | 6/2004 | Weiss |
| 6,827,719 B2 | 12/2004 | Ralph et al. |
| 6,837,889 B2 | 1/2005 | Shluzas |
| 6,840,940 B2 | 1/2005 | Ralph et al. |
| 6,858,030 B2 | 2/2005 | Martin et al. |
| 6,918,911 B2 | 7/2005 | Biedermann et al. |
| 6,974,460 B2 | 12/2005 | Carbone et al. |
| 7,022,122 B2 | 4/2006 | Amrein et al. |
| RE39,089 E | 5/2006 | Ralph et al. |
| 7,066,937 B2 | 6/2006 | Shluzas |
| 7,081,117 B2 | 7/2006 | Bono et al. |
| 7,087,057 B2 | 8/2006 | Konieczynski et al. |
| 7,090,674 B2 | 8/2006 | Doubler et al. |
| 7,125,426 B2 | 10/2006 | Moumene et al. |
| 7,128,743 B2 | 10/2006 | Metz-Stavenhagen |
| 7,144,396 B2 | 12/2006 | Shluzas |
| 7,163,539 B2 | 1/2007 | Abdelgany et al. |
| 7,198,627 B2 | 4/2007 | Bagger et al. |
| 7,211,086 B2 | 5/2007 | Biedermann et al. |
| 7,766,944 B2 | 8/2010 | Metz-Stavenhagen |
| 8,167,910 B2 | 5/2012 | Nilsson |
| 2002/0026193 A1 | 2/2002 | Barker et al. |
| 2002/0082602 A1 | 6/2002 | Biedermann et al. |
| 2002/0111626 A1 | 8/2002 | Ralph |
| 2002/0116001 A1 | 8/2002 | Schafer et al. |
| 2003/0004511 A1 | 1/2003 | Ferree |
| 2003/0100896 A1 | 5/2003 | Biedermann et al. |
| 2003/0125741 A1 | 7/2003 | Biedermann et al. |
| 2003/0125742 A1 | 7/2003 | Yuan et al. |
| 2003/0171755 A1 | 9/2003 | Moseley et al. |
| 2003/0187433 A1 | 10/2003 | Lin |
| 2004/0097933 A1 | 5/2004 | Lourdel et al. |
| 2004/0153077 A1 | 8/2004 | Biedermann et al. |
| 2004/0176766 A1 | 9/2004 | Shluzas |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0249380 A1 | 12/2004 | Glascott |
| 2005/0049588 A1 | 3/2005 | Jackson |
| 2005/0049589 A1 | 3/2005 | Jackson |
| 2005/0096659 A1 | 5/2005 | Freudiger |
| 2005/0113830 A1 | 5/2005 | Rezach |
| 2005/0119658 A1 | 6/2005 | Ralph et al. |
| 2005/0154391 A1 | 7/2005 | Doherty et al. |
| 2005/0187548 A1 | 8/2005 | Butler et al. |
| 2005/0228385 A1 | 10/2005 | Lott et al. |
| 2005/0267472 A1 | 12/2005 | Biedermann et al. |
| 2005/0277924 A1 | 12/2005 | Roychowdhury |
| 2005/0277927 A1 | 12/2005 | Guenther et al. |
| 2006/0004357 A1 | 1/2006 | Lee |
| 2006/0025767 A1* | 2/2006 | Khalili ............................ 606/61 |
| 2006/0084979 A1* | 4/2006 | Jackson ......................... 606/61 |
| 2006/0084995 A1 | 4/2006 | Biedermann et al. |
| 2006/0089643 A1 | 4/2006 | Muhwid |
| 2006/0129149 A1 | 6/2006 | Lott et al. |
| 2006/0149241 A1 | 7/2006 | Richelsoph et al. |
| 2006/0149244 A1 | 7/2006 | Amrein et al. |
| 2006/0155278 A1 | 7/2006 | Warnick |
| 2006/0161152 A1 | 7/2006 | Ensign et al. |
| 2006/0161153 A1 | 7/2006 | Hawkes et al. |
| 2006/0173450 A1 | 8/2006 | Shibata |
| 2006/0173456 A1 | 8/2006 | Hawkes et al. |
| 2006/0235389 A1 | 10/2006 | Albert et al. |
| 2006/0241599 A1 | 10/2006 | Konieczynski |
| 2006/0241600 A1 | 10/2006 | Ensign et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0293665 A1 | 12/2006 | Shluzas |
| 2006/0293666 A1 | 12/2006 | Matthis et al. |
| 2007/0055241 A1 | 3/2007 | Matthis et al. |
| 2007/0093817 A1 | 4/2007 | Barrus et al. |
| 2007/0093826 A1 | 4/2007 | Hawkes et al. |
| 2007/0093827 A1 | 4/2007 | Warnick |
| 2008/0045955 A1 | 2/2008 | Berrevoets et al. |
| 2008/0161859 A1 | 7/2008 | Nilsson |
| 2008/0177325 A1 | 7/2008 | Drewry et al. |

FOREIGN PATENT DOCUMENTS

| | | |
|---|---|---|
| EP | 1741396 A1 | 1/2007 |
| EP | 1743584 A1 | 1/2007 |
| WO | 02054966 A2 | 7/2002 |
| WO | 2004047657 A2 | 6/2004 |
| WO | 2006047711 A2 | 5/2006 |
| WO | 2006072284 A1 | 7/2006 |
| WO | 2006116437 A2 | 11/2006 |
| WO | 2006119271 A2 | 11/2006 |
| WO | 2007040750 A2 | 4/2007 |
| WO | 2007040750 A3 | 4/2007 |
| WO | 2008059507 | 5/2008 |

* cited by examiner

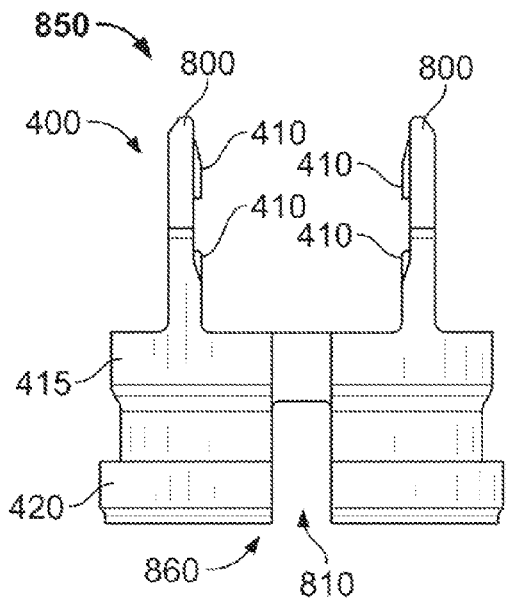
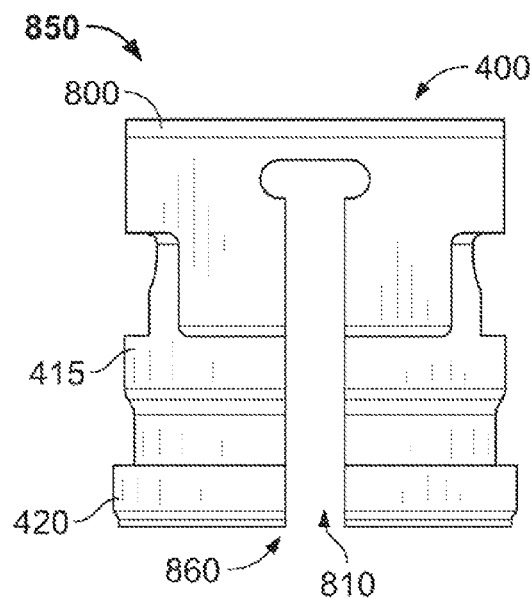
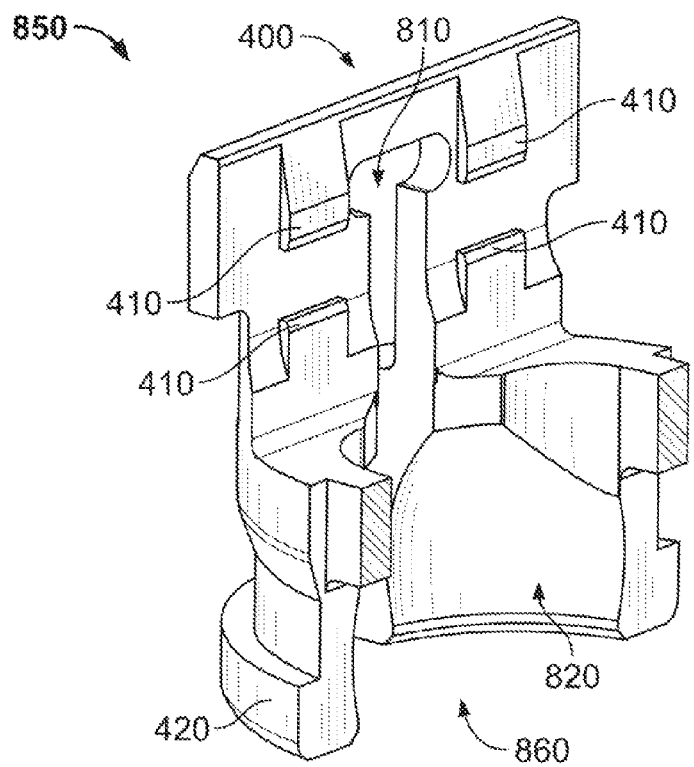

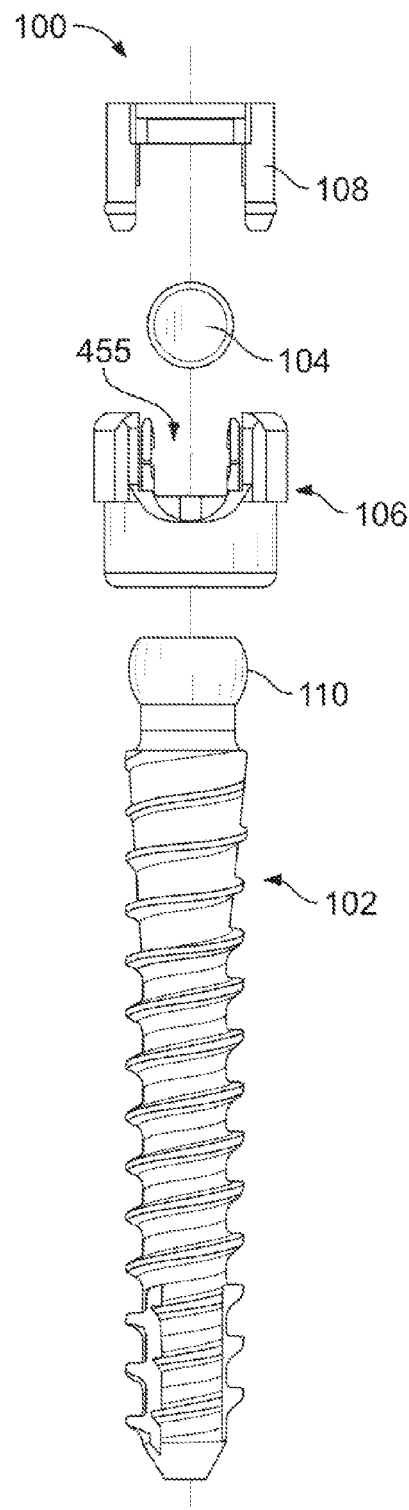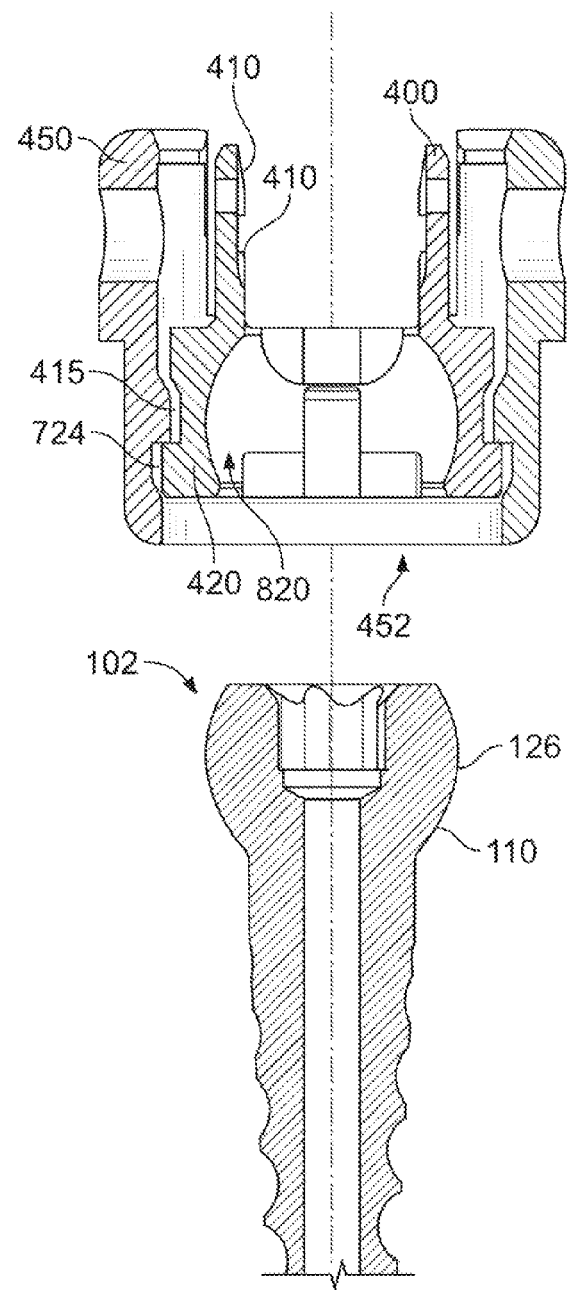
FIG. 11A
FIG. 11B

LOW PROFILE DUAL LOCKING FIXATION SYSTEM AND OFFSET ANCHOR MEMBER

RELATED APPLICATIONS

This application is a non-provisional application claiming the benefit of U.S. Provisional Applications 61/105,047 filed Oct. 14, 2008 and 61/105,048 filed Oct. 14, 2008, both of which are hereby incorporated by reference as if fully set forth herein.

FIELD OF THE INVENTION

The present systems and methods relate to bone fixation devices. More particularly, the present systems and methods provide for a low profile screw assembly configured to facilitate the internal fixation of vertebral bodies.

BACKGROUND OF THE INVENTION

Various devices for internal fixation of bone segments in the human or animal body are known in the art. For instance, pedicle screw and/or hook systems are sometimes used as an adjunct to spinal fusion surgery. Such systems may have a rod-receiving portion and an integral anchor portion, or may be provided with a separate anchor member, especially one that may be pivoted with respect to a rod-receiving member. Although pedicle screw systems, comprising a pedicle screw and a rod-receiving device, are commonly used, it is also possible to anchor a rod-receiving device to the spine with a different type of anchor member, such as a laminar hook. The pedicle screw portion of such a system includes an externally threaded stem and a head portion. The rod-receiving device (also referred to as a coupling device) couples the pedicle screw to a spinal rod by receiving and fixing the head portion of the pedicle screw and the elongate spinal rod (commonly referred to as a distraction rod). Two such systems are inserted into respective vertebrae and adjusted along the spinal rod to distract, de-rotate, and/or stabilize a spinal column, for instance to correct scoliosis or stabilize the spinal column in conjunction with an operation to correct a herniated disk. The pedicle screw does not, by itself, fix the spinal segment, but instead operates as an anchor point to fix the coupling device relative to the spinal segment into which the pedicle screw is driven, with the coupling device in turn receiving the rod extending therethrough. One goal of such a system is to substantially reduce and/or prevent relative motion between the spinal segments that are being fused.

Known pedicle screw systems have several drawbacks. For instance, some pedicle screw systems include rather large and bulky assemblies to secure a rod, thus increasing opportunities for tissue damage in and around the surgical site during installation. Many devices are also difficult to assemble and/or install. These problems become even more significant when implanting a coupling member and anchor member into smaller portions of the spine, such as the cervical vertebrae. For instance, installation of coupling members into adjacent cervical vertebrae often requires the central axis of the anchor member and coupling member of polyaxial pedicle screw systems to be pivoted to more extreme angles relative to each other than required in other vertebral regions, due to the size, proximity, and curvature of the vertebrae in the cervical spine.

SUMMARY OF THE INVENTION

In one aspect, low profile coupling devices for coupling an elongate member, such as a spinal rod, to one or more anchor members attached to vertebrae are provided herein. The anchor member may include a screw, hook, or other bone fixation device for securing implants to bone. Although the anchor member may be formed integrally with the inner or outer member, it is preferably provided as a separate structure and more preferably pivotably received in the coupling device to allow the coupling device to be fixed at various angles with respect to the anchor. This may be accomplished by providing the anchor with an enlarged, spherical or partially spherical head portion that is seated within the coupling device while a narrower shank portion of the anchor member extends outwardly from the coupling device through a passage in the device. In one form, the degree to which the anchor may be pivoted with respect to the coupling member may be increased by having the head portion of the anchor be offset from the shank portion or otherwise positioning the head portion of the anchor so that it is offset from the shank portion axis, so that when the head portion is in a neutral position in the coupling device the anchor shank can be pivoted in directions generally toward the offset head by a larger amount than otherwise would be possible if the anchor head and shank were aligned. The offset anchor head and shank are arranged such that the anchor head has a central axis that is offset from and extends generally parallel to the longitudinal axis of the shank of the anchor member so that when the anchor head is seated in the coupling device so that its central axis extends along the central axis of the coupling device, the longitudinal axis of the shank will be offset from the coupling device axis.

The rod-receiving or coupling device may be of many different configurations. For instance, in one form the coupling device has an outer member, an insert member for being received in the outer member, and a rod retaining member for securing the rod within the insert and/or outer members. If the anchor member is received in the inner member, the inner member includes at least one flexible portion that is shifted against the anchor member during linear shifting of the insert member relative to the outer member. A linearly inserted rod retaining member, such as a locking cap, interacts with the insert and/or outer members to shift a portion of the inner member against the elongate member, fixing the elongate member with respect to the coupling device. The assembly may be configured for independent locking of the anchor member and elongate member, so that one may be secured to the assembly before the other. For instance, the anchor member may be received within a lower portion of the insert member and secured therein by linear shifting of the insert member relative to the outer member, while the elongate member is received in an upper seat portion of the insert member and secured by linearly inserting the rod retaining member into engagement with the upper portion of the insert member.

An exemplary coupling device configured to couple a spinal rod to the head of a bone anchor includes a generally cylindrical insert axially received in an interior space of an annular outer member to form a tulip-shaped assembly. The insert member may include a lower portion with a generally spherical cavity configured to receive the head of an anchor member and an upper portion having a rod-receiving channel or seat. According to one exemplary embodiment, flexible, upstanding, laterally-spaced arms are arranged on either side of the channel and are configured to provisionally couple an elongate member by resiliently deflecting to grip a rod placed in the channel. The exemplary coupling assembly also includes an outer member or body having a bore, with at least a portion of the bore sized and configured to compress the insert member. After the head of the anchor member is received in the lower portion of the insert member, the outer member may be moved over the outer surface of the insert member, compressing the insert member to compressibly lock its lower portion onto the bone fixation device. Moreover, a rod retaining device engages the insert member and applies a compressive force radially toward the rod to secure the position of the rod. For instance, the rod retaining device may be provided in the form of a cap with at least one depending leg configured for friction fitting between the insert member and the outer member. Preferably, projections from the cap are wedged between an upper portion of the insert member and the outer member, deflecting one or more flexible portions of the insert member toward the rod and applying a compressive locking force thereto. This locking force is transverse to the axis of the anchor member and the axis of the coupling assembly, so that little or no cap structure need be provided above the rod, thus minimizing the height of the assembly.

In one form, the insert member may have a lower annular wall that forms a cavity or orifice configured for pivotably receiving the head of the bone fixation device therein, and one or more axial slits or gaps that extend through the annular wall to provide the annular wall with flexibility, allowing for expansion of the cavity. In such an arrangement, the anchor member may be snap-locked into the cavity of the insert member by deflecting portions of the annular wall to temporarily widen the opening to the interior cavity. Preferably, the snap-lock fit may apply a light compressive force onto the head of the anchor member so that the insert member may be positioned about the anchor head and then released with the frictional force between the wall lower surface and the anchor head being sufficient to retain the insert member at a desired orientation relative to the anchor member. However, the snap-lock fit may instead loosely retain the head without significant friction. The head may also be loosely received in the insert member without snap-locking.

The outer member has an interior space in the form of a through opening in which the insert member is received. In one form, the opening through the outer member may comprise at least one radially narrow portion and at least one radially wide portion, with the wide portion sized and configured to allow expansion of the insert member when located therein, and the narrow portion sized and configured to exert a radial compressive force upon the insert member. In such an embodiment, the head of the anchor member may be received by the insert member via a snap-lock fit when the insert member is located within the wide portion of the outer member in a substantially non-compressed configuration. Alternatively, substantially the entire space may be sized so that the walls exert a radial compressive force upon the insert member inserted therein, or one or more protrusions in the space may be configured to compress the insert member. The wall of the insert may also have a stepped configuration wherein wall portions are concentrically narrowed from top to bottom so that downward shifting of the insert member into the outer member sequentially achieves different stages of locking that apply different amounts of predetermined frictional force upon the anchor head.

The insert member and/or outer member may include one or more protrusions, recesses, or other structures to substantially prevent the insert member from unintentional separation from the outer member or backing out of the inner space of the outer member once inserted. This helps to prevent disengagement of the anchor member from the insert member while the assembly is manipulated under significant force, for instance during rotation of the vertebrae so that the device may receive the elongate member. The head of the anchor member may also be configured so that it may be shifted to multiple orientations within the insert member, at least one orientation reducing forces that expand the lower portion of the insert member in order to more securely retain the head within the tulip assembly.

An apparatus and method also are disclosed for the making and use of a reducer inserter tool for use with the disclosed coupling devices. The reducer/inserter tool is generally applicable to surgical instruments but is particularly suited to locking a spinal rod and cap onto a screw assembly, such as the screw assemblies described above or in U.S. Patent Application No. 2007/0225711, wherein an outer member, insert member, anchor member, and rod lock member or cap are all linearly (axially) assembled and locked together through axial movement to fix the anchor member and rod in place. The reducer inserter tool consists of three cannulated shafts shiftable within one another. The outer shaft functions as an exterior housing, and a hollow reducer shaft assembly or sleeve disposed concentrically within the outer shaft functions to reduce a rod (shift the rod into engagement with a screw assembly). An inner drive shaft disposed concentrically within the reducer shaft functions to drive a cap or other rod locking member into the coupling assembly to lock the rod.

BRIEF DESCRIPTION OF THE DRAWINGS

The accompanying drawings illustrate various exemplary embodiments of systems and methods for securing an elongate member to the spine and are a part of the specification. Together with the following description, the drawings demonstrate and explain the principles of the systems and methods. The illustrated embodiments are examples of the systems and methods and do not limit the scope thereof.

FIGS. 8A-8C are front, side, and cut-away perspective views, respectively, of an insert member, according to one exemplary embodiment.

FIGS. 11A and 11B are an exploded front view and a cross-sectional perspective view, respectively, of the components of a pedicle screw system prior to assembly, according to one exemplary embodiment.

Throughout the drawings, identical reference numbers designate similar but not necessarily identical elements.

DETAILED DESCRIPTION OF THE PREFERRED EMBODIMENTS

Figure 1A:
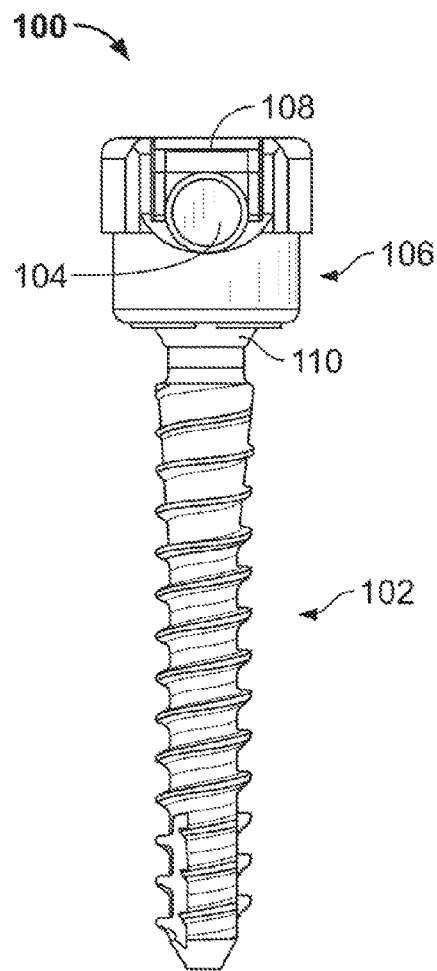
FIGS. 1A and 1B are an axial view and a transverse view, respectively, of a spinal rod coupled to an exemplary assembled pedicle screw system having a rigid outer member and compressible insert member.

FIGS. 1-43 illustrate systems and methods for locking the orientation of an anchor member and elongate member with respect to a first type of coupling assembly, sometimes referred to as a "tulip assembly," in which an insert member is inserted linearly into a space within an outer member. Axial shifting of the outer member and insert relative to one another (and the consequent radial compression exerted thereby) locks the position of the coupling assembly relative to an anchor member or fixation device (e.g. a pedicle screw or hook). Further, according to one exemplary embodiment, a coupling assembly may be configured to be placed on the head of a polyaxial pedicle screw after placement of the pedicle screw in a patient's body and configured to receive and positionally secure a top loaded rod. Further details of the present exemplary system and method will be provided below.

By way of example, pedicle screw systems may be fixed in the spine in a posterior lumbar fusion process via minimally invasive surgery (MIS) techniques. The systems are inserted into the pedicles of the spine and then interconnected with rods to manipulate (e.g., correct the curvature, compress or expand, and/or structurally reinforce) at least portions of the spine. Using the MIS approach to spinal fixation and/or correction surgery, in which implantation and manipulation of the system are accomplished through relatively small openings, has been shown to decrease a patient's recovery time and reduce the risks of follow-up surgeries.

The ability to efficiently perform spinal fixation and/or correction surgeries using MIS techniques is enhanced by the use of pedicle screw systems provided in accordance with the present exemplary systems and methods, which systems and methods provide a number of advantages over conventional systems. For example, a pedicle screw system in accordance with one embodiment of the present exemplary system and method provides the advantage that the pedicle screw (or other type of anchor member) may be inserted into the bone without being pre-operatively coupled with the coupling assembly. This is advantageous because the surgeon often needs to do other inter-body work after inserting the pedicle screw, but before attaching the larger and bulkier coupling assembly. This also allows the fixation device to be positioned within the body and secured to the spine without the assembly obscuring the surgeon's view or contact with the pedicle screw. Such an advantageous pedicle screw system may be even more crucial when using MIS techniques because the inter-body spatial boundaries in which the surgeon must work may be quite limited.

In addition, pedicle screw systems in accordance with several embodiments of the present system and method advantageously allow a user to fix (e.g., lock) the coupling assembly to the pedicle screw at a desired angle either before or after inserting and/or capturing the rod. Fixing or locking the coupling assembly to the pedicle screw means that at least one of the components of the coupling assembly is manipulated to grip and/or clamp onto the pedicle screw to reduce and/or prevent any translational and/or rotational movement of the coupling assembly relative to the pedicle screw. In fact, the assembly may be configured to have both provisional screw lock and final screw lock positions, so that in the provisional screw lock position or positions the coupling assembly grips the screw head with sufficient force to maintain a selected angulation of the assembly with respect to the screw unless force is applied by hand or instrument to change said angulation, whereas the final screw lock position applies a greater force to the screw head than the provisional lock and maintains the assembly at a selected angulation with respect to the screw with sufficient force to prevent movement thereof under physiological loads generated by the body. The ability to lock the coupling assembly to the pedicle screw prior to placing the rod into the coupling assembly may facilitate the surgeon in performing compression and/or distraction of various spinal and/or bone sections.

Similarly, the assembly may have provisional rod locking positions for loosely retaining the rod so that it is coupled to the assembly but may still be manipulated (e.g. shifted or rotated) therein prior to full rod locking.

The term "distraction," when used herein and when used in a medical sense, generally relates to joint surfaces and suggests that the joint surfaces move perpendicular to one another. However when "traction" and/or "distraction" is performed, for example on spinal sections, the spinal sections may move relative to one another through a combination of distraction and gliding, and/or other degrees of freedom.

Another advantageous feature of at least one embodiment of the present exemplary system and method is that the complete coupling assembly can be coupled to the head portion of the pedicle screw intra-operatively. This advantageous coupling assembly may include aspects or features that enable the coupling assembly to be provisionally or fully locked onto the head portion of the pedicle screw and then to further receive, capture, and finally lock the rod into the coupling assembly. This advantageous coupling assembly may decrease the complexity of the pedicle screw system installation by reducing the installation to essentially a three-step process including: inserting the pedicle screw into bone, coupling and/or locking the coupling assembly to the pedicle screw, which may be accomplished with or without the rod in the coupling assembly, and then locking the rod into the coupling assembly. However, the system need not be installed following these steps in the aforementioned order. For instance, the coupling assembly may be coupled to the pedicle screw, and even provisionally and/or finally locked to the screw, prior to implantation of the screw into bone so that the screw and coupling assembly are implanted simultaneously. Furthermore, the screw locking and rod locking steps may be accomplished simultaneously rather than as separate steps. In addition to accommodating the MIS approach to spinal correction and/or fusion, the present exemplary systems and methods are configured to eliminate instances of cross-threading and/or post-operative splaying of the assembly, which may be caused by forces exerted by postoperative back flexion that open the coupling assembly and eventually lead to the disassembly and/or the failure of the pedicle screw system.

In the following description, for purposes of explanation, numerous specific details are set forth in order to provide a thorough understanding of the present system and method for providing a low top pedicle screw coupling system that is capable of separately locking the orientation of a coupling assembly relative to a pedicle screw and a positional location of a rod in the coupling assembly. It will be apparent, however, to one skilled in the art that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Overall Structure of FIGS. 1-16

While the present system and method may be practiced by or incorporated into any number of bone fixation systems, the present system and method will be described herein, for ease of explanation only, in the context of a pedicle screw system. Accordingly, the present system and method includes, according to one exemplary embodiment illustrated in FIGS. 1A and 1B, a low top pedicle screw system 100 including a pedicle screw 102, a rod 104, and a rod-receiving assembly or coupling assembly 106 (sometimes referred to as a tulip assembly) including a low profile rod lock member such as a compression cap 108. According to one exemplary embodiment of the present system and method, the coupling assembly 106 is configured to separately lock the orientation of the coupling assembly 106 relative to the pedicle screw 102 and the positional location of the rod 104 in the coupling assembly 106. Operation of the coupling assembly 106 as well as its interaction with both the pedicle screw 102 and the rod 104 will be described in further detail below with reference to the Figures.

Figure 1B:
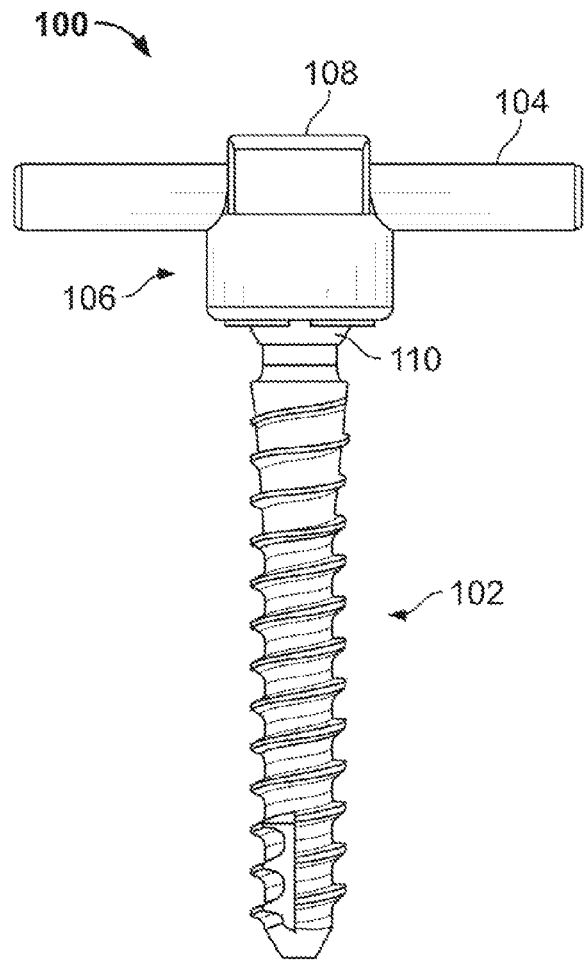

According to one exemplary embodiment, FIGS. 1A and 1B generally show a pedicle screw system 100 comprising a pedicle screw 102, a rod 104, and a coupling assembly 106, hereinafter referred to as a coupling assembly 106. As illustrated in FIG. 1, the pedicle screw system 100 is configured to securely couple the coupling assembly 106 to the head 110 of the pedicle screw 102, thereby locking or fixing the coupling assembly 106 in an angular position relative to the pedicle screw 102. Additionally, as shown in FIGS. 1A and 1B, the present exemplary pedicle screw system 100 is configured to receive a rod 104 and positionally fix the rod 104 in the coupling assembly 106.

Figure 2:
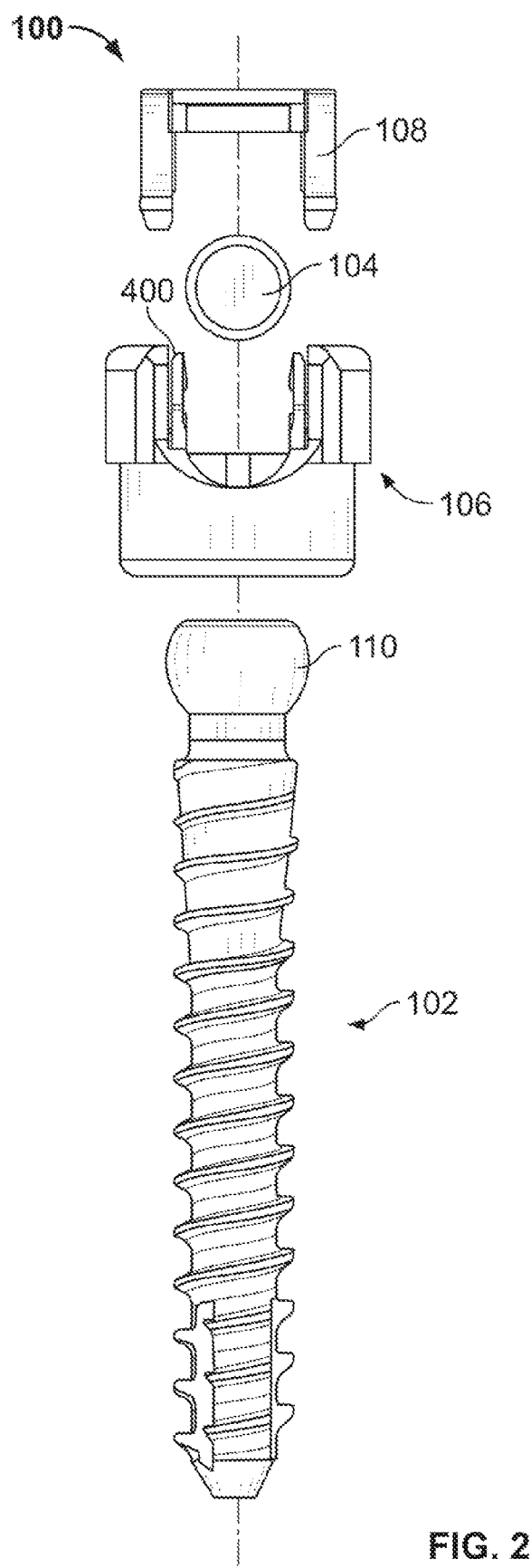
FIG. 2 is an exploded axial view of a spinal rod and a pedicle screw system having a rigid outer member and compressible insert member.

FIG. 2 illustrates an exploded view of the present low top pedicle screw system 100, according to one exemplary embodiment. As illustrated in FIG. 2, the coupling assembly 106 of the low top pedicle screw system 100 includes a number of components configured to perform the above-mentioned angular and positional fixing including, but in no way limited to, an outer member or yoke 450, an insert member or core member 400, and a compression cap 108. According to one exemplary embodiment, the coupling assembly 106 including the insert member 400 is configured for insertion into the outer member and further configured to engage the head portion 110 of the pedicle screw 102, as described in further detail below. Moreover, the coupling assembly 106 in connection with the compression cap 108 is configured to securely couple the rod 104 to the assembly. Detailed descriptions of each component of the present low top pedicle screw system 100 will be described in further detail below, with reference to FIGS. 3 through 9B.

Figure 3:
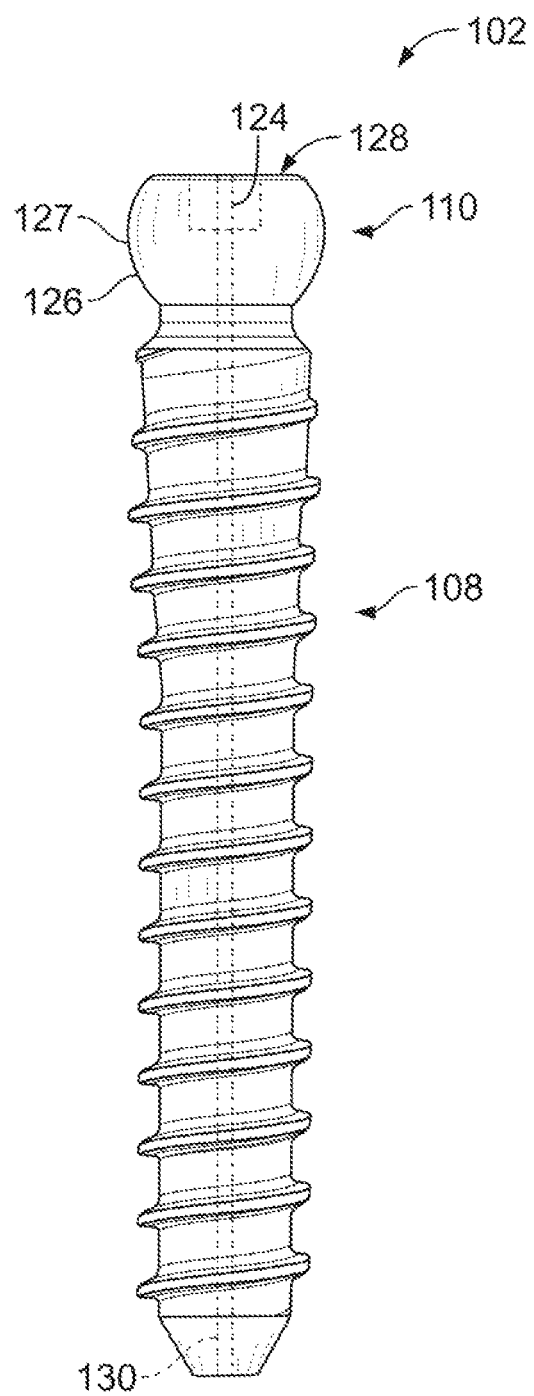
FIG. 3 is a perspective view of a pedicle screw.

FIG. 3 further illustrates the components of a pedicle screw 102, according to one exemplary embodiment. As illustrated in FIG. 3, the pedicle screw 102 includes an elongated, threaded portion 108 and a head portion 110. Although pedicle screws are generally known in the art, the head portions may be of varying configurations depending on what type of coupling assembly is to be coupled to the pedicle screw. The head portion 110 of the present exemplary pedicle screw 102 includes a driving feature 124 and a maximum diameter portion 126. The driving feature or recess 124 of the present exemplary pedicle screw 102 permits the screw to be inserted and rotated into a pedicle bone and/or other bone. The pedicle bone is a part of a vertebra that connects the lamina with a vertebral body. Additionally, according to the present exemplary embodiment, the driving feature 124 can be used to adjust the pedicle screw 102 prior to or after the coupling assembly 106 is coupled to the pedicle screw 102. In the illustrated embodiment, the head portion 110 of the pedicle screw 102 is coupled to the threaded portion 108 and includes a generally spherical surface 127 with a truncated or flat top surface 128.

In one exemplary embodiment, the pedicle screw 102 is cannulated, which means a channel 130 (shown in dashed lines and extending axially through the pedicle screw 102) extends through the entire length of the pedicle screw 102. The channel 130 allows the pedicle screw 102 to be maneuvered over and receive a Kirschner wire, commonly referred to as a K-wire (not shown). The K-wire is typically pre-positioned using imaging techniques, for example, fluoroscopy imaging, and then used to provide precise placement of the pedicle screw 102. Numerous variations of the pedicle screw may be made including, but in no way limited to, varying the type of driving feature 124, varying materials, varying dimensions, and the like. The screw may also be formed integrally with the coupling assembly instead of having a head portion that is pivotably received in a separate coupling assembly.

Figure 4:
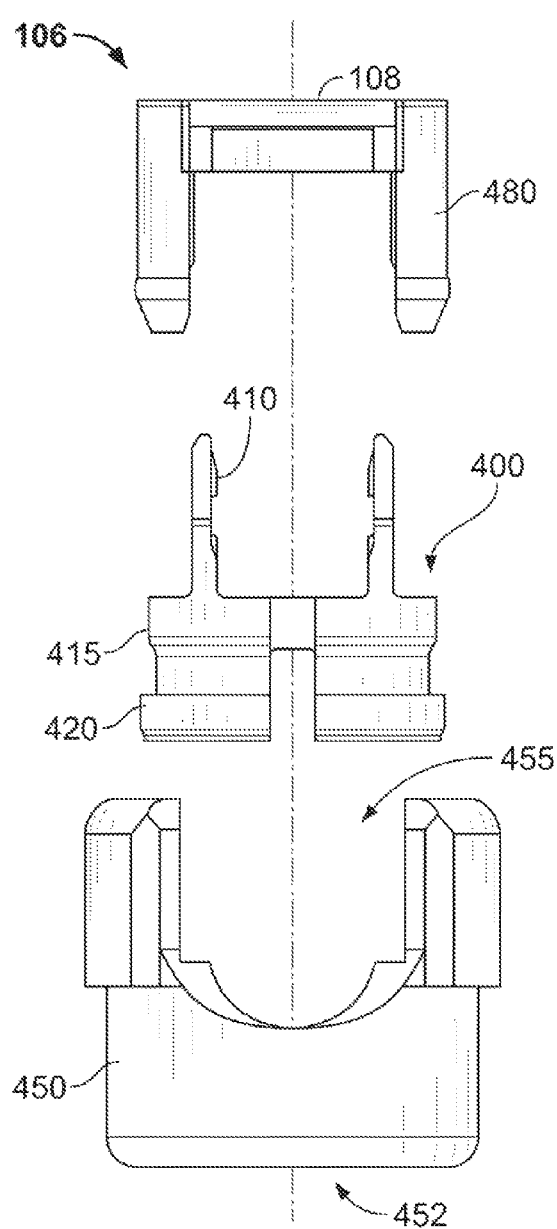
FIG. 4 is a front exploded view of a coupling assembly of the pedicle screw system of FIG. 1, according to one exemplary embodiment.
Figure 5:
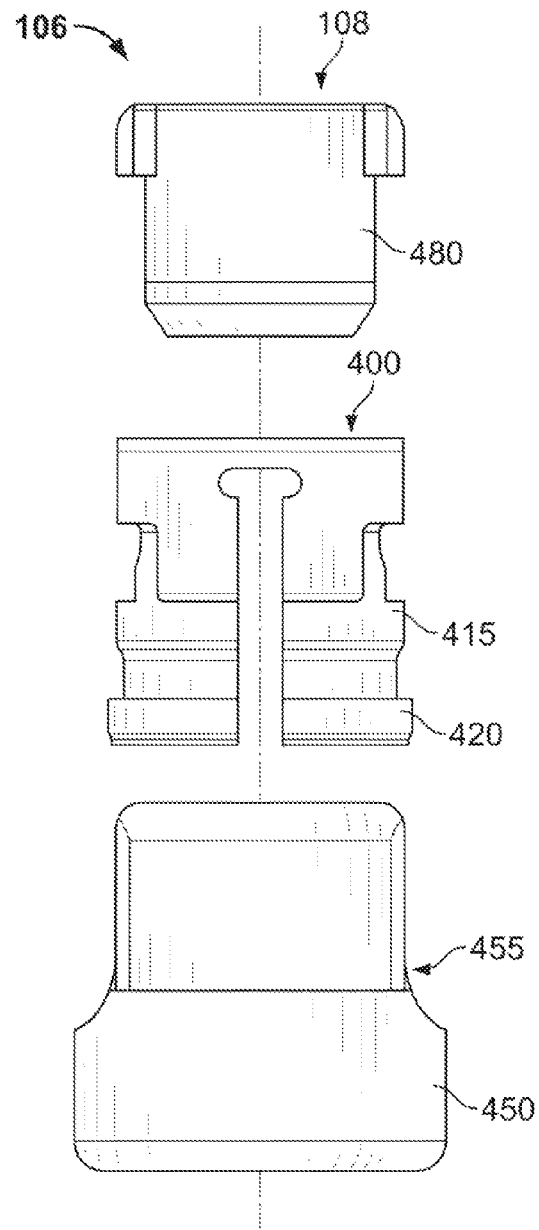
FIG. 5 is a side exploded view of a coupling assembly of the pedicle screw system of FIG. 1, according to one exemplary embodiment.
Figure 6:
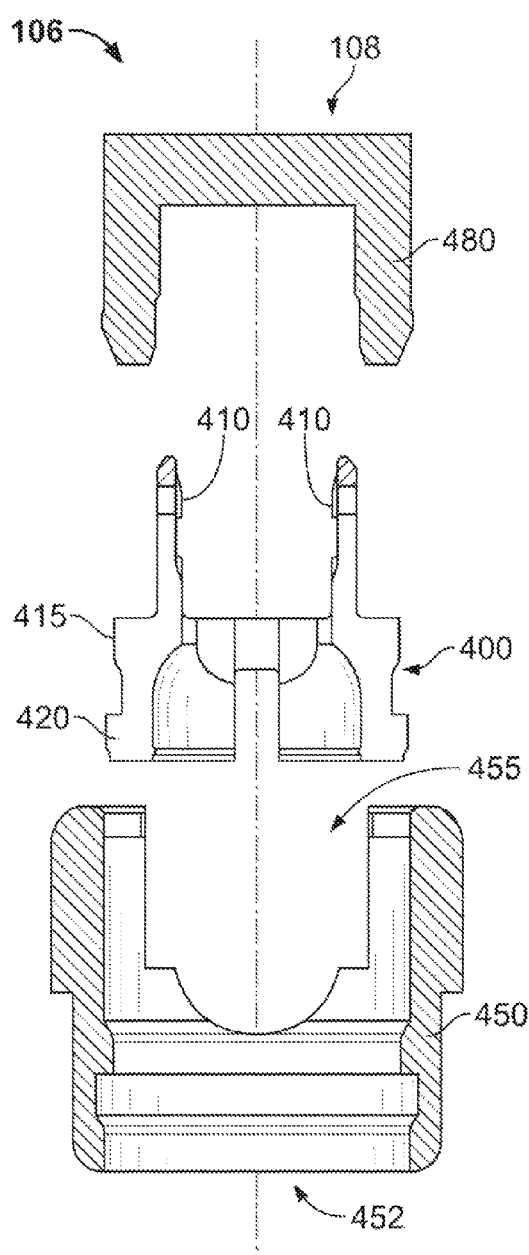
FIG. 6 is a front exploded cross-sectional side view of the pedicle screw system of FIG. 4, according to one exemplary embodiment.

Returning again to FIG. 1, the pedicle screw system includes a coupling assembly 106 configured to separately lock the orientation of the coupling assembly 106 relative to the pedicle screw 102 and the positional location of the rod 104 within the coupling assembly 106. FIGS. 4, 5, and 6 illustrate the various components of the present exemplary coupling assembly 106, according to one exemplary embodiment. FIG. 4 illustrates a front (along the axis of a captured spinal rod) exploded view of an exemplary coupling assembly 106, while FIG. 5 illustrates an exploded view of the present exemplary coupling assembly 106 as viewed from the side (transverse to a captured rod). Furthermore, FIG. 6 provides a front cross-sectional view of the present exemplary coupling assembly 106. As illustrated in FIGS. 4-6, the present exemplary coupling assembly 106 includes an outer member or body 450 substantially housing an insert member 400. Additionally, a throughbore 452 is defined in the center of the coupling assembly 106, through both the insert and outer members, to provide a driving tool access to the driving feature 124 in a pedicle screw captured by the coupling assembly. In addition, the throughbore allows a K-wire to be passed through the coupling assembly and associated cannulated screw. The outer member 450 also defines a rod recess 455 configured to define an ultimate rod position during use.

As shown, the insert member 400 may include a number of functional features including, but in no way limited to a plurality of spaced apart rod engagement members or arms 410 configured to receive a spinal rod. Additionally, a proximal locking feature 415 and a distal locking feature 420 are formed on the outer surface of the insert member 400 in order to interact with the outer member 450 and selectively capture the head 110 of a pedicle screw 102. The locking features 415 and 420 shown are formed as annular flanges extending from the lower portion of the insert member 400. Furthermore, the exemplary illustrated compression cap 108 includes a plurality of compression protrusions in the form of legs 480 that cooperate with the insert 400 and outer member 450 to lock the rod. Consequently, the exemplary configurations of the outer member 450, the insert member 400, and the compression cap 108 will each be independently addressed in detail below.

Figure 7A:
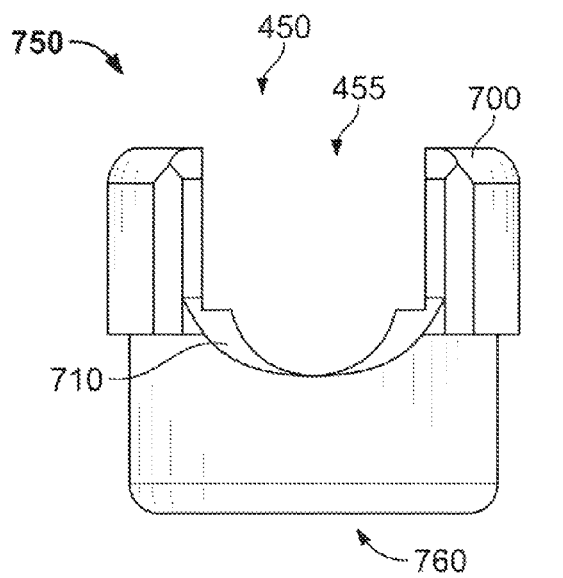
FIGS. 7A-7D are front, side, front cross-sectional, and cut-away perspective views, respectively, of an outer member of a coupling assembly, according to one exemplary embodiment.
Figure 7B:
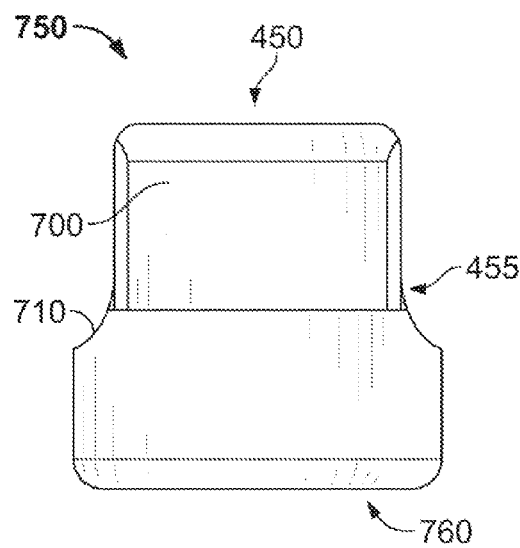
Figure 7C:
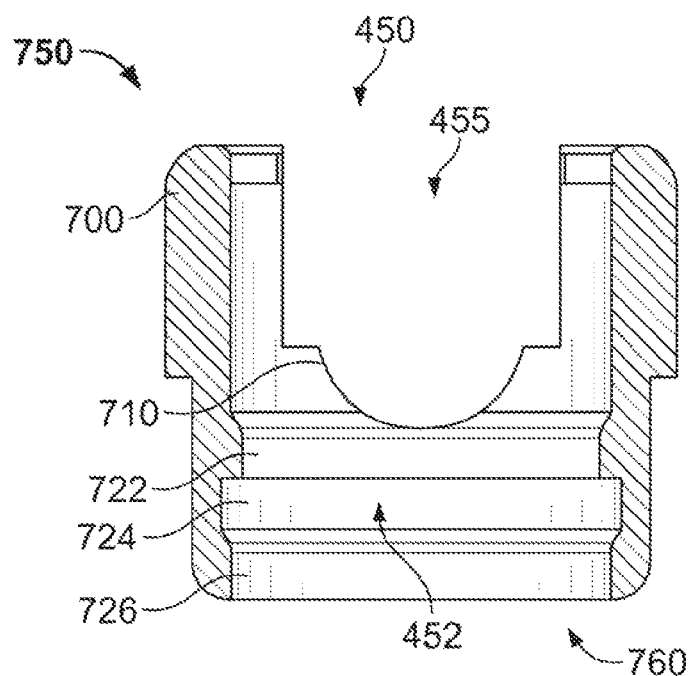
Figure 7D:
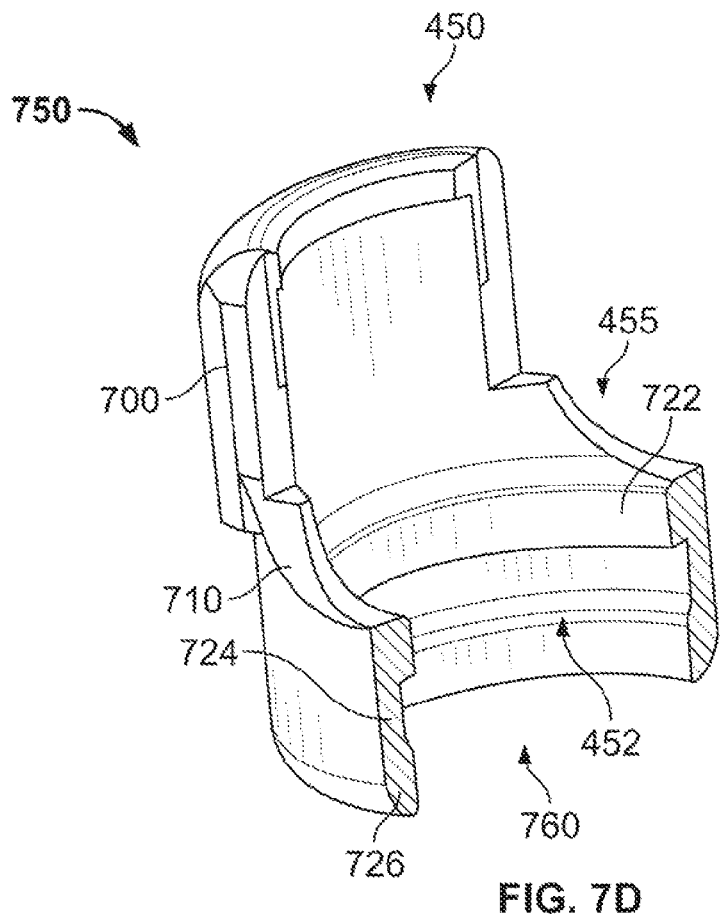

FIG. 7A illustrates a front view of an outer member 450, FIG. 7B illustrates a side view of the outer member, FIG. 7C illustrates a cross-sectional view of the outer member, and FIG. 7D illustrates a partial cut-away perspective view of an outer member according to one exemplary embodiment. As illustrated in FIGS. 7A through 7D, the outer member 450 includes a number of elements that facilitate the ability to separately lock both the positions of the pedicle screw 102 and a rod 104 relative to the coupling assembly 106. According to one exemplary embodiment illustrated in FIGS. 7A through 7D, the outer member 450 includes an internal space 452 in the form of a throughbore, a proximal end 750, a distal end 760, a rod reception recess 455 defined by upright side walls 700, and a number of internal annular features 722, 724, and 726 configured to allow for the selective compression and expansion of an insert member (FIGS. 4, 8).

According to one exemplary embodiment, the bore 452 is configured to permit assembly of the outer member and insert before being placed onto the head portion of the pedicle screw. In one embodiment, the insert member 400 of the coupling assembly may be inserted into the outer member 450 through the bore 452. Once the coupling assembly 106 is pre-operatively assembled, a wide portion of the bore facilitates reception of the head portion 110 of the pedicle screw 102 within the insert member 400, as will be described in further detail below.

Continuing with FIGS. 7A through 7D, the outer member 450 is illustrated as a generally cylindrical member having a plurality of side walls 700 extending toward the proximal end 750 of the outer member. According to one exemplary embodiment, the plurality of side walls 700 define both the proximal portion of the thru-bore 452 and the rod recess 455 including a rod stop surface 710. The rod stop surface may be contoured to match the outer surface of the rod. In the illustrated embodiment, the proximal portion of the outer member 450 is open to receive a spinal rod. As mentioned, the rod 104 may be inserted into the outer member 132 either before or after placement of the coupling assembly 106 on the head portion 110 of the pedicle screw 102. Initially, the rod 104 is received by both the insert member 400 and the outer member 450 via the rod recess 455. Consequently, according to one exemplary embodiment, the width of the rod recess 455 may be substantially equal to or greater than the diameter of a desired rod 104. However, according to other exemplary embodiments, the rod recess 455 may be slightly narrower than the diameter of a desired rod 104 to allow for a slight interference fit during insertion. Once the rod 104 is received by the outer member 450 and the insert member 400 via the rod recess 455 the lateral motion of the rod is limited by the sidewalls 700 and/or the upright arms 410 of the insert member, and in some embodiments the vertical position of the rod may be limited, at least in part, by the rod stop surface 710.

Figure 18:
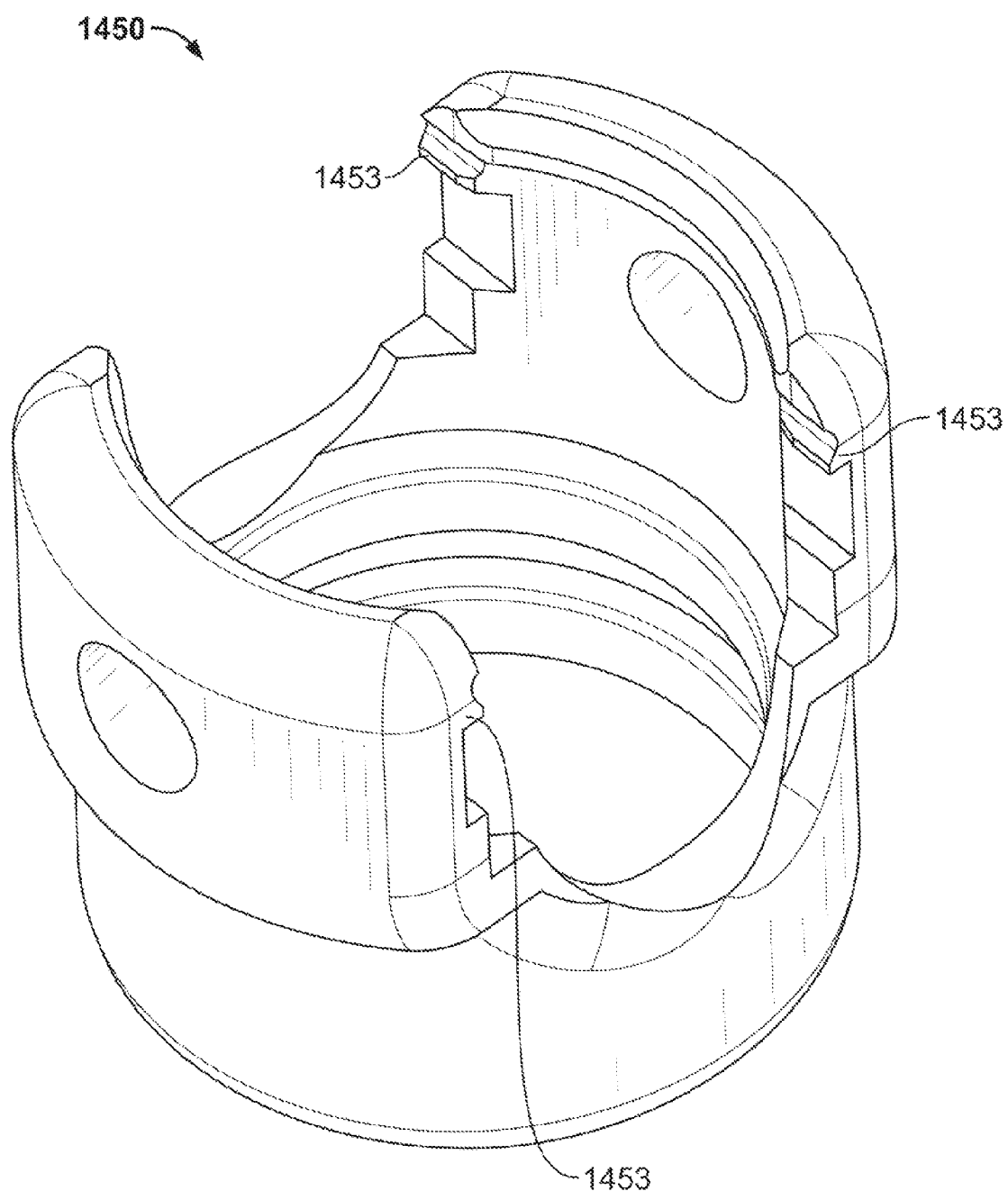
FIG. 18 is a perspective view of an exemplary embodiment of an outer member with inwardly-facing retention features and with bores in its side surfaces for receiving an instrument.

The present exemplary outer member 450 also includes a number of elements that allow the relative angular position of the coupling assembly 106 to be independently established relative to the pedicle screw 102. Specifically, the internal wall of the outer member 450 defining the throughbore 720 can include, according to one exemplary embodiment, a proximal annular compression feature or locking feature 722, a distal annular compression feature or locking feature 726 and an annular expansion groove 724. According to one exemplary embodiment, the proximal and distal annular compression features 722, 726 are configured to interact with the proximal locking feature 415 and distal locking feature 420 (FIG. 4) of the insert member to compress the insert member about the head portion of the pedicle screw, thereby fixing the relative angular position of the coupling assembly relative to the pedicle screw, as will be described below with reference to FIGS. 10 through 16B. Additionally, according to one exemplary embodiment, the annular expansion groove 724 is configured to permit selective expansion of the insert member 400 to facilitate reception of the head portion 110 of the pedicle screw 102 when the distal annular locking feature is positioned in the annular groove of the outer member, as will be described in detail below. While the present figures and description describe the internal compression and expansion features as annular protrusions and recesses, any number of selectively disjointed, or varying protrusions or recesses may be used to allow selective expansion and compression of the present insert member 400. The exterior of the outer member may contain features to interact with tools designed to implant and operate the assembly. For instance, as shown in FIG. 18, an outer member may contain radially-directed bores or openings so that portions of an instrument may transversely engage and grip the outer member and be used to position the outer member during implantation or shifting of the outer member relative to the insert member during locking.

The insert member 400 of one illustrated coupling assembly is illustrated in FIGS. 8A through 8C. As shown by the side axial view of FIG. 8A, the insert member 400 can generally, according to one exemplary embodiment, include a main body having a proximal end 850 and a distal end 860. As shown, the main body of the insert member 400 includes a plurality of rod retention members 800 in the form of a pair of upright arms extending therefrom in a proximal direction. According to one exemplary embodiment, the arms 800 include a number of rod engagement features in the form of ridges 410 formed on inner surfaces of the arms. According to one exemplary embodiment, the arms 800 are spaced apart a proper distance to receive a desired rod 104 and contact and retain the desired rod at the ridges 410. As shown in FIG. 8A, an expansion gap 810 may be formed in the distal end 860 of the insert member 400 to facilitate expansion and contraction of the rod retention arms 800. Additionally, as previously mentioned, the insert member 400 can include a proximal locking feature 415 and a distal locking feature 420 configured to selectively interact with features of the outer member 450, including the proximal annular compression feature 722, the annular expansion gap 724, and the distal annular compression feature 726. According to one exemplary embodiment, the main body and the rod retention arms of the insert member 400 are sized to be received in the throughbore 452 of the outer member 450 and then be selectively shifted within the outer member to compress the head portion of a desired pedicle screw 102, as will be described in more detail below.

Turning now to FIG. 8B, which is a side view of the insert member 400, the body of the insert member defines an expansion gap 810 that begins at the distal end 860 of the insert member 400 and extends into the upper rod retention arms 800. According to one exemplary embodiment, the large expansion gaps 810 defined in the insert member 400 facilitate expansion of the distal end 860 of the insert member, thereby allowing for reception of a head portion of a desired pedicle screw 102. As shown in FIG. 8C, the distal end 860 of the insert member 400 defines a screw head receiving orifice or cavity 820 configured to provide a large surface area of contact with a received pedicle screw head. As will be described in further detail below, the aforementioned features of the insert member 400 work in conjunction with the features of the outer member 450 and the compression cap 108 to selectively fix the position of the present coupling assembly 106 relative to a pedicle screw and independently receive, capture, and eventually positionally lock a rod 104 into the coupling assembly. According to one exemplary embodiment, a forced contraction of the distal end 860 of the insert member 400 generates sufficient radial pressure on the head portion 110 of the pedicle screw 102 to lock the relative angular position of the coupling assembly with respect to the pedicle screw.

Figure 9A:
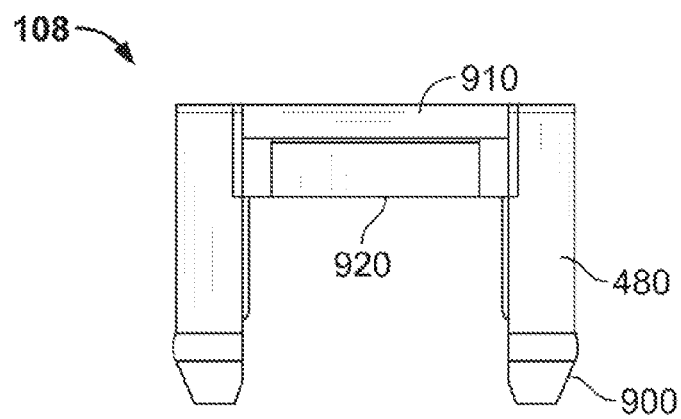
FIGS. 9A-9C are front, side, and cut-away perspective views, respectively, of a compression cap, according to one exemplary embodiment.
Figure 9B:
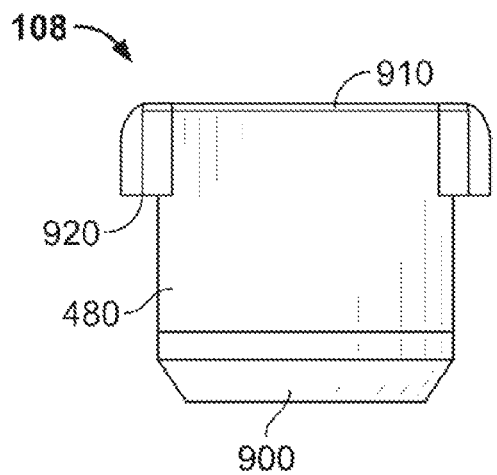
Figure 9C:
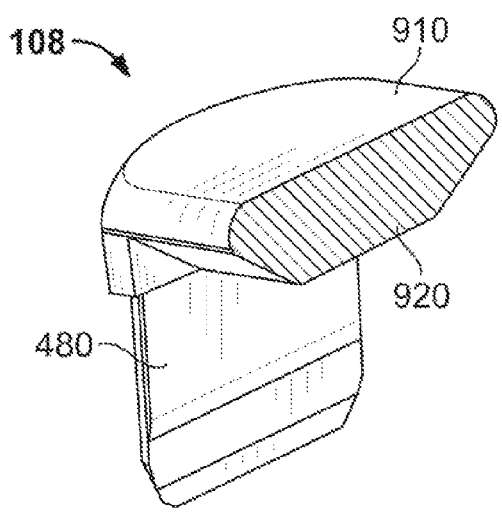

FIGS. 9A through 9C illustrate one type of rod locking member of the present exemplary system and method, a compression cap 108. According to one exemplary embodiment, the compression cap 108 is designed to provide a low profile for the assembly (having a minimal amount of material above the rod), while preventing post operative assembly splaying. Particularly, as shown in FIGS. 9A through 9C, the compression cap 108 includes a top surface 910 and a bottom rod mating surface 920. According to one exemplary embodiment, a plurality of compression protrusions in the form of legs 480 extend distally from the bottom rod mating surface 920 of the compression cap 108. According to one exemplary embodiment, described in further detail below, each of the compression protrusions 480 are configured to be inserted between the rod retention arms 800 of the insert members 400 and the side walls 700 of the outer member 450. According to one exemplary embodiment, forcing the compression protrusions 480 between the rod retention protrusions 800 of the insert members 400 (FIG. 8A) and the side walls 700 of the outer member 450 (FIG. 7A) both compresses the arms into contact with a captured rod 104 and prevents the insert member 400 from splaying post operatively. As shown in FIGS. 9A and 9B, the most distal portion of the compression cap legs 480 may include an engagement bevel 900 configured to facilitate the insertion of the compression protrusions between the rod retention protrusions 800 of the insert members 400 and the side walls 700 of the outer member 450. In addition, the beveled portions 900 may extend laterally outward from the legs 480 to allow the compression cap 108 to snap-lock into the outer member before the cap is fully inserted. While a number of traditional rod retention systems include anti-splaying mechanisms, they are typically bulky and greatly increase the overall height of the mechanism. In contrast, the present compression cap 108 protects against post operative splaying of the system while minimally impacting the height of the resulting assembly. That is, the only height of the present coupling assembly 106 above a captured rod when fully assembled is the distance between the rod mating surface 920 and the top surface 910 of the compression cap 108, as illustrated in FIG. 9A. Furthermore, the rod locking member could be formed without a top portion to further reduce the profile of the assembly. For instance, a single wedge member or a pair of unconnected wedge members could be inserted between the outer member and the arms of the insert to lock the rod.

Further detail of the function and operation of the present coupling assembly will be described below with reference to FIGS. 10-16B.

Exemplary Implementation and Operation of the Coupling Device Shown in FIGS. 1-16

Figure 10:
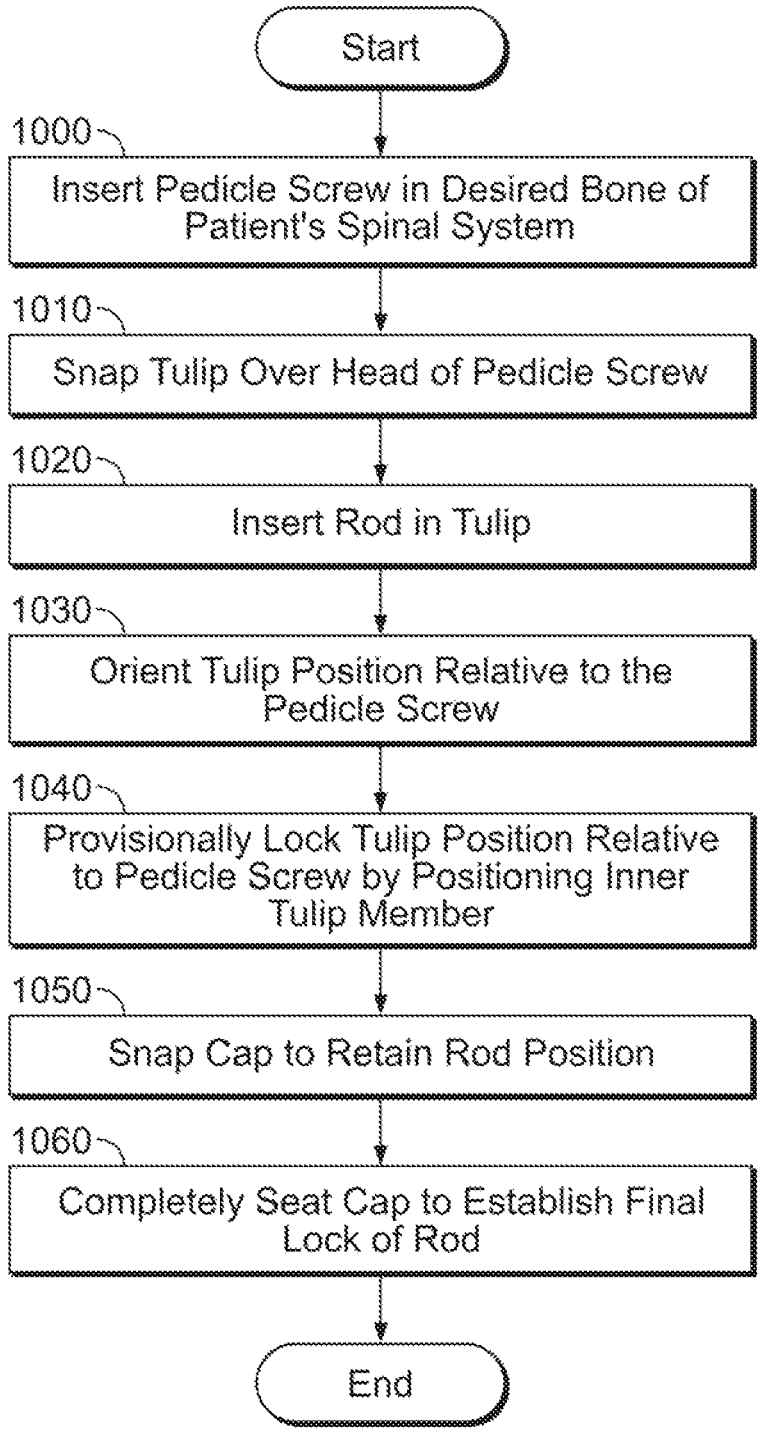
FIG. 10 is a flow chart illustrating a method for securing an axially locking coupling assembly on a pedicle screw, according to one exemplary embodiment.

FIG. 10 illustrates one method for installing an exemplary low top pedicle screw system 100 (FIG. 1). As illustrated in FIG. 10, the present exemplary method for installing the low top pedicle screw system includes inserting one or more pedicle screws in a patient's spinal system (step 1000). Once the one or more pedicle screws are inserted in a patient's spinal system, the coupling assembly (106, FIG. 1) is installed over the head of the pedicle screw (step 1010). With the coupling assembly snapped over the head of the pedicle screw, a rod may be inserted into the rod recess of the insert member (step 1020) and the relative position of the coupling assembly may be oriented as desired relative to the pedicle screw (step 1030). When the desired orientation is established, the coupling assembly position relative to the pedicle screw may be locked by linearly shifting the elements of the system relative to one another. The insert member 400, outer member 450, and compression cap 108 all share a common axis, and may be shifted relative to one another along the axis. The outer member 450 may be shifted over the insert member 400 in a first, upward direction, and the compression cap 108 may be shifted in an opposite direction from the opposite side of the insert member 400 so that the legs 480 of the compression cap are inserted between the insert member 400 and outer member 450.

By positioning the insert member (step 1040), shifting the insert member relative to the outer member, the angular position of the screw relative to the assembly is fixed. With the coupling assembly position relative to the pedicle screw established due to the positioning of the insert member, the compression cap may be snapped into the assembly to block exit of the rod (step 1050) followed by a complete insertion of the compression cap for a final lock of the rod (step 1060). Alternatively, the compression cap may be inserted into the assembly as the outer member is pulled up around the insert member, simultaneously locking the rod 104 and the screw 102 into place. Further details of each step of the present exemplary method will be provided below with reference to FIGS. 11A through 16B.

As illustrated in FIG. 10, the first step of the exemplary method is to insert one or more pedicle screws in a patient's spinal system (step 1000) corresponding to a desired number of pedicle screw systems 100; FIG. 1. The placement and/or number of pedicle screw systems 100 to be used in a patient may be pre-operatively determined based on a pre-operative examination of the patient's spinal system using non-invasive imaging techniques known in the art, such as x-ray imaging, magnetic resonance imaging (MRI), and/or fluoroscopy imaging, for example.

With the one or more pedicle screws inserted into a patient's spinal system (step 1000), the coupling assembly may be snapped over the head of a previously inserted pedicle screw (step 1010). FIGS. 11A and 11B illustrate the exemplary components prior to installation on an inserted pedicle screw 102. As illustrated, the insert member 400 is in an up position aligning the distal locking feature 420 of the insert member 400 with the annular expansion groove 724 of the outer member 450. According to one exemplary embodiment, this configuration allows for the expansion of the head receiving orifice 820, thereby facilitating the reception of the head portion 110 of the pedicle screw 102. More specifically, according to one exemplary embodiment, the alignment of the distal locking feature 420 of the insert member 400 with the annular expansion groove 724 of the outer member 450 allows the head receiving orifice 820 to expand to a diameter larger than the maximum diameter 126 of the pedicle screw head 110.

Figure 12A:
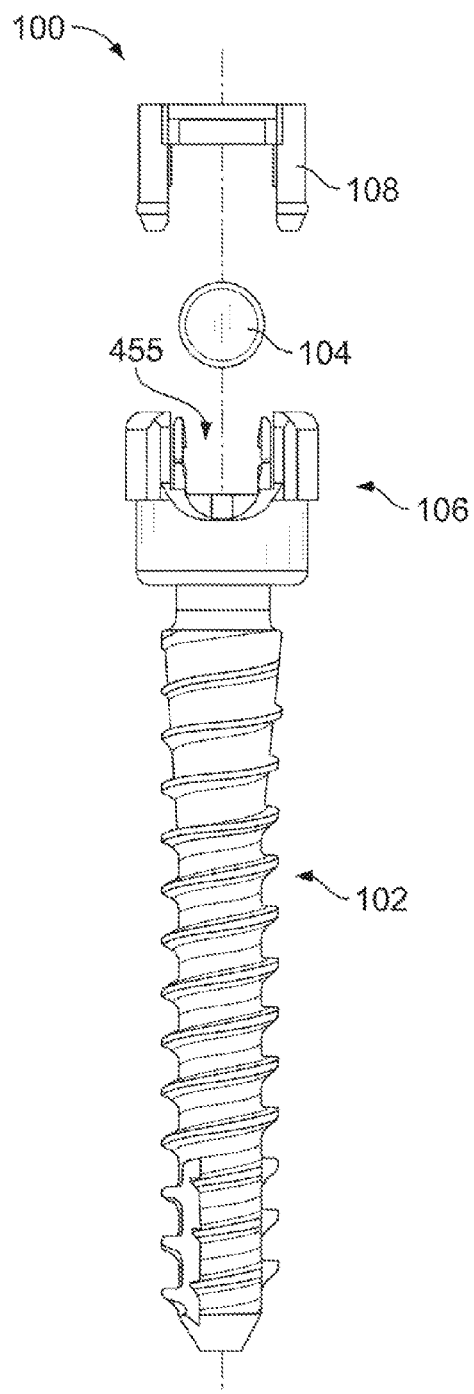
FIGS. 12A and 12B are an exploded front view and a cross-sectional perspective view, respectively, of the components of the pedicle screw system of FIG. 10 with the assembly coupled to a head of a pedicle screw, according to one exemplary embodiment.
Figure 12B:
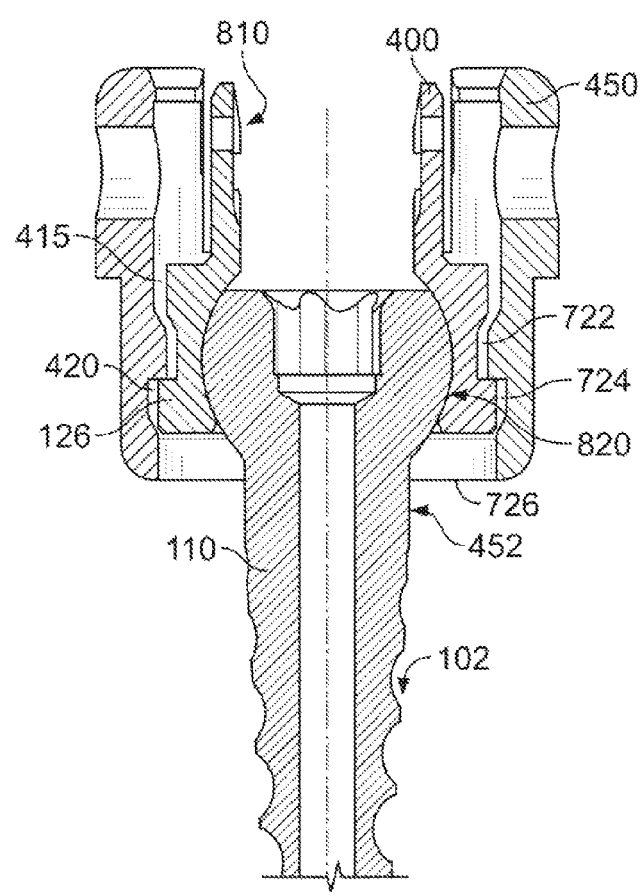

With the coupling assembly 106 in position, the screw head is snapped into the head receiving orifice 820, as illustrated in FIGS. 12A and 12B. According to one exemplary embodiment, the coupling assembly 106 may be intra-operatively (i.e., during surgery) coupled to the head portion 110 of the pedicle screw 102 and may be maneuverable to achieve a desired placement, orientation, and/or angular position of the coupling assembly 106 relative to the pedicle screw 102. Alternatively, the coupling assembly may be coupled to the head of the pedicle screw before surgery, or the insert member 400 may be coupled to the pedicle screw before the insert member 400 is coupled to the outer member 450.

According to one exemplary embodiment, when the coupling assembly 106 is snapped onto the head portion 110 of the pedicle screw 102, the head portion 110 of the pedicle screw 102 passes through the thru-bore 452 and engages the lower portion of the insert member 400. As the coupling assembly 106 is pushed onto the head portion 110 of the pedicle screw 102, the lower portion of the insert member 400 expands, due in part to the expansion gap 810 and snaps onto the head portion 110. The annular expansion groove 724 in the lower portion of the outer member 450 permits the expansion and contraction of the insert member 400. Once the head portion 110 of the pedicle screw 102 is received in the head receiving orifice 820, the insert member 400 compresses about the head portion of the pedicle screw. At this point of the installation method, the coupling assembly 106 may be pivotably coupled to the head portion 110 of the pedicle screw 102.

Figure 13A:
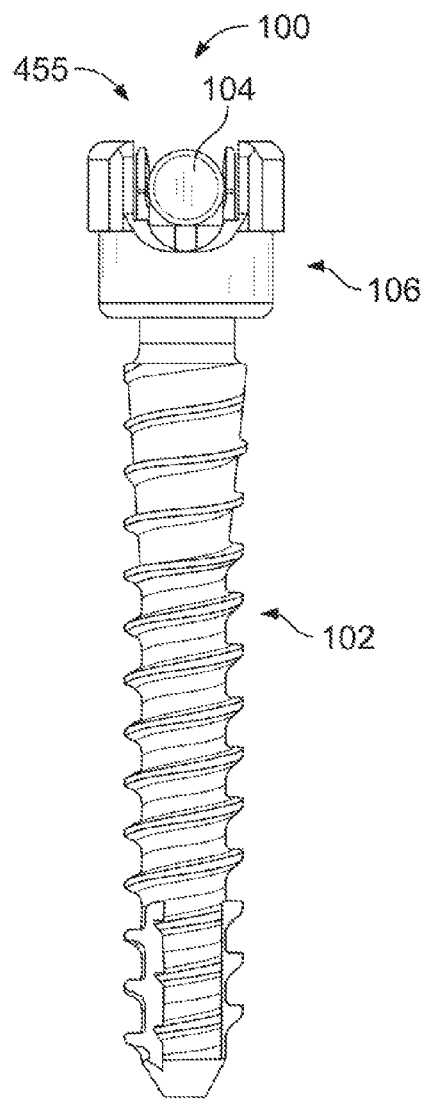
FIGS. 13A and 13B are a front view and a cross-sectional perspective view, respectively, of the components of the pedicle screw system of FIG. 10 as a rod is snapped into the insert member, according to one exemplary embodiment.
Figure 13B:
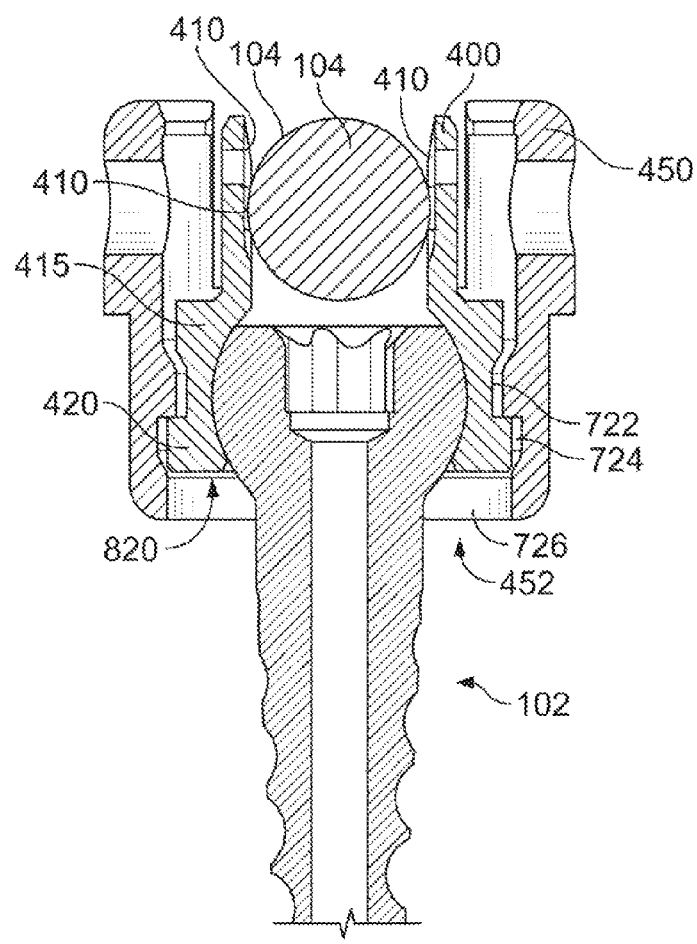
Figure 14A:
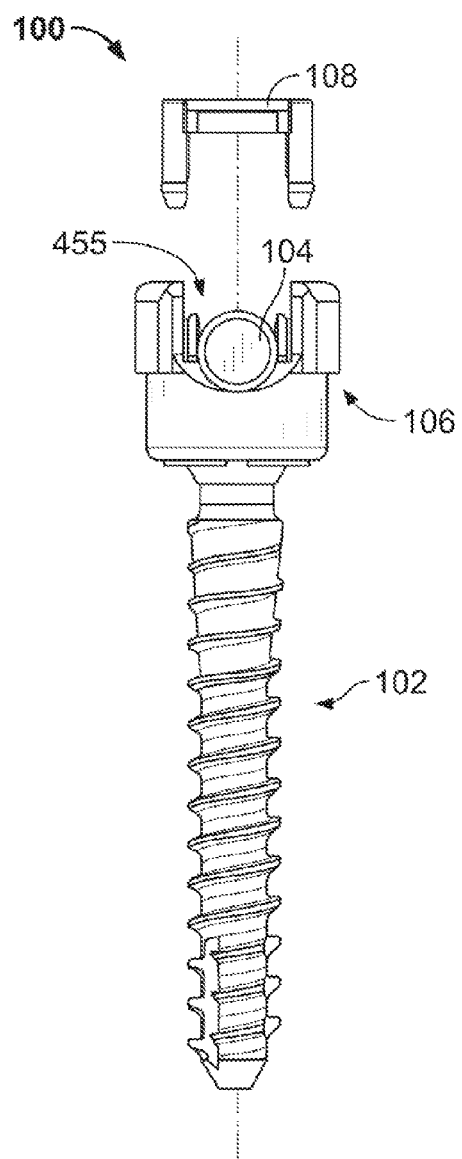
FIGS. 14A and 14B are a front view and a cross-sectional perspective view, respectively, of the components of a pedicle screw system during provisional lock of the assembly with respect to the pedicle screw, according to one exemplary embodiment.
Figure 14B:
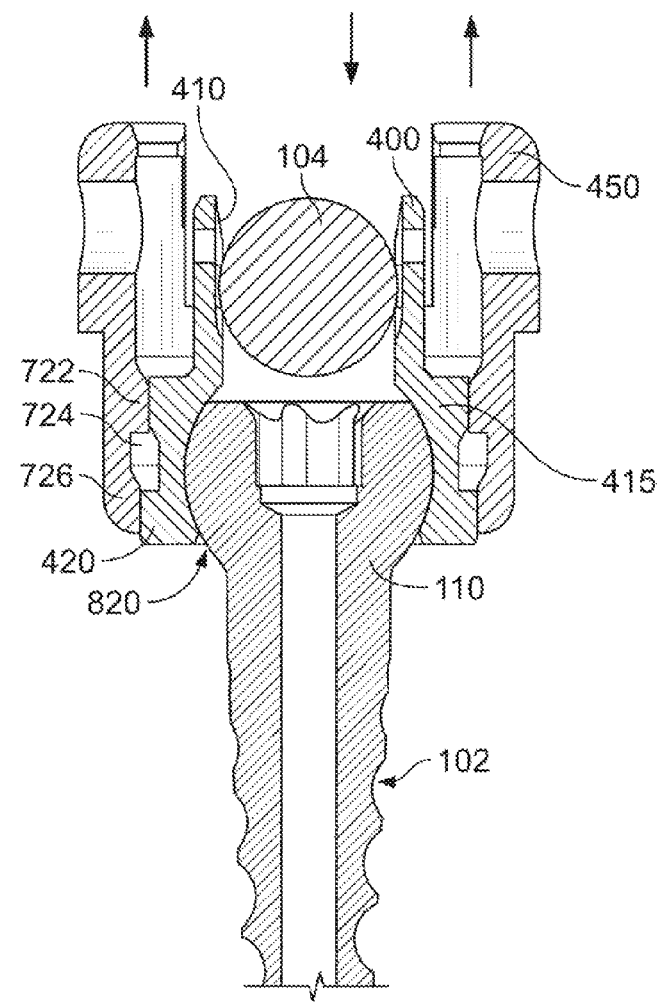

With the coupling assembly snapped over the head of the pedicle screw, a rod 104 may be inserted into the rod recess 455 of the insert member (step 1020). According to one exemplary embodiment, the rod 104 can be snapped into the insert member 400 either before or after provisional locking of the coupling assembly 106. As illustrated in FIGS. 13A and 13B, both the outer member 450 and the insert member 400 are aligned to receive the rod 104. According to one exemplary embodiment, the rod recess 455 and the insert member 400 are specifically sized to receive the rod 104 without significant interference. Specifically, the rod retention arms 800 are positioned substantially parallel with the rod recess 455 such that a clear channel to receive the rod 104 is established. During insertion of the rod to the coupling assembly 106, the rod retention arms 800 may expand to receive the rod 104. Once the rod 104 is received, the rod engagement ridges 410 of the arms establish additional points of contact on the rod. This is advantageous because it allows the frictional contact points on the rod 104 to be distributed about the perimeter of the rod, rather than having minimal contact points on the arms. It will be understood that the coupling assembly 106 may be fixed to the pedicle screw 102 at various stages of the present exemplary installation of the pedicle screw system 100. In one exemplary embodiment, the coupling assembly 106 is fixed onto the pedicle screw 102 before the rod 104 is fixed or locked into the coupling assembly. In another embodiment, the coupling assembly 106 is fixed onto the pedicle screw 102 contemporaneously as the rod 104 is fixed or locked into the coupling assembly. For ease of explanation, the present method will continue to be described according to the exemplary method illustrated in FIG. 10.

With the rod 104 inserted in the coupling assembly (step 1030, FIG. 10) position of the coupling assembly may be oriented as desired relative to the pedicle screw (step 1030). Specifically, when the desired orientation is established, the coupling assembly position relative to the pedicle screw may be locked by positioning the insert member relative to the outer member 450. Locking can be obtained by either pulling up on the outer member 450 and/or pushing down on either the rod 104 or the insert member 400, as illustrated by the arrows in FIGS. 14A and 14B. Locking is obtained by shifting of the outer member relative to the insert member to create an interference fit between the proximal locking feature 415 and the distal locking feature 420 of the insert member 400 and the proximal annular compression feature 722 and the distal annular compression feature 726 of the outer member 450, respectively. When these mating features are engaged, the head receiving orifice 820 of the insert is compressed about the head portion 110 of the pedicle screw 102.

It is understood that the relative angular position of a first coupling assembly 106 to a first pedicle screw 102 may be different from the relative orientation of other pedicle screw systems located elsewhere on a patient's spine. In general, the relative, angular position of the coupling assembly 106 to the pedicle screw 102 allows the surgeon to selectively and independently orient and manipulate the coupling assemblies 106 of each pedicle screw system 100 installed into the patient to achieve and/or optimize the goals of the surgical procedure, which may involve compressing, expanding, distracting, rotating, reinforcing, and/or otherwise correcting an alignment of at least a portion of a patient's spine. According to one exemplary embodiment, when the proximal locking feature 415 and the distal locking feature 420 of the insert member 400 are engaged with the proximal annular compression feature 722 and the distal annular compression feature 726 of the outer member 450, respectively, the frictional force exerted on the head portion 110 of the pedicle screw 102 is maintained, locking the assembly in a desired position with respect to the screw.

Figure 15A:
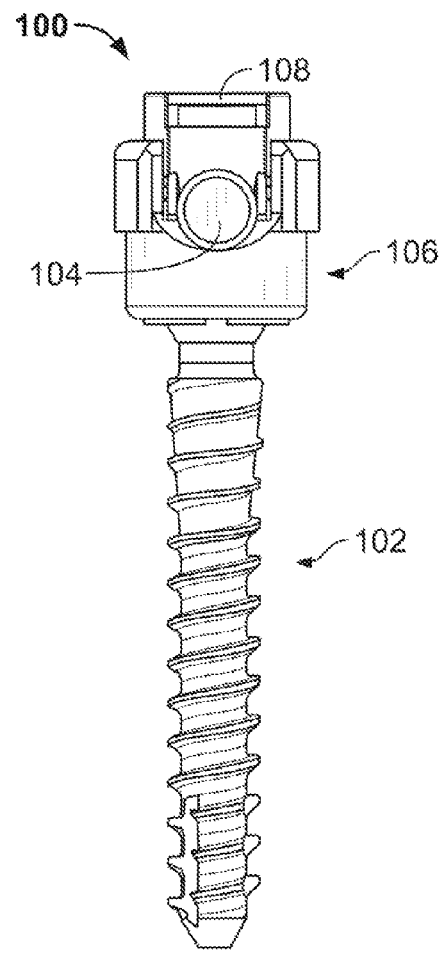
FIGS. 15A and 15B are a front view and a cross-sectional perspective view, respectively, of the components of a low top pedicle screw system as a compression cap is snapped into place, according to one exemplary embodiment.
Figure 15B:
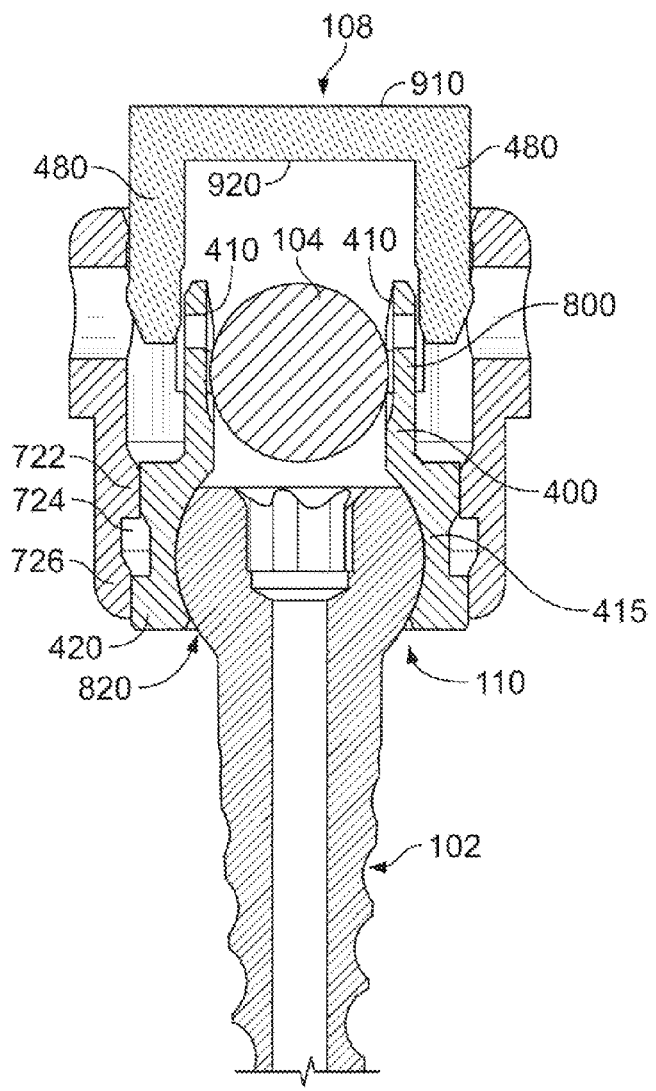

With the assembly position relative to the pedicle screw established due to the positioning of the insert member 400, the compression cap 108 may be snapped into the assembly to retain the rod (step 1050). As illustrated in FIGS. 15A and 15B, the compression cap 108 is snapped into the coupling assembly 106 but is not fully seated. According to one exemplary embodiment, the partial insertion of the compression cap 108 fills in the gap between the rod retention arms 800 of the insert member 400 and the outer member 450, preventing the insert member from expanding. Consequently, the rod 104 is retained within the insert member 400 and the outer member 450 by an increased pressure or frictional force being applied at the interface between the rod engagement ridges 410 and the rod 104.

Figure 16A:
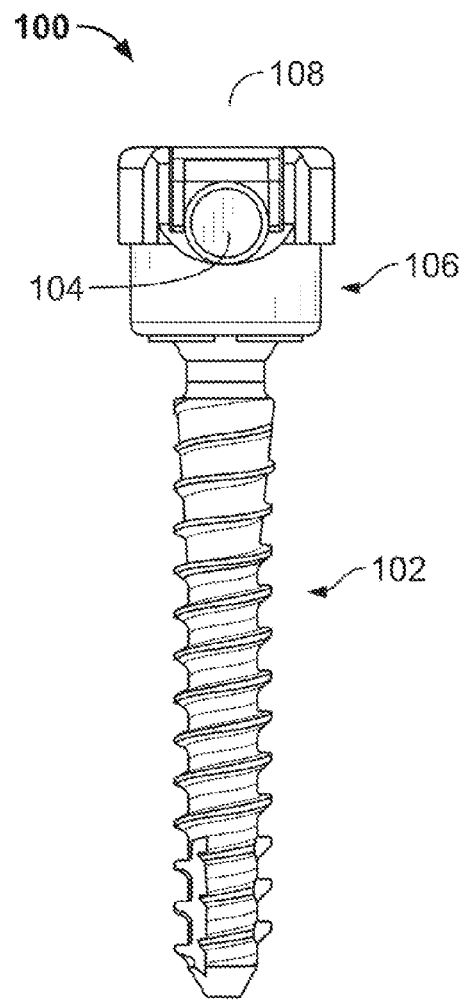
FIGS. 16A and 16B are a front view and a cross-sectional front view, respectively, of the components of a pedicle screw system in a fully assembled position, according to one exemplary embodiment.
Figure 16B:
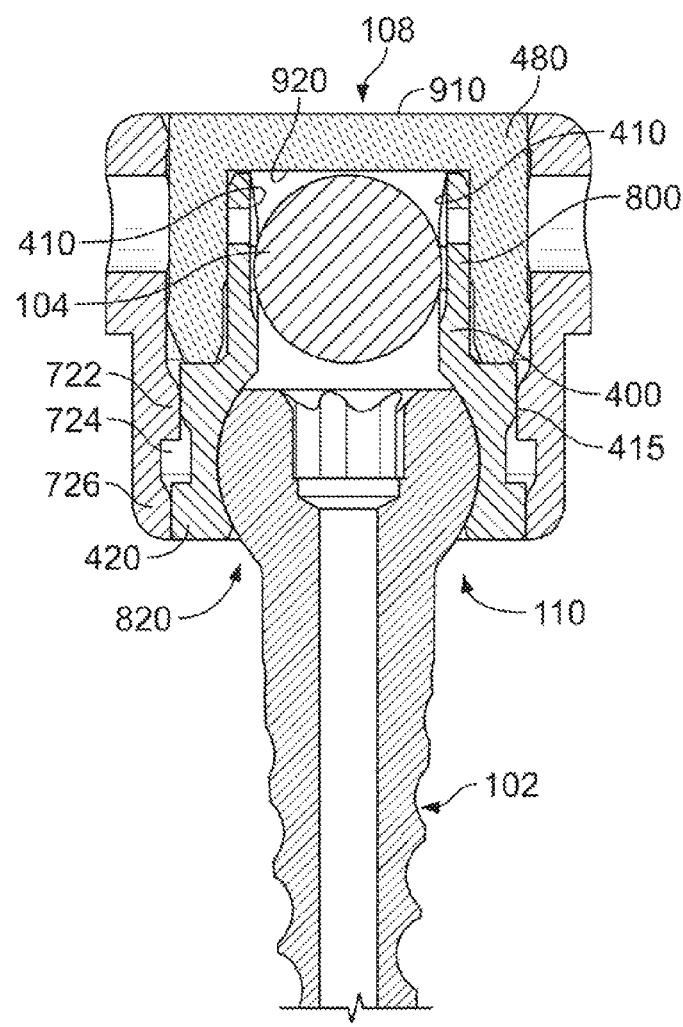

When the positioning of all of the related components is confirmed, complete insertion of the compression cap 108 may be performed for a final lock of the rod (step 1060). Particularly, as illustrated in FIGS. 16A and 16B, according to one exemplary embodiment, completely seating the compression cap 108 compresses the rod retention protrusions 800 of the insert member 400 to grip the rod 104. Additionally, according to one exemplary embodiment, the insertion of the compression cap 108 may prevent the outer member 450 from splaying open under operative and post-operative dynamic and static loading, for example. Splaying is prevented due to the material that is coupled up and over the rod 104 by the compression cap 108.

As illustrated in the exemplary embodiment of FIGS. 16A and 16B, when the compression cap is fully inserted, the rod 104 is forced into substantially full engagement with the insert member 400 and outer member 450, with further downward translation prevented by the rod stop 710 of the outer member 450. Consequently, the resistive force exerted against the rod 104 increases the frictional resistance provided by the rod engagement ridges 410 to prevent the rod from slideably translating within the coupling assembly 106. According to one exemplary embodiment, the insertion of the compression cap 108 may be performed by inserting an instrument over the compression cap and forcing it downward into the assembly.

During operation, the exemplary pedicle screw system as illustrated in FIGS. 1-16B is designed for fixation of bone material and/or bone segments during a surgical procedure, such as fusing spinal segments in which MIS techniques are employed. For example, according to one exemplary embodiment, pedicle screws with coupling members are inserted into the pedicles of a patient's spine and then the coupling members are interconnected with rods to provide support to the spine, allowing for post-operative fusion of the spinal segments. While the pedicle screw can be inserted with the coupling assembly coupled with the pedicle screw, one embodiment for the installation of the pedicle screw system includes inserting the pedicle screw into the bone and subsequently coupling the coupling assembly to the pedicle screw, where such an approach has advantages over currently known pedicle screw system assemblies and/or installations.

In addition, various structural features of the pedicle screw system as described, but not limited to the embodiments herein, may provide other advantages over existing pedicle screw systems. First, the pedicle screw may be inserted into the bone of a patient without the presence of the coupling assembly or rod, which permits the surgeon to place the screw and then perform subsequent inter-body work without having to work around the coupling assembly or the rod. Second, the coupling assembly includes a mechanism for capturing the rod that eliminates problems associated with conventional pedicle screws, such as cross-threading, because the exemplary pedicle screw systems disclosed herein do not use any threads or other elements requiring a rotatable cap member to couple the coupling assembly to the rod and pedicle screw. Third, the interface between the head portion of the pedicle screw and the coupling assembly provide an initial lock, which allows the angle of the coupling assembly to be set or fixed with respect to the pedicle screw before insertion of the rod and/or before the rod is captured in the coupling assembly. With this type of pedicle screw system, the surgeon has the ability to check and even double check the placement, angle, and/or orientation regarding aspects of the pedicle screw system to facilitate, and even optimize, the compression, distraction, and/or other manipulation of the spinal segments. In contrast, many prior art pedicle screw assemblies are designed such that a cap member designed to secure the rod in place also acts to force the rod downward onto the head of a pedicle screw, clamping the screw head against a bottom surface of the assembly and locking the position of the screw simultaneously with locking the position of the rod. A disadvantage of these prior art pedicle screw systems is that the assembly pivots freely upon the head of the pedicle screw until the rod is secured in the assembly and locked into place against the screw head. In the present system, the cap and outer member may be shifted simultaneously in order to simultaneously lock the screw and rod into position, but the screw may also be locked into position prior to the rod being received in the coupling assembly.

One possible post-operative advantage of the present exemplary pedicle screw system is that the cooperation and interaction of the insert member 400 with the compression cap 108 substantially reduces, and most likely prevents, the known problem of the assembly splaying. Assembly splaying is generally regarded as a post-operative problem caused by a stressed rod forcing open portions of the outer member, which eventually leads to the disassembly and likely failure of the pedicle screw system within the patient.

Yet another post-operative advantage of the pedicle screw systems is that unlike existing rod-coupling members or constructs, the exemplary coupling assemblies described herein have a smaller size envelope (e.g., are less bulky, have a lower profile, and/or are more compact in shape) and are easier to place onto the pedicle screw when compared to traditional systems. The smaller size and ease of installation may reduce trauma to the soft-tissue regions in the vicinity of the surgical site, which in turn generally allows for a quicker recovery by the patient. According to aspects described herein, and as appended by the claims, the present exemplary pedicle screw systems permit insertion of the pedicle screw without the coupling assembly coupled thereto, locking the coupling assembly onto the pedicle screw, and subsequently capturing and locking the rod into the assembly.

Exemplary Additional Screw Retention Features Illustrated in FIGS. 17-25

In addition to the general structure and function described, and exemplary embodiments thereto, it is desirable in some circumstances to implement additional features to strengthen the mating relationship between the coupling assembly and the pedicle screw or other anchor member prior to final locking, since after implantation it is often necessary to apply significant amounts of force in order to rotate and shift the coupling assemblies into alignment with each other or into alignment with spinal rods. Retention features may be added to prevent the screw head from escaping the cavity in the lower portion of the coupling assembly when in a provisional screw lock position prior to full screw locking, allowing the coupling assembly to be pivoted about the screw head but preventing the screw head from separating from the coupling assembly.

Figure 17A:
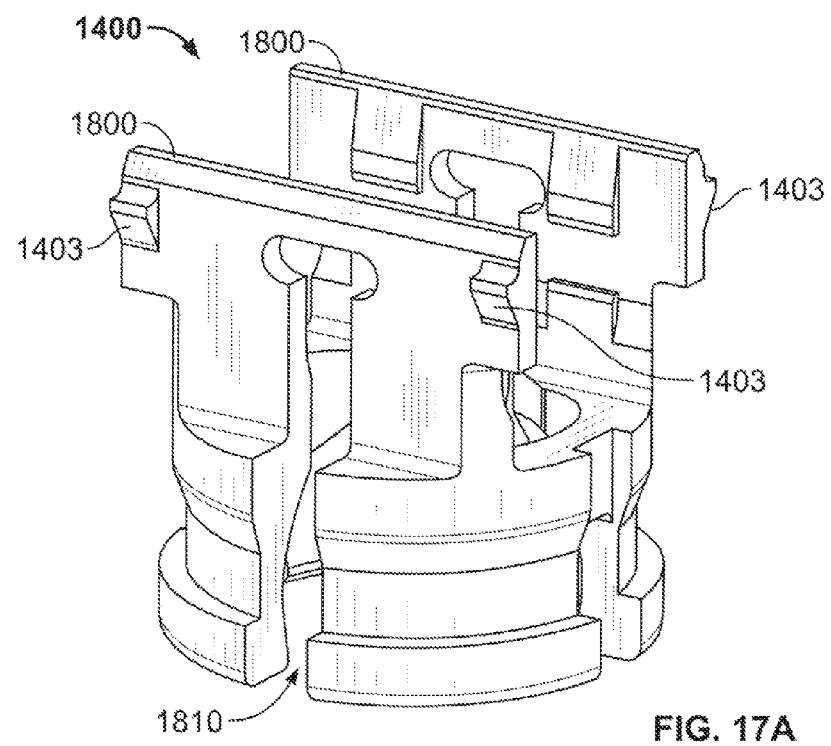
FIG. 17 is a perspective view of one exemplary embodiment of an insert member with retention features to limit axial shifting of the insert member with respect to an outer member.
Figure 17B:
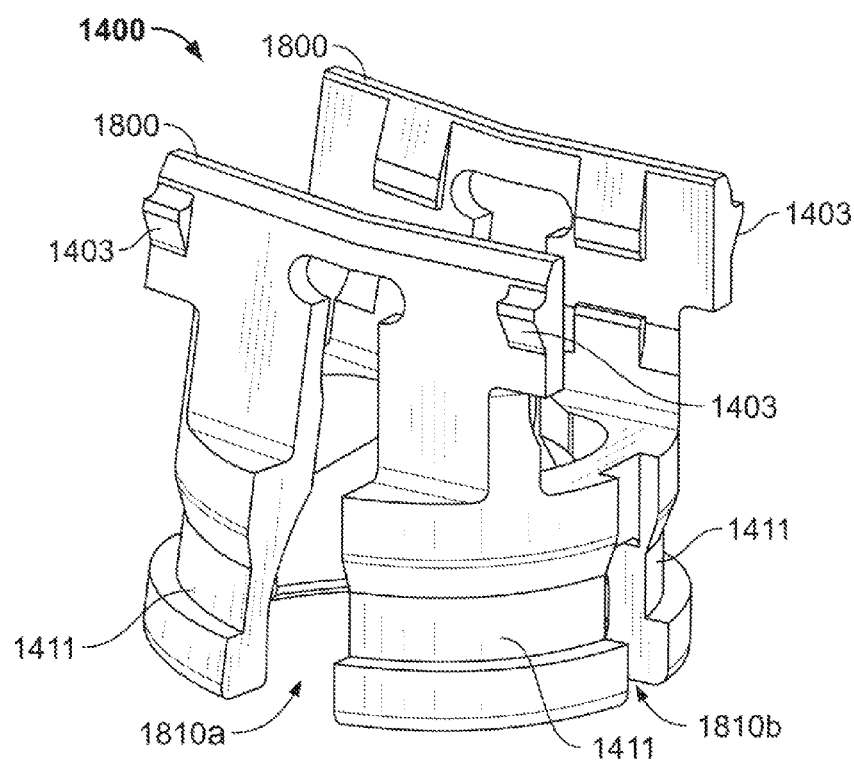

In one form, the insert member and outer member may be provided with features to limit axial or other linear movement with respect to each other prior to full locking, allowing for one-way locking of the insert member and outer member and preventing the insert member from backing out of the outer member once inserted to a predetermined position. For example, the embodiment depicted in FIGS. 17-21 has one-way retention elements in the form of outwardly-extending inclined retention tabs 1403 on the insert member 1400 (FIGS. 17A-B) and complementary inwardly-extending inclined retention tabs 1453 on the outer member 1450 (FIG. 18). The outer member retention tabs 1453 are positioned to engage the inner member retention tabs 1403 when the inner member shifts axially within the outer member 1450. As shown in one exemplary embodiment in 17A, the insert tabs 1403 may protrude from the flexible arms 1800 of the rod-retaining portion of the insert. In this position, the tabs do not shift inward as portions of the annular wall 1411 of the lower portion flexes, as shown in FIG. 17B, since the flexible arms 1800 are transverse to the major expansion gaps 1810a primarily responsible for flexion of the annular wall portions 1411 and expansion of the cavity formed thereby. Minor expansion gaps 1810b in the annular wall 1411 of the insert 1400 have a shorter length in the axial direction than the major expansion gaps, and therefore do not provide for the same amount of flexion of the annular wall 1411 as the major expansion gaps 1810a.

Figure 19A:
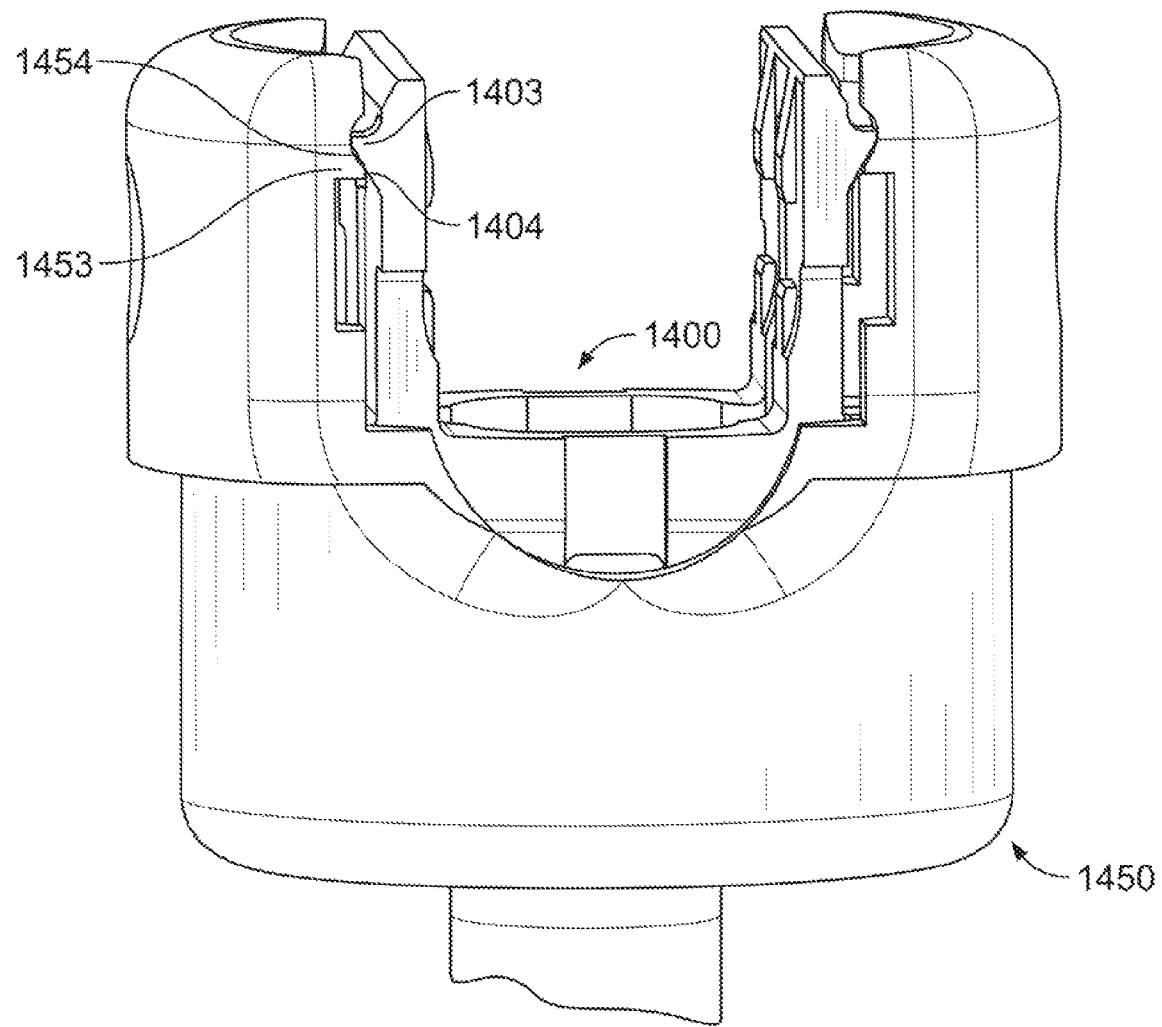
FIGS. 19A and 19B are a front view and a front cross-sectional view, respectively, of the coupling assembly of FIGS. 17 and 18, and retention features thereof, in a screw-receiving configuration.
Figure 19B:
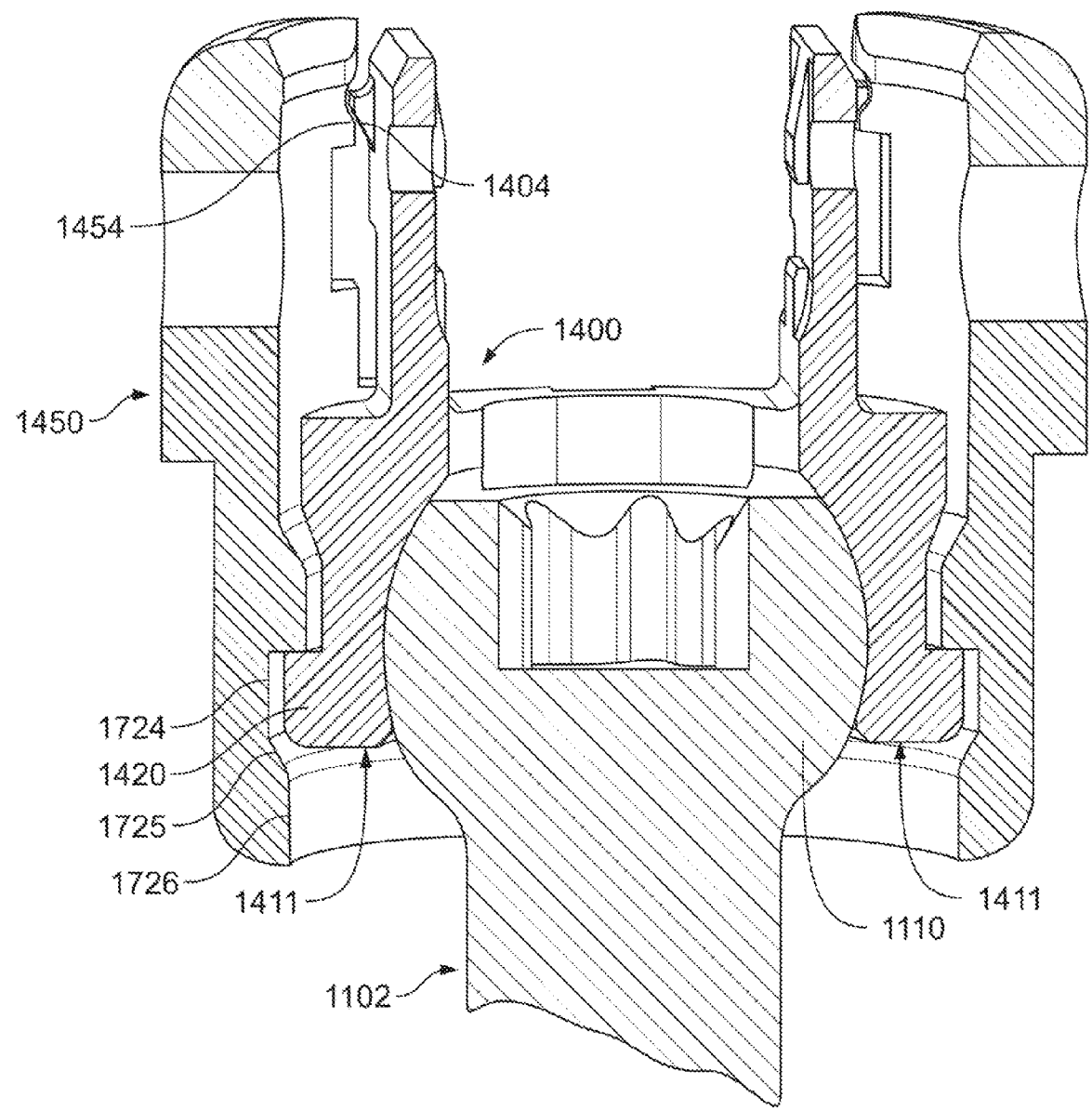

The insert 1400 is shown in FIGS. 19A-B in an initial position within the internal space of the outer member 1450, wherein the retention tabs 1403 on the insert and retention tabs 1453 on the outer member do not interfere with one another. Downward-facing inclined surfaces 1404 of the insert 1400 are facing toward complementary upward-facing inclined surfaces 1454 on the outer member 1450. As shown in FIG. 19B, when the annular flange or locking feature 1420 of the insert member is positioned within the annular groove 1724 of the outer member, a sufficient amount of force will dislodge screw head 1110 from the insert member by shifting the annular wall portions 1411 of the insert member 1400 outward, creating an opening large enough for the screw head 1110 to escape. Consequently, the insert member 1400 and outer member 1450 may be pre-assembled in this position, and the pedicle screw 1102 may be inserted and removed from the assembly relatively easily. The locking feature 1420 of the annular wall is allowed to shift outward because it is positioned in an annular expansion recess 1724 sized to allow for expansion of the insert member.

Figure 20A:
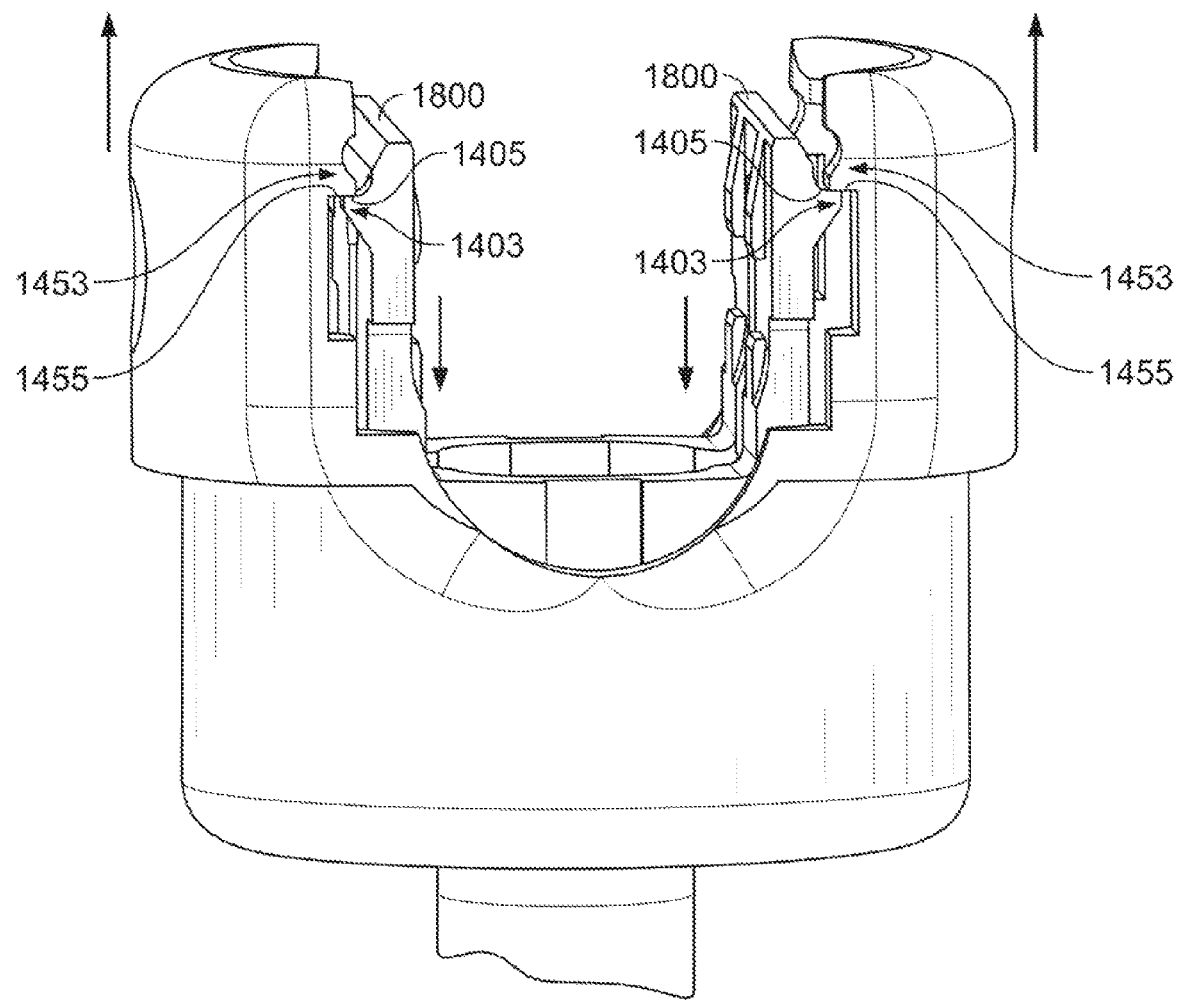
FIGS. 20A and 20B are a front view and a front cross-sectional view, respectively, of the coupling assembly of FIGS. 17-19 in a screw-retaining configuration.
Figure 20B:
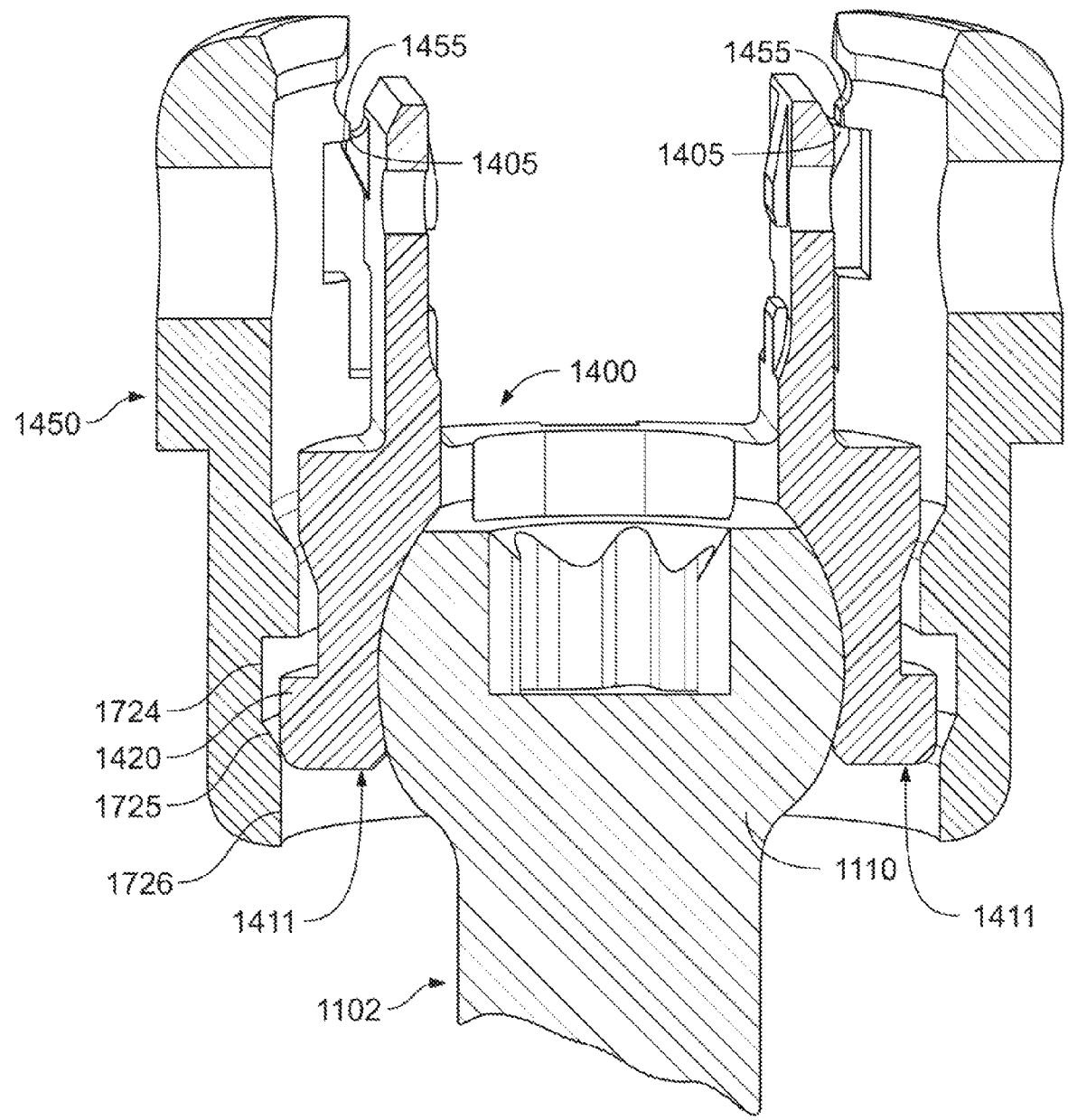

As the outer member 1450 is pulled upward relative to the insert member 1400 (so that the insert member 1400 shifts downward within the interior space of the outer member), the downward-facing inclined surfaces 1404 of the insert retention tabs 1403 engage the complementary upward-facing inclined surfaces 1454 on the outer member retention tabs 1453, and because of their complementary inclined surfaces the tabs 1403 and 1453 slide past one another. Flexible portions 1800 shift slightly inward to allow the retention tabs to slide past one another. Eventually, the insert member retention tabs 1403 are shifted to a retention position wherein the insert member retention tabs 1403 are located below the outer member tabs 1453, as shown in FIGS. 20A-B. Reaching this retention position may provide an audible click or other feedback as the insert member tabs 1403 slide past the outer member tabs 1453, allowing the flexible arms 1800 to shift slightly outward to their original positions, snapping the insert member tabs 1403 into place below the outer member tabs 1453.

In this retention position, the insert member is permitted to shift further downward into the outer member 1450, but resists shifting upward because of flat abutment surfaces 1405 and 1455 on the trailing ends of the tabs. As shown in FIG. 20B, the tabs are positioned axially along the insert member and outer member so that when the tab abutment surfaces 1405 and 1455 meet, the annular camming locking feature 1420 of the lower portion of the insert member 1400 begins to engage a locking feature 1726 inside the outer member 1450, causing the annular wall 1411 of the insert member 1400 to compress and shift slightly inward, applying a frictional force upon the screw head 1110. For instance, as depicted, a tapered cam surface 1725 leads to the locking feature 1726, causing gradual compression of the lower annular wall 1411 of the insert member 1400. In the position depicted in FIG. 20B, the compressive force exerted against the lower portion 1860 of the insert member 1400 by the tapered camming surface 1725 is sufficient to prevent the screw head 1110 from exiting the cavity formed by the annular wall 1411 of the insert member 1400, but will not fully lock the coupling assembly against pivoting with respect to the screw head 1110. The insert assembly 1400 resists backing out from this retention position due to the interaction between the abutment surfaces 1455 of the outer member tabs 1453 and the abutment surfaces 1405 of the insert member tabs 1403.

Figure 21A:
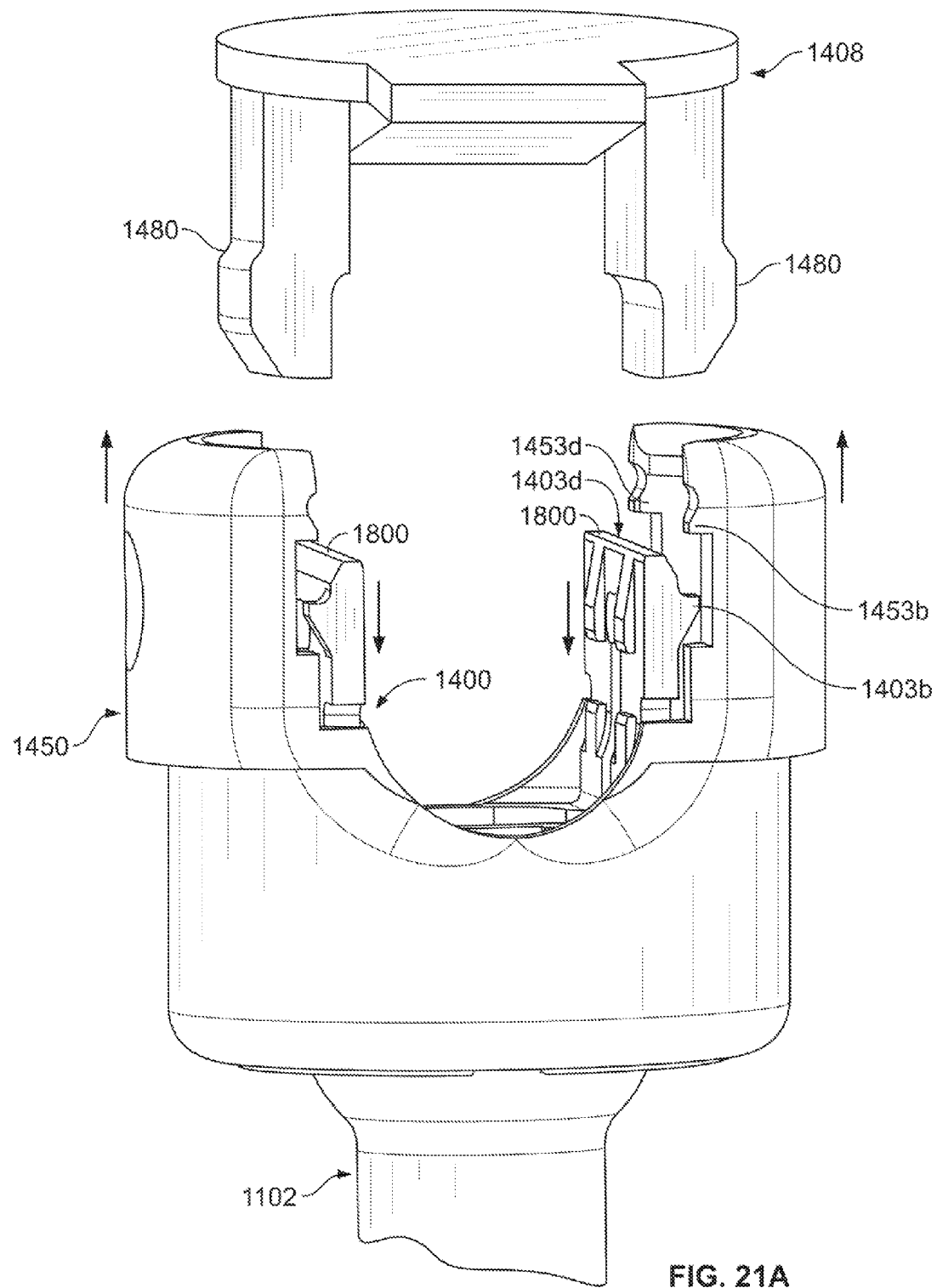
FIGS. 21A and 21B are a front view and a front cross-sectional view, respectively, of the coupling assembly of FIGS. 17-20 in a screw-locking configuration.
Figure 21B:
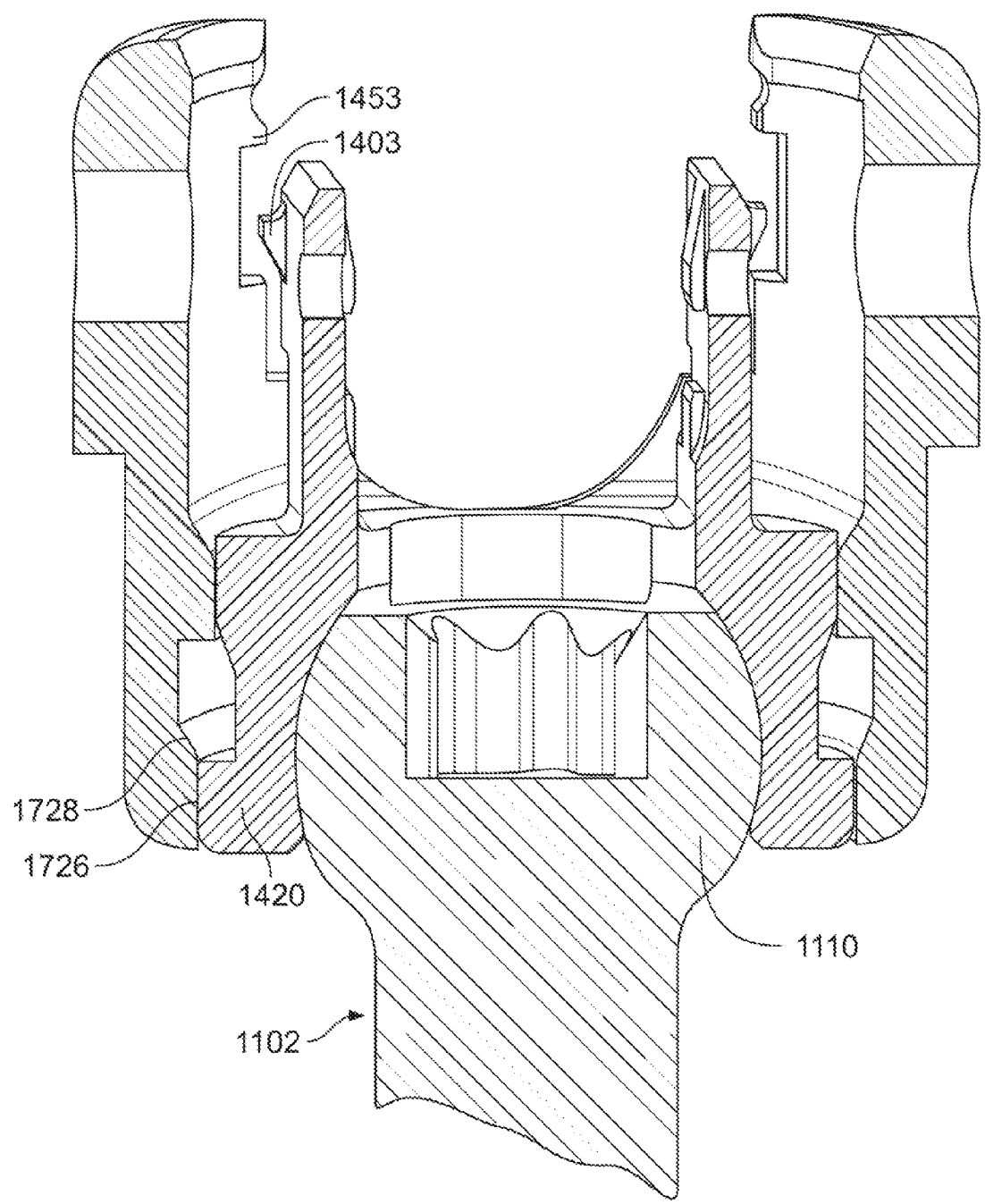

Full locking of the screw head 1110, which prevents changes in angulation between the coupling assembly 1100 and screw 1102, is achieved again by pulling upward on the outer member 1450 (further shifting the insert member 1400 downward relative to the interior of the outer member) so that the camming locking feature 1420 moves past the tapered cam surface 1725 of the outer member bore and into flush contact with the inwardly-directed face of the annular locking feature 1726 at the bottom of the bore, as depicted in FIG. 21B. In this full locking position, the insert member retention tabs 1403 are spaced below the outer member retention tabs 1453 so that the tabs no longer interact. Pairs of interacting tabs (for instance, first pair of tabs 1403b, 1453b and second pair of tabs 1403d, 1453d depicted in FIG. 21A) are spaced far enough apart in a direction parallel to the rod axis (which is generally orthogonal to the outer member axis) to allow locking portions 1480 of a rod locking device such as cap 1408 to slide axially into engagement with the flexible arms 1800 of the insert member to deflect the flexible arms 1800 inward and lock the rod in place, as previously described.

In another form, retention of the screw head prior to full locking may be enhanced by configuring the coupling assembly and screw head so that the screw head is inserted into the cavity of the insert member in one orientation and shifted or rotated to a second orientation to resist withdrawal of the screw head from the cavity. For instance, as depicted in FIGS. 22-25, a screw 2102 is provided having a head portion 2110 with a height ("h"), a first head width ("x") and a second head width ("y"), where the first head width is larger than the second head width. In this manner, the head is sized and shaped so that it may enter and exit the cavity of the insert member more easily in one orientation than in another orientation. The form of screw head depicted in FIGS. 22A-C forms essentially a truncated sphere, with a partially spherical profile when viewed from one transverse direction (FIG. 22B) and a wedge-shaped profile when viewed from a second transverse direction (FIG. 22C). This wedge shape facilitates alignment and insertion of the screw head with the opening in the insert member for snap-locking therein.

Figure 22A:
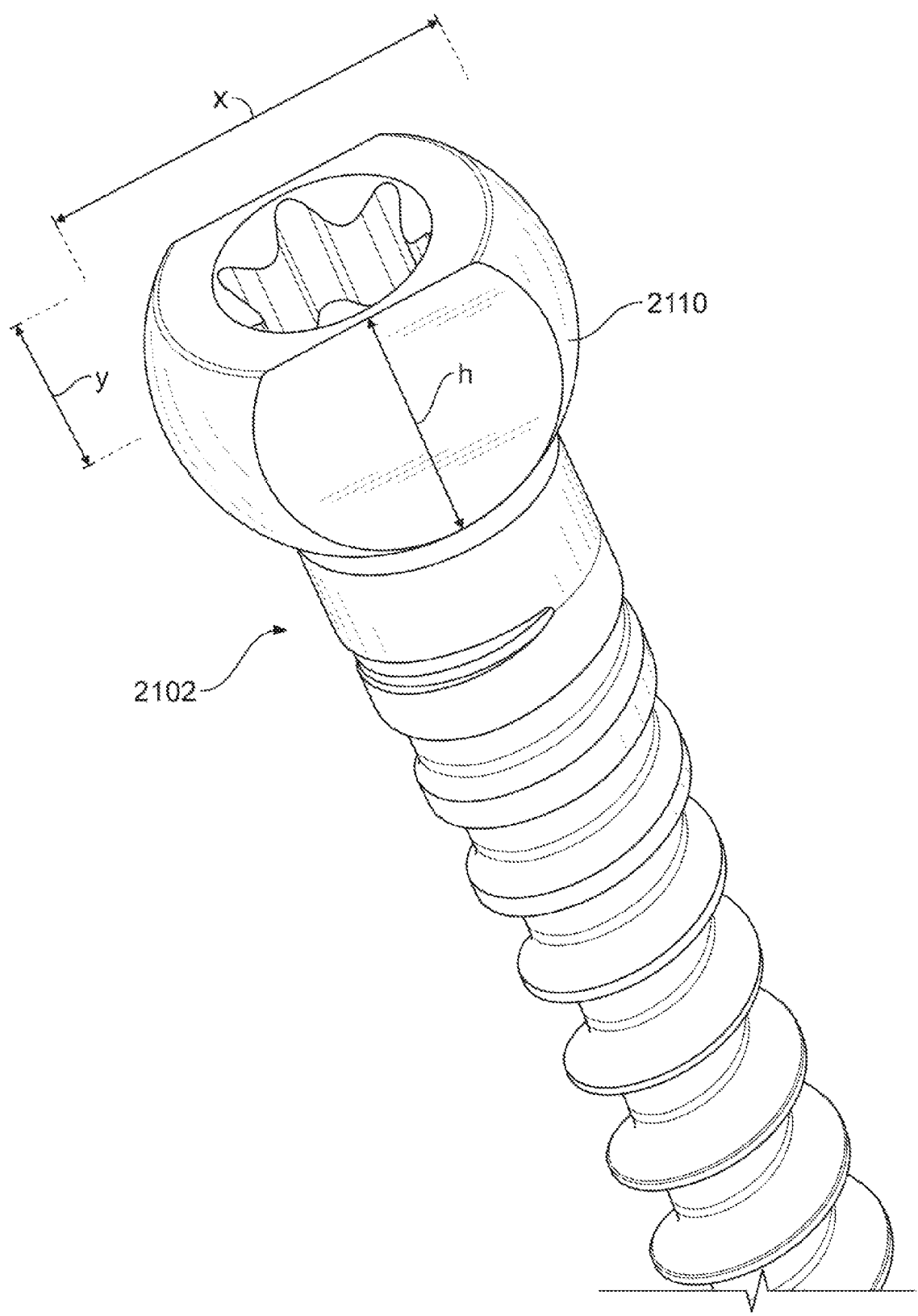
FIGS. 22A-22C are perspective views of an exemplary alternative bone anchor in the form of a pedicle screw having a truncated spherical head portion.
Figure 22B:
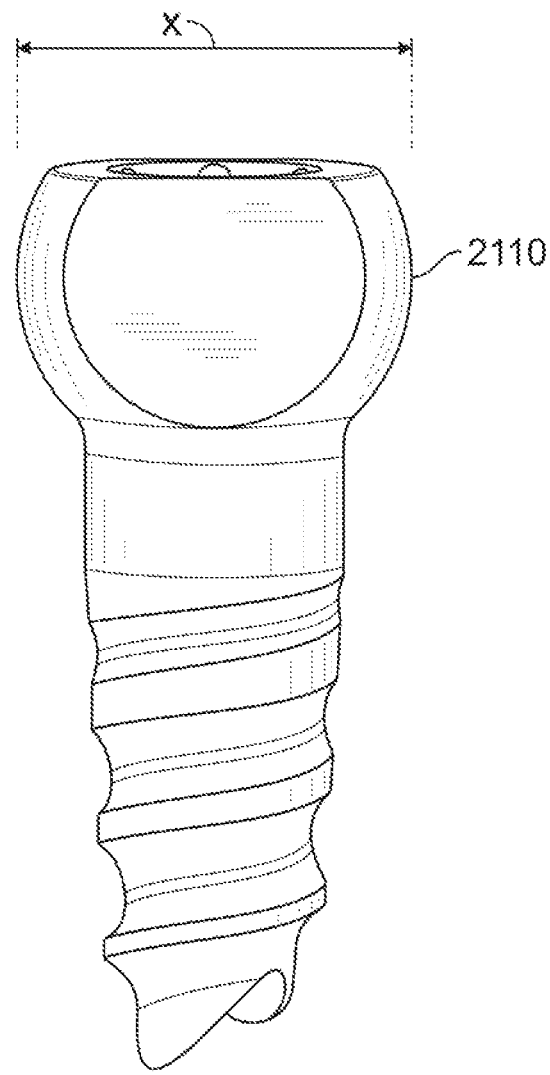
Figure 22C:
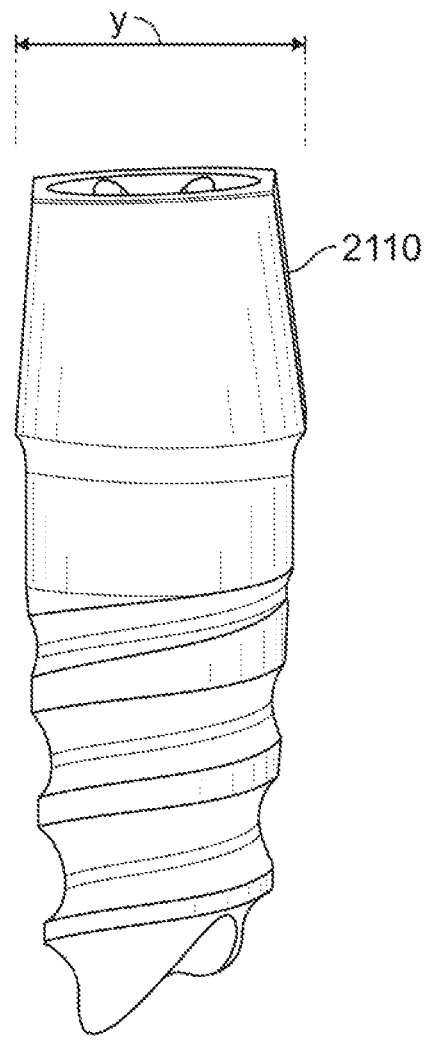
Figure 23A:
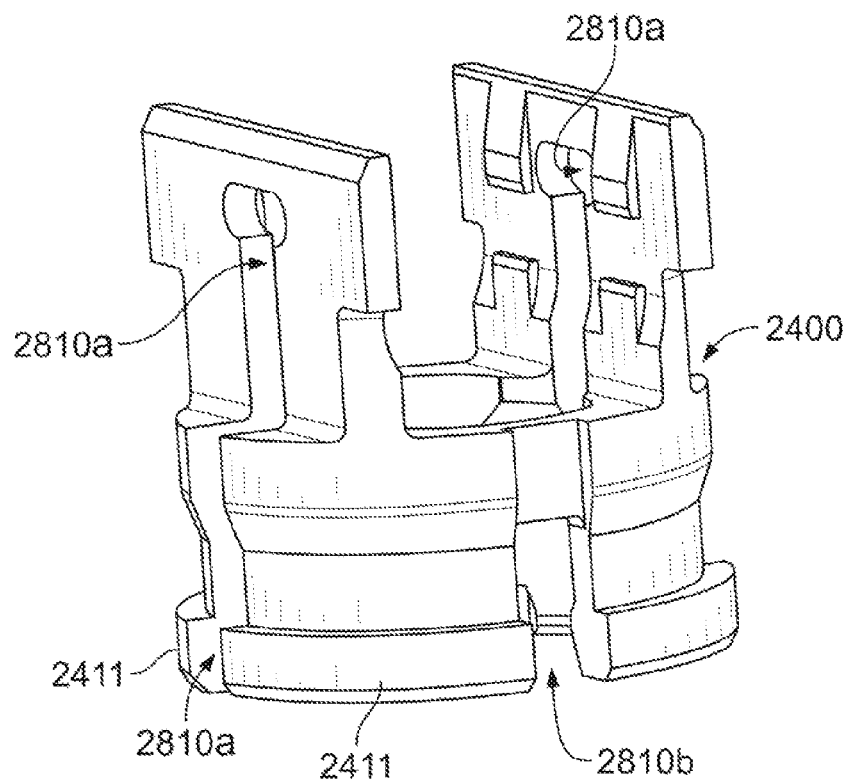
FIGS. 23A and 23B are a perspective and bottom plan view, respectively, of an exemplary insert member configured to receive the alternative bone anchor of FIG. 22.
Figure 23B:
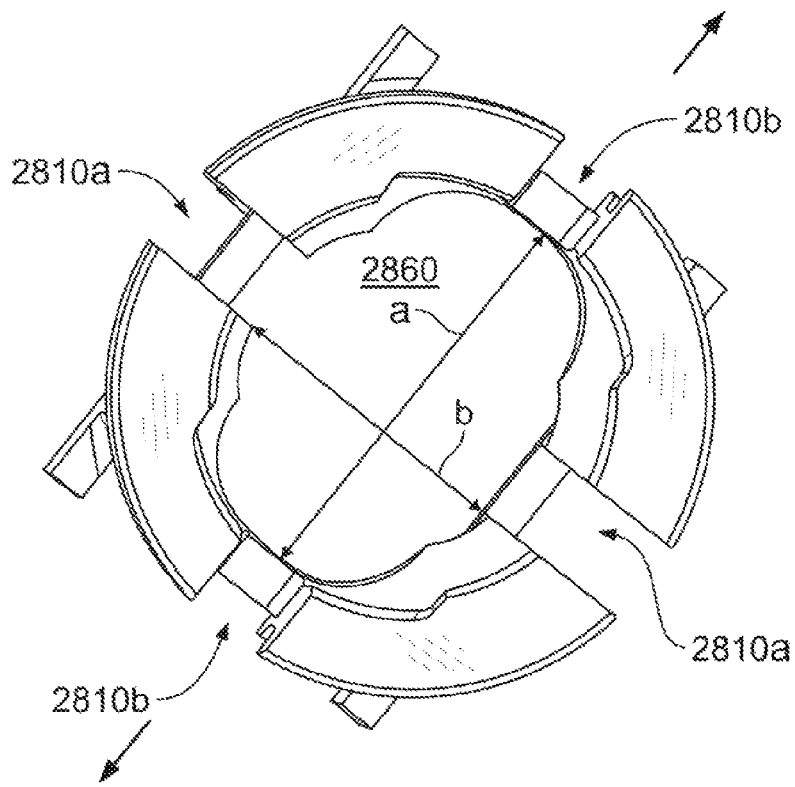

The screw head of FIGS. 22A-C is received in a complementarily configured insert member 2400, depicted in FIGS. 23A and 23B. As with other exemplary insert members described herein, the insert member includes expansion gaps 2810 for allowing the annular wall portions 2411 of the insert member to flex for receiving a screw head therebetween in a snap-lock manner. As with other embodiments, the expansion gaps 2810 also allow the annular wall portions 2411 to be compressed or compacted, applying a frictional force onto the screw head to lock it in place. Major expansion gaps 2810a allow for relatively large amounts of flexion due to their length, while minor expansion gaps 2810b permit relatively less flexion. As shown in FIG. 23B, an opening 2860 in the lower portion of the insert member is configured to receive a screw head. The opening 2860 has a first width ("a") that is larger than a second width ("b"). The first, longer width lies transverse to the major expansion gaps 2810a, so that the opening widens in the direction of the greater opening width ("a").

Figure 24A:
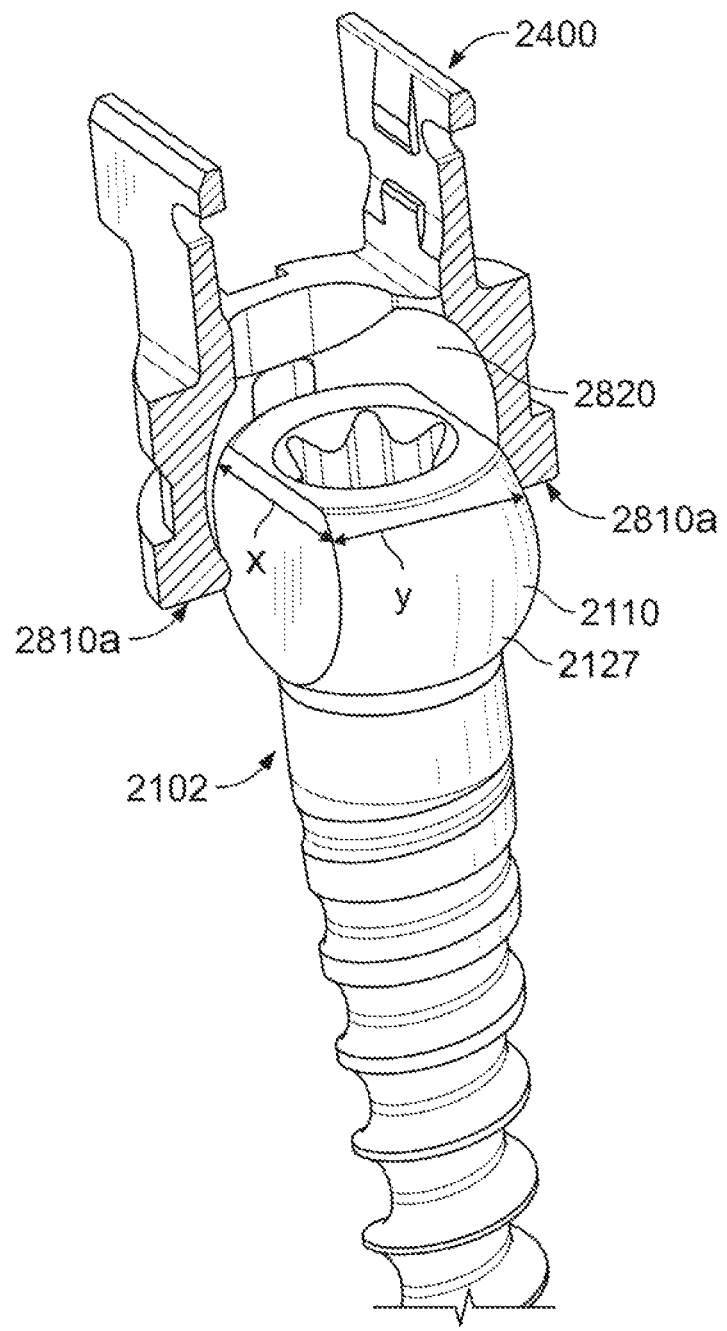
FIGS. 24A-24C depict insertion and retention of the bone anchor of FIG. 22 in the insert member of FIG. 23.
Figure 24B:
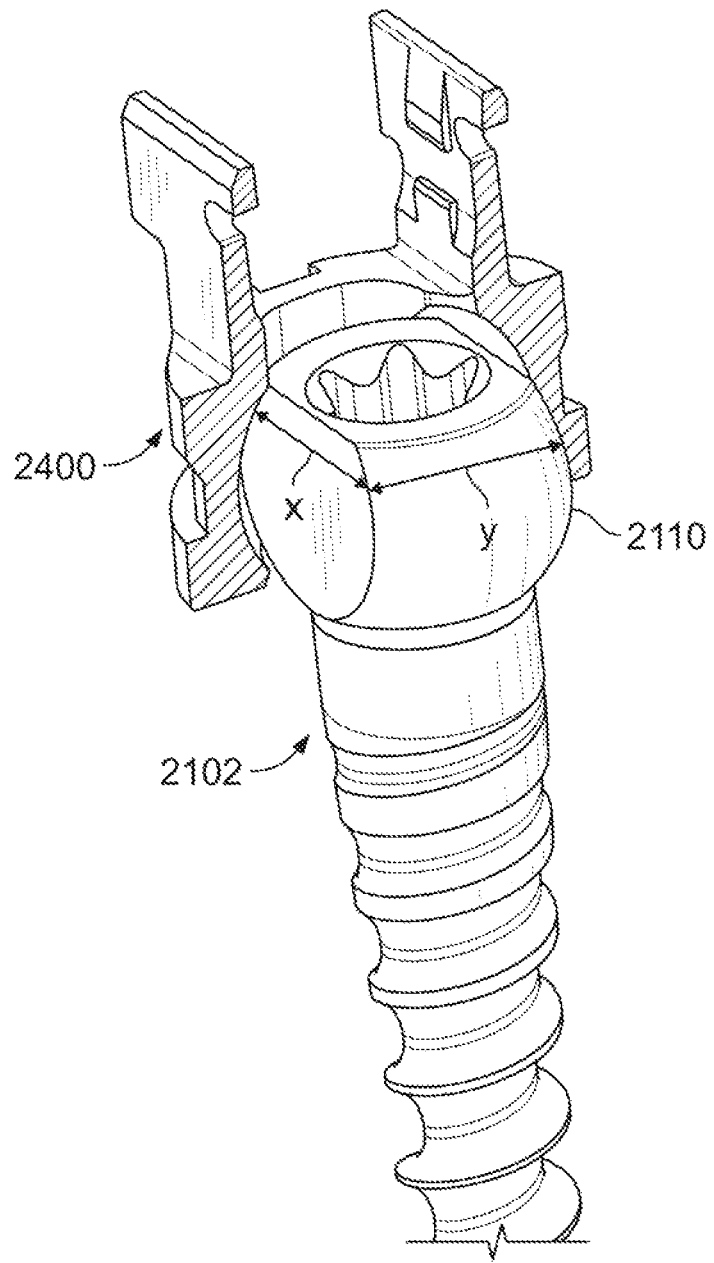
Figure 24C:
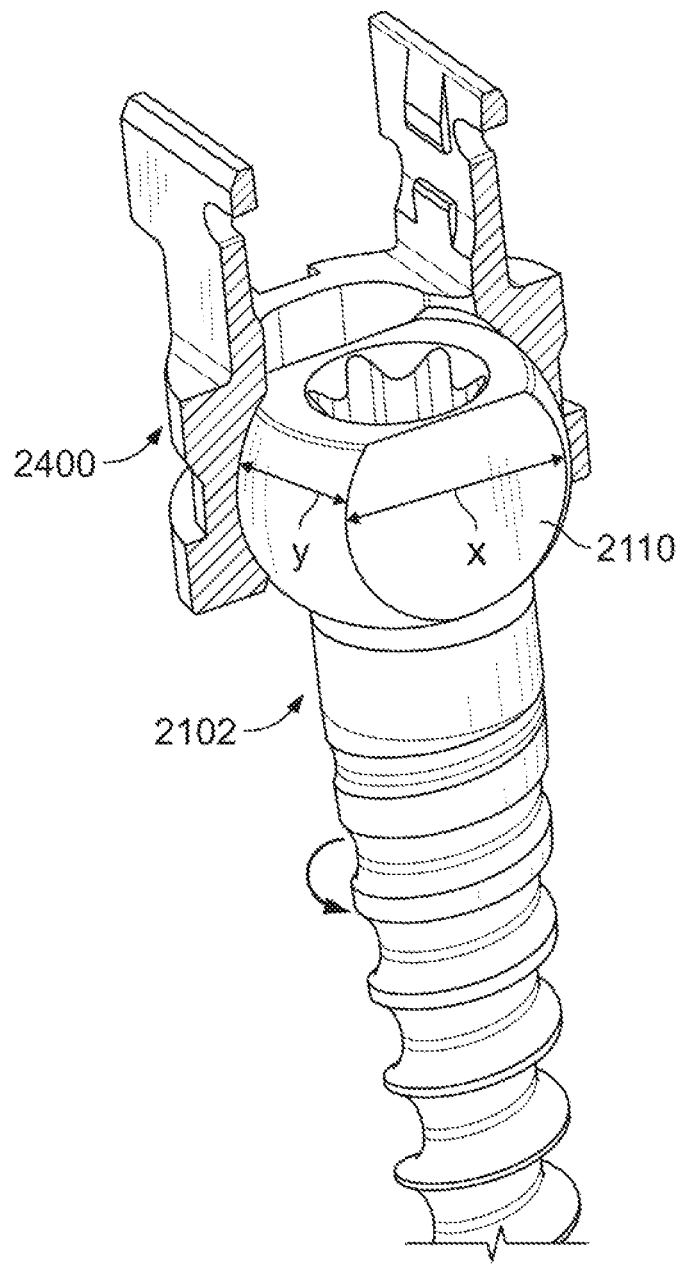
Figure 25A:
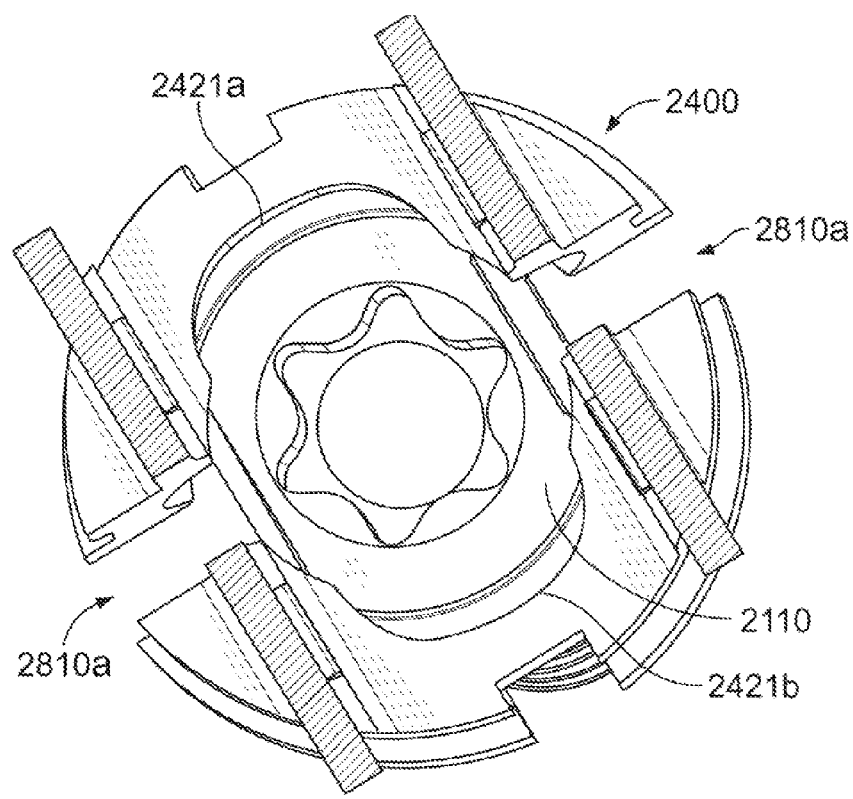
FIGS. 25A and 25B are top plan views of the insert member of FIGS. 23-24 demonstrating rotation of the bone anchor from FIG. 22 therein from an insertion position to a retention position.
Figure 25B:
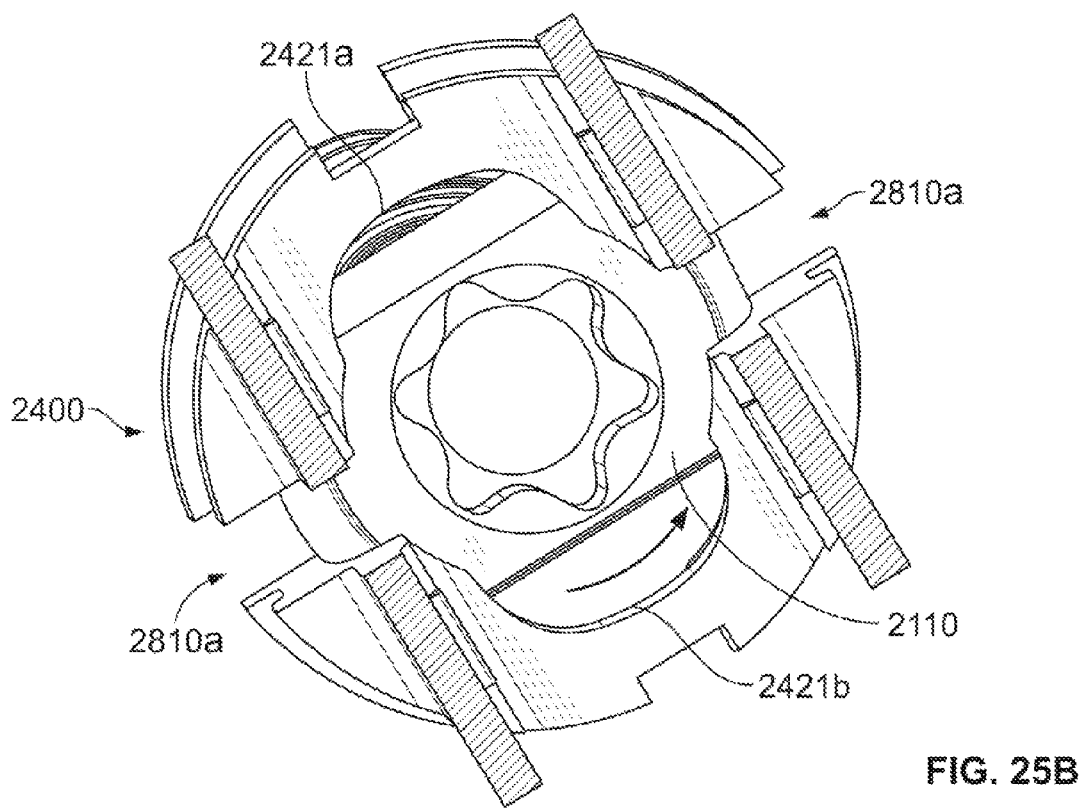

In use, the screw of FIGS. 22A-C may be inserted relatively easily into the insert member of FIGS. 23A-B when the first, larger, width of the screw head ("x") is aligned with the first, larger width ("a") of the opening 2860 in the lower end of the insert member 2400, but resists insertion from other orientations, such as when the first, larger width ("x") of the screw head is aligned with the second, narrower width ("b") of the opening in the insert member. Insertion and retention of the screw head into the insert member is demonstrated in FIGS. 24A-C, which depict a perspective view of the screw and a cut-away perspective view of the insert member 2400. Similar to other embodiments described herein, as the screw head is inserted into the cavity 2820 of the insert member 2400, as shown in FIG. 24A, major expansion gaps 2810a allow the insert member 2400 to flex, expanding the volume of the insert cavity 2820. Once the partially spherical surfaces 2127 of the head 2110 enter into the cavity, the flexible walls of the insert member flex back toward their original positions, closing around the screw head 2110 in a snap-lock arrangement. Although the insert member 2400 is at that point coupled to the screw head 2110, the insert member may still be removed with relative ease. For instance, the coupling assembly and screw head may be configured so that the coupling assembly may be removed by hand. In order to more securely hold the screw head, the insert member 2400 is rotated a predetermined amount (such as the approximately 90 degree rotation depicted) with respect to the screw 2102, so that the greater width of the insert member opening and the greater width of the screw head are out of phase, as shown in FIGS. 24c and 25B. The greater screw head width (x) is then aligned with the major expansion gaps 2810a.

Whereas the screw head 2110 contacts the annular wall portions of the insert member at points 2421a and 2421b in the insertion position (FIG. 25A), allowing the screw head to exit the insert member by expanding expansion gaps 2810a, in the retention position (FIG. 25B) the screw head 2110 does not contact wall portions 2421a and 2421b, and thus it is more difficult for forces applied to the screw or insert member to cause expansion of major expansion gaps 2810a. Thus, when the insert member is rotated to the screw retention position shown in FIGS. 24C and 25B, a greater amount of force must be applied to remove the screw head from the insert member cavity than when in the insertion position of FIGS. 24B and 25A. Advantageously, the screw head and insert member opening may be configured so that rotation of the insert member to this screw retention position ensures that the screw head will not escape the insert member cavity while the insert member is manipulated and placed under loads to engage and capture a spinal rod prior to locking of the assembly. Final locking of the screw relative to the insert member may be accomplished by axially shifting an outer member over the insert member 2400 in a manner similar to that described in connection with other embodiments herein.

Exemplary Embodiments of FIGS. 26-41 with Offset Anchor Heads for Increased Angulation Certain vertebrae of the spine are smaller than others, presenting certain difficulties during the implantation, positioning, and securing of devices intended to fix a spinal rod or other member to the spine. For instance, the cervical vertebrae (located in the neck) are much smaller than vertebrae in other portions of the spine, such as in the lumbar region. Therefore, pedicle screws or hooks mounted to the cervical spine must be positioned much closer to one another. Additionally, since the cervical region is curved, accessing the vertebrae from a posterior approach is more difficult than in other regions of the spine. Although the following embodiments are described as being particularly useful for implantation in the cervical spine, they may also be used in connection with vertebrae from other portions of the spinal column, especially where wider angulation of the anchor member is beneficial.

Figure 26:
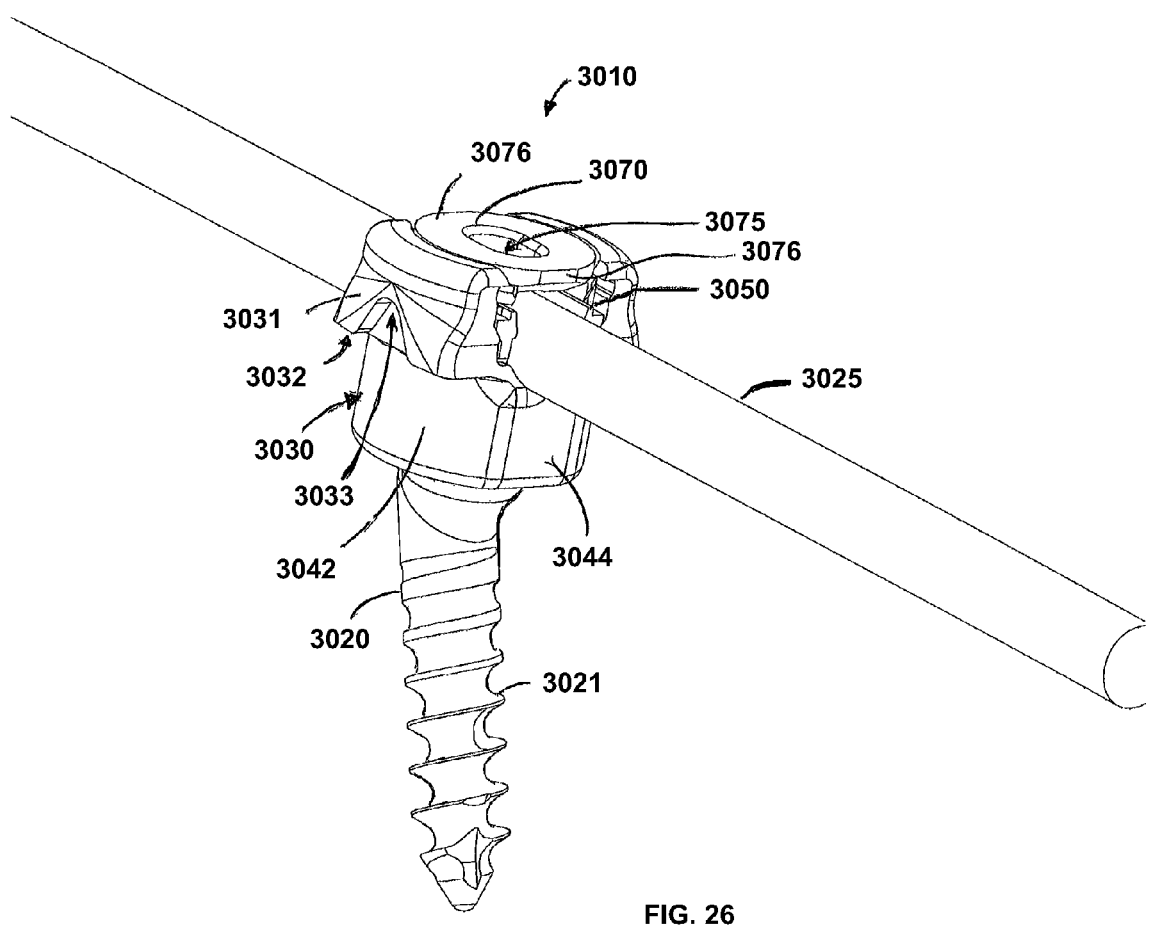
FIG. 26 is a perspective view of another exemplary polyaxial coupling assembly showing a coupling device having a shaft of an anchor member projecting out therefrom offset from the enlarged head portion in the coupling device.
Figure 27:
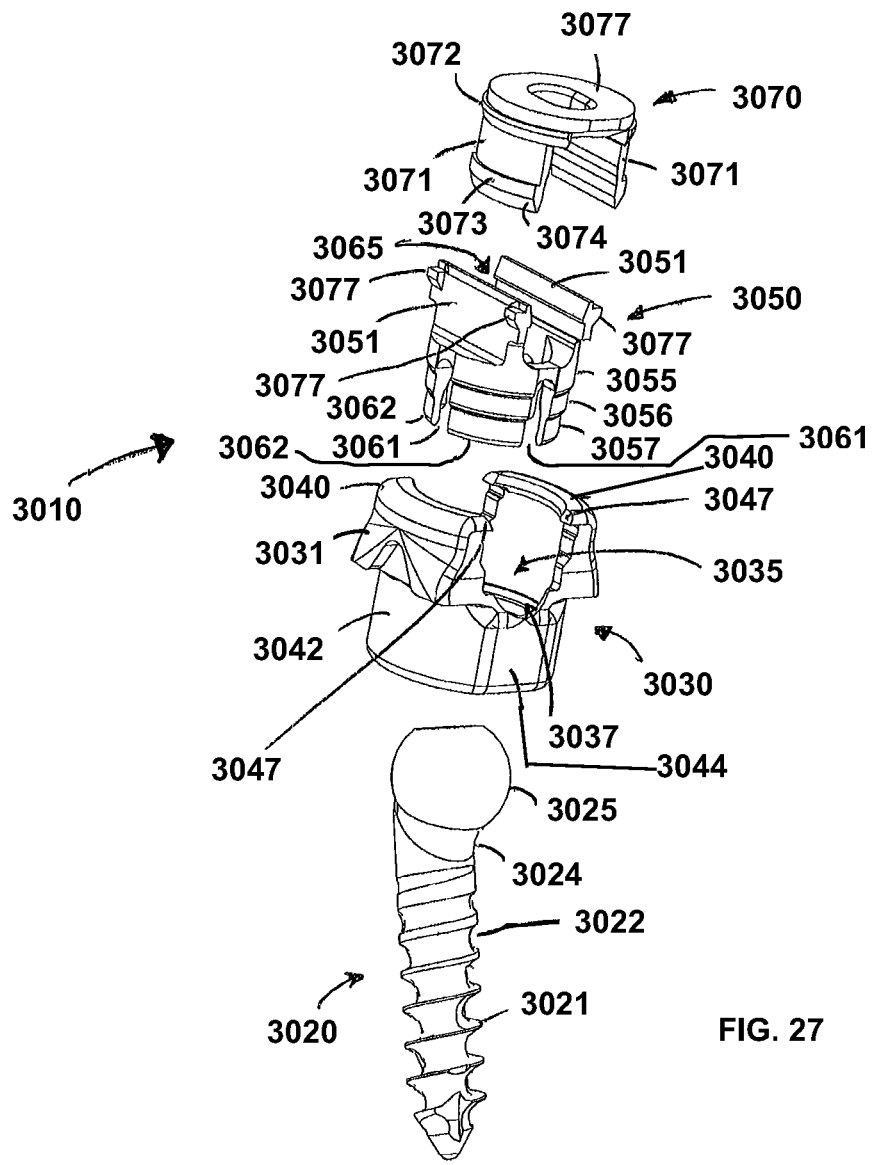
FIG. 27 is an exploded perspective view of the coupling assembly of FIG. 26.

An embodiment of a novel pedicle screw assembly designed for use when it is desired for the anchor member to be able to be pivoted to an extreme angle relative to the axis of the coupling device is shown in FIGS. 26 and 27. FIG. 26 shows the assembled device 3010 secured to a spinal rod 3025, while FIG. 27 shows an exploded view of the device. As with other embodiments, the anchor member need not be a pedicle screw, and could instead be a hook, clamp, or other mounting device. The illustrated screw assembly 3010 includes an anchor member 3020 in the form of a pedicle screw with external threads 3021 formed along the shank 3020; an outer member or yoke 3030; an insert member or core member 3050; and a rod locking member in the form of a cap member 3070. Although the configuration of the assembly as illustrated is generally cylindrical, other shapes and configurations are also possible. In addition, the exterior of the illustrated assembly, and specifically the yoke member 3030 has exterior flat faces 3044 that are aligned with the upper channel slot 3035 in which the rod 3025 is received, reducing the profile along the length of the rod. These flat faces 3044 therefore allow more assemblies to be connected along a given length of the spinal rod than would otherwise be possible, and in addition reduce the mass and material required for manufacture of the coupling assembly.

As with other embodiments, the screw assembly 3010 secures a spinal rod 3025 by urging the arms of the insert or inner core member 3050 inwardly toward each other and against the surface of the rod 3025, fixing the rod in place with respect to the anchor member 3020. The position of the anchor member 3020 is fixed by shifting the outer member 3030 over the insert member 3050, compressing the lower portion of the insert member against the head 3025 of the anchor located within a cavity of the insert member 3050. In the illustrated embodiment, the outer member or yoke 3030 is generally cylindrical in shape, albeit with the previously described diametrically opposite flat portions 3044 along its outer surface, with laterally extending shoulder portions 3031 on either side of the channel 3035 through which the rod 3025 passes. The shelf 3032 underneath each shoulder portion may be used to grip the yoke 3030 in order to shift the yoke with respect to the inner core member 3050. For instance, a tool may be used to grip one or more portions of the shelves 3032, with an upward force from the tool shifting the yoke 3030 upward with respect to the inner core member 3050. In the illustrated embodiment, a central tapered recess 3033 is located within the shoulder portion 3031 to facilitate centering of a gripping tool along the shelf 3032. Sloped surfaces forming the sides of the recess 3033 naturally lead a gripping tool to the peak at the center of the recess 3033.

The cap member 3070 associated with the embodiment shown in FIGS. 26 and 27 is provided with a central opening 3075 providing a surface which may be grasped by an instrument or tool for inserting or removing the cap. The opening 3075 allows the cap 3070 to be manipulated without grasping at the outer edges 3076 of the cap, allowing a centralized force to push the cap into place and to pull the cap out from the yoke 3030. For instance, a driving member may be equipped with projections that snap-lock into the opening 3075 in the top of the cap member 3070 to hold the cap member in place during insertion, or to grip the cap for removal. Since wedging the legs 3071 of the cap member between the outer member 3030 and the arms 3051 of the insert core member 3050 locks the spinal rod in place, the cap need not contact the spinal rod even when fully locked, and in fact may be designed with a clearance on the underside of the cap in order to avoid contact with the rod.

FIG. 27 is an exploded view of the pedicle screw system of FIG. 26, showing the pedicle screw assembly 3010 in a disassembled state. In this view, details of the individual components of the assembly may be more clearly viewed. For instance, the entire cap member 3070 is shown and it includes a generally cylindrical or disk-like body portion 3077 having legs 3071 extending downward from the top portion. In the illustrated embodiment, the lateral edges of the cap top portion contain lips or ridges 3072 to help secure the cap within the yoke 3030 upon full insertion. The lips 3072 shown include a sloped bottom surface to be more easily inserted downward. A flat upper surface of the lip 3072 prevents the cap from backing out from the yoke once inserted by abutting a ridge 3036 on the interior of the outer member 3030. Similarly, the cap legs 3071 as depicted each contain a laterally extending foot portion 3073 for snap locking into the yoke 3033 after passing the outer member interior ridge 3036. The lower surface 3074 of the foot portion 3073 allows the foot portion to be easily inserted into the yoke, while a flat upper surface of the foot prevents retrograde motion of the cap past ridge 3036.

The fixation member depicted in FIG. 27 is a screw member having a generally spherical head 3025 and a shank 3022 with threads 3021 along the length of the shank 3022. In the illustrated embodiment, the head of the screw 3020 is offset from the shank so that the center 3025a of the head portion 3025 offset from the central axis 3026 of the shank 3022. A neck portion 3024 links the head portion 3025 to the shank. This offset head configuration allows the shank to be pivoted to a more pronounced angle in one direction than would be possible if the head portion were aligned along the axis of the shank, as explained further below in connection with FIG. 30d. Alternatively, if increased angulation is not necessary a normal screw may be employed, with the head disposed directly above the shank so that the center of the head is in alignment with the central longitudinal axis of the shank. Furthermore, it is contemplated that other forms of anchor members for securing the assembly to the vertebrae may be used, such as hooks or clamps. Likewise, use of the offset head anchor member is not limited to the types of coupling members disclosed herein, and may be used in conjunction with other coupling devices known in the art.

Figure 28A:
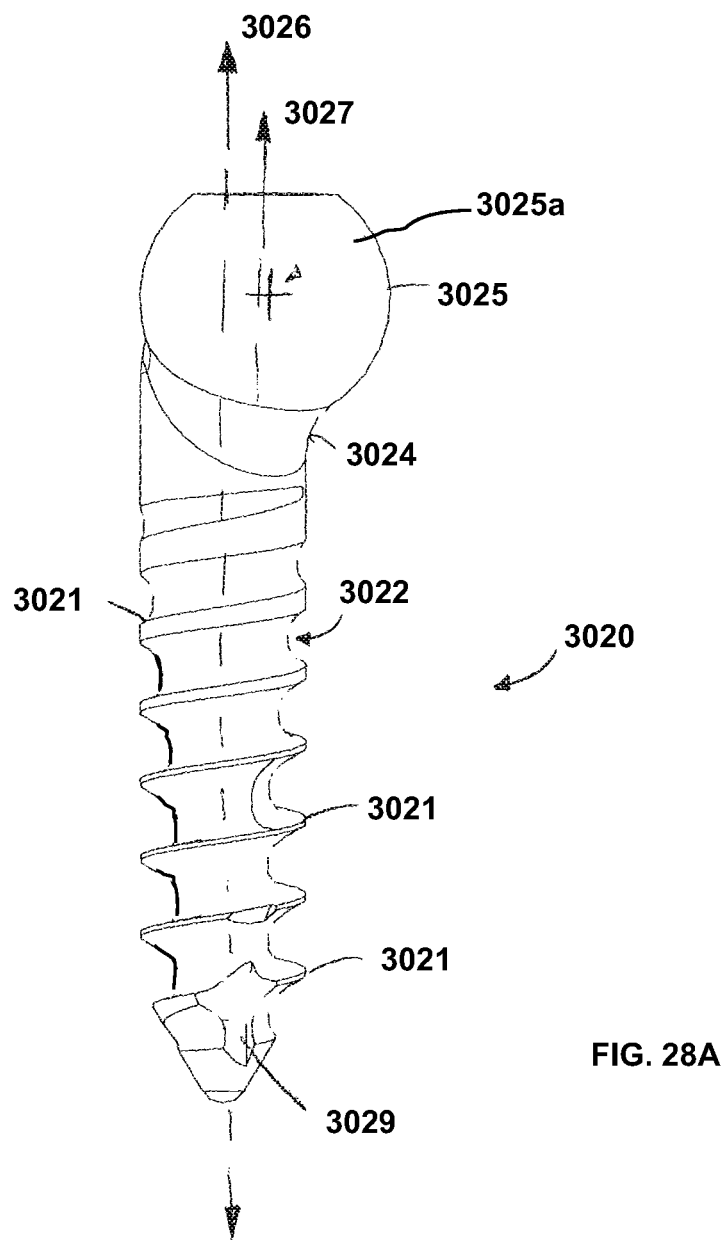
FIGS. 28A and 28B are side elevational and perspective views, respectively, of the pedicle screw anchor member showing the respective offset axes of the head portion and shank portion thereof.
Figure 28B:
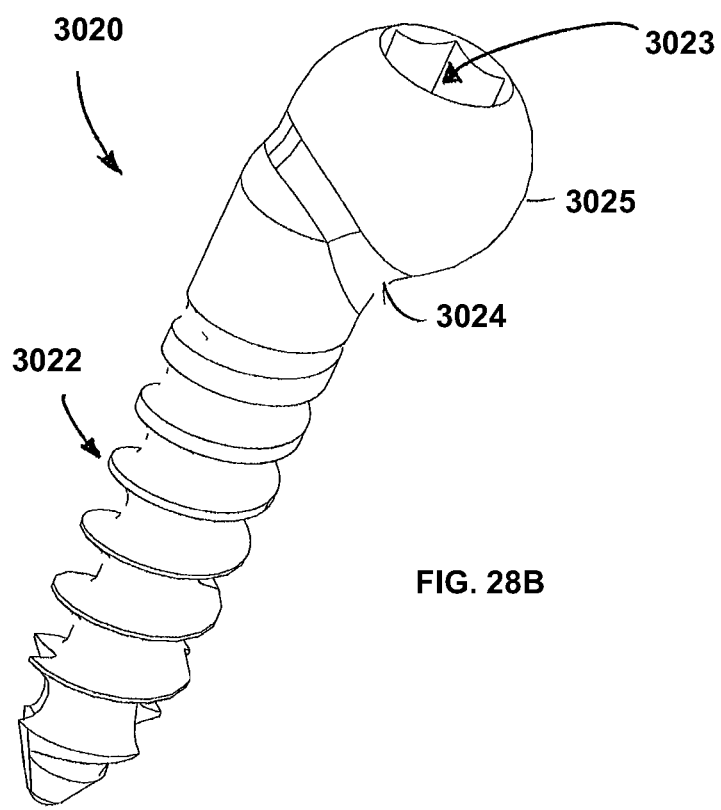

FIGS. 28A-B show the screw fixation member 3020 in greater detail. This type of anchor may be used with any of the coupling devices described herein, as well as in other types of coupling devices. As previously described, helical threads 3021 winding around the shank portion 3022 secure the assembly to bone. The central longitudinal axis of the shank portion 3022 is shown by dashed line 3026. The generally spherical head portion 3025 of the fixation member has a center 3025a that is not aligned with the shank axis 3026. A line that passes through the center 3025a of the head 3025 and through the center of the upper drive recess or socket 3023 is the central axis of the screw head portion 3025 and is shown as dashed line 3027. This screw head axis 3027 does not coincide with the shank longitudinal axis 3026. This offset head allows a normal range of pivoting for an associated coupling member when the screw 3020 is mounted at an angle into a vertebra, as explained below in connection with FIG. 35. This is particularly advantageous in the cervical spine, which is curved and relatively small so that it is not always possible to implant an anchor member perpendicular to a vertebra.

A cutaway portion 3029 may be provided towards the tip of the screw to facilitate penetration of bone. The screw may also be provided with an opening to a central cannula running axially through the screw shank 3022. A guide wire may be passed through the cannula in order to direct the screw along a predetermined path, making the screw well suited for minimally invasive surgery.

As shown in FIG. 28B, the drive recess 3023 is located in the head portion 3025 in order to receive an insertion tool for driving the screw into bone. Recess 3023 may have a polygonal or irregular shape so that rotation of an insertion tool within the recess 3023 causes rotation of the screw 3020. Since the head portion is offset from the shank axis, however, rotating a tool within the recess 3023 will cause the screw shank 3022 to orbitally rotate about the head portion 3025 rather than to simply bore into the bone, complicating the anchoring process unless a specialized tool is employed, as described below.

Figure 29:
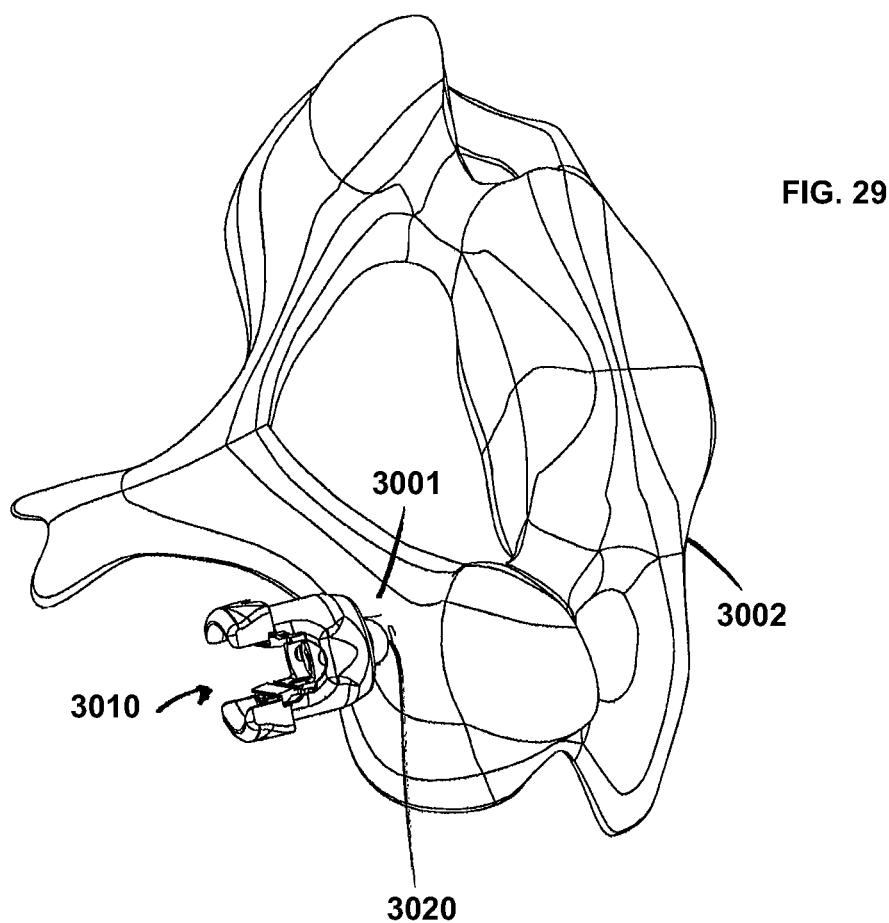
FIG. 29 shows a coupling assembly mounted to a vertebra.

The exemplary coupling assembly 3010 is shown mounted to the pedicle 3001 of a vertebra 3002 via the screw 3020 in FIG. 29. The illustrated screw 3020 is the offset angle screw as shown in FIGS. 28A-B.

Figure 30A:
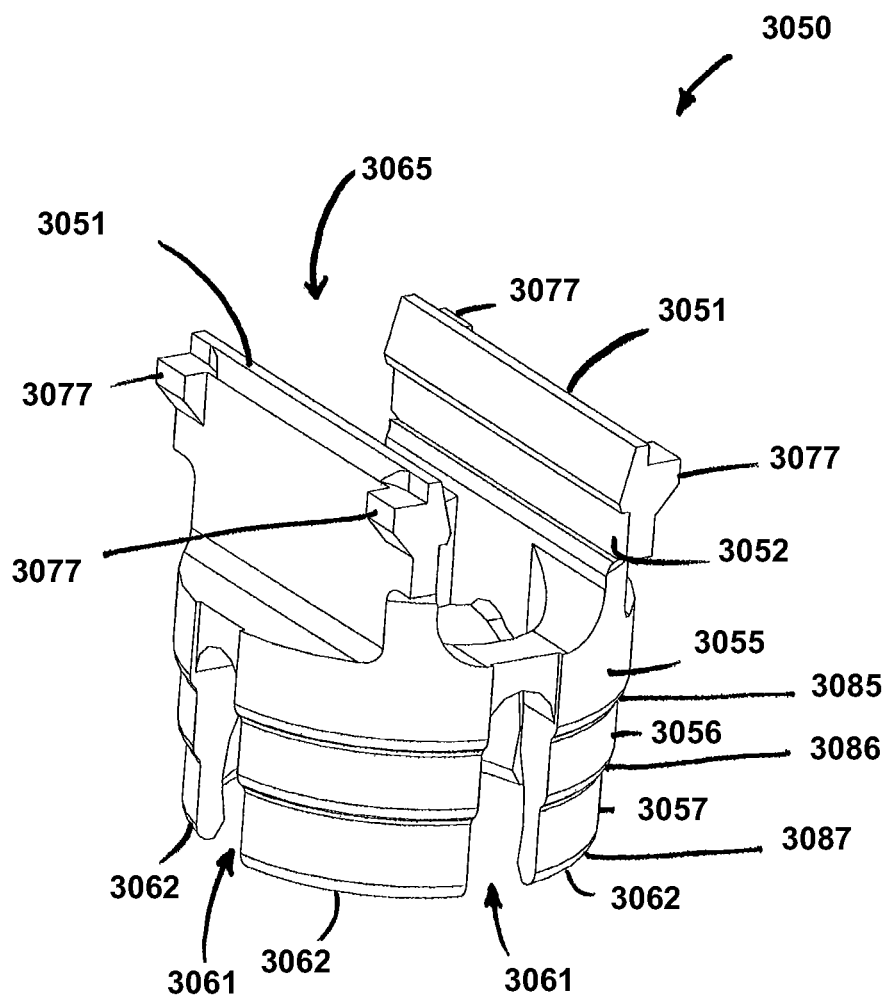
FIGS. 30A and 30B are top and bottom isometric views of an insert member or core member of a coupling assembly.
Figure 30B:
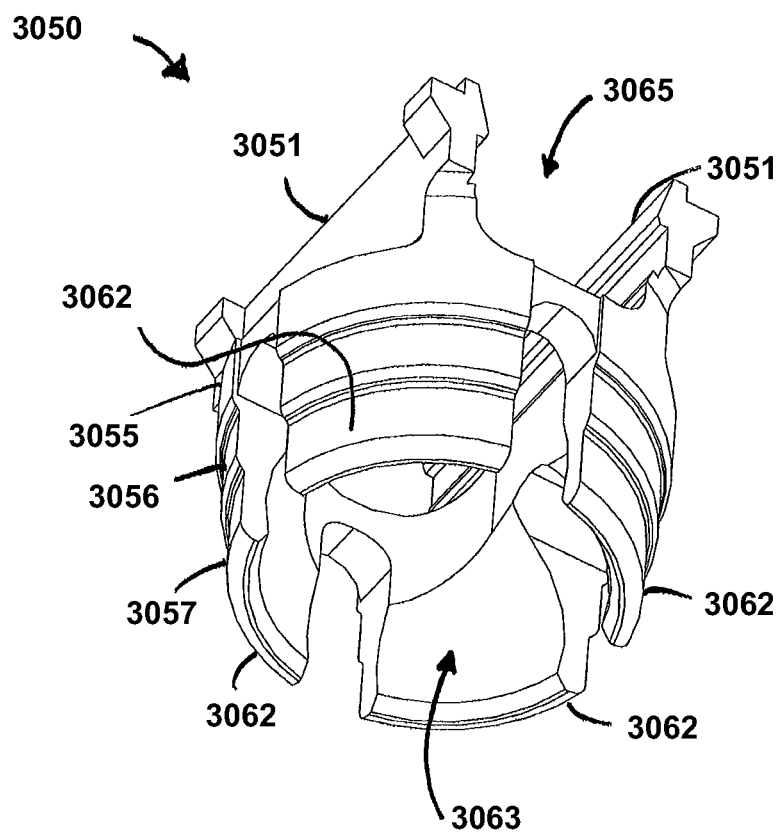
Figure 30C:
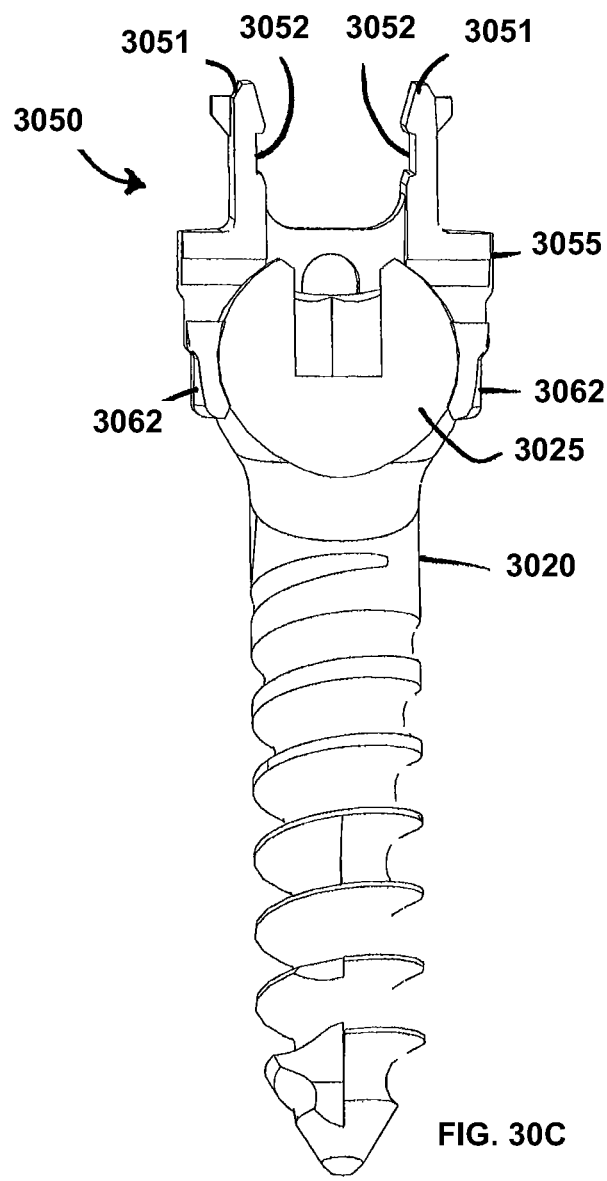
FIGS. 30C and 30D are front and side cross-sectional views, respectively, of the offset head of the pedicle screw member received in a core member of the coupling assembly.
Figure 30D:
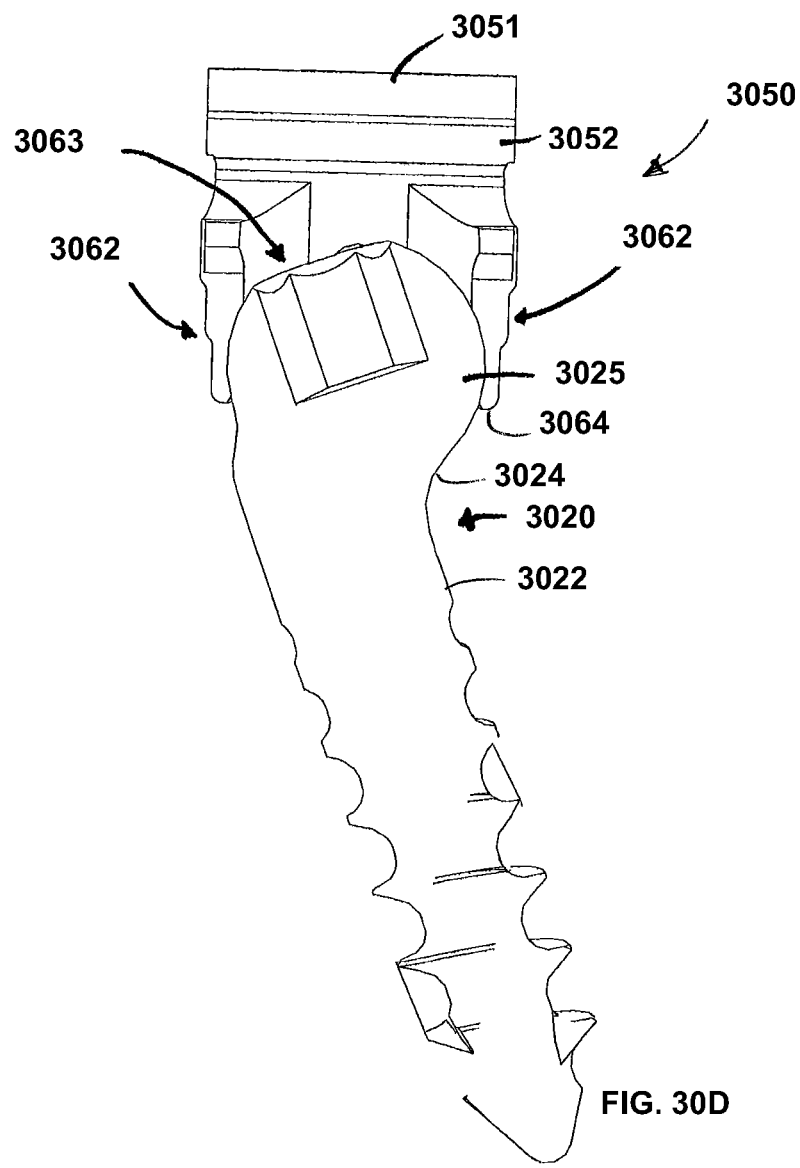

The insert member 3050 of the device shown in FIG. 27 is shown in more detail in FIGS. 30A-B. As with other embodiments described herein, the insert member or core member 3050 is provided to receive the rod and the fixation member. The exemplary core member 3050 includes a base portion 3055 having a generally disk shape. Arms 3051 extend upward from the base portion 3055 forming a channel 3065 between the arms in which the spinal rod or similar member is received. The rod may be gripped by contact features on the interior of the arms, such as one or more projections. In the illustrated core member 3050, a groove 3052 runs along the length of each arm 3051 in the direction of the channel. When the rod is received in the channel 3051, the most lateral surfaces of the rod will rest in these grooves 3052, providing a snap fit to lightly retain the rod within the channel 3065 without use of a locking member such as a cap member (3070, FIGS. 26-27).

Extending from the underside of the base portion 3055 of the core member are four finger-like projections 3062 for gripping the head of the anchor member. The projections 3062 are sized and configured to form a pocket in which the anchor head may be retained. The finger-like projections 3062 as depicted are equally spaced by four compression gaps 3061, but other configurations are possible with different numbers of finger-like projections and compression gaps. In the illustrated embodiment, the compression gaps 3061 are equally spaced around the circumference of the core member 3050 and are of equal length, extending up to the base portion 3055. The gaps 3061 allow the finger-like projections 3062 to flex outward, expanding the lower portion of the core member 3050 to receive the head of the fixation member in a snap-lock manner. The gaps 3061 also allow the finger-like projections 3062 to be forced inward to compress around the head of the anchor member, locking the anchor member in place at a desired angle with a frictional force.

The finger-like projections 3062 of the illustrated insert member include a step formation forming a tapered lower portion for the core member 3050. In the illustrated embodiment, the base portion 3055 forms a first step, while a second step 3056 located below is positioned radially inward from the base portion 3055. The third step 3057 is positioned radially inward from the second step 3056. Although a smooth, continuous tapered surface could be employed in the core member 3050, the steps 3055, 3056, and 3057 allow the core member to be shifted into three discrete positions within the yoke 3030 to cause the finger-like projections 3062 to apply a predetermined amount of locking force onto the anchor head captured therein. The surgeon manipulating the pedicle screw assembly also receives tactile feedback while shifting the core member 3050 within the yoke 3030, as transitioning from one step to another involves a sudden increase in the frictional force between the core member 3050 and the yoke 3030. In order to facilitate insertion of the core member 3050 into the yoke or outer member, steps 3055, 3056, and 3057 are each provided with a beveled edge 3085, 3086, and 3087, respectively, that will interact with the yoke to force the finger-like projections progressively more inward as the core member 3050 is inserted further into the yoke.

The above-identified structures of the insert member are shown from below in FIG. 30B, where it can be seen that the finger-like projections 3062 form a generally spherical cavity 3063. The cavity pivotably receives the generally spherical head portion 3025 of the anchor member 3020, as shown in front cross-section (FIG. 30C) and side cross-section (FIG. 30D), which both illustrate a pedicle screw 3020 with an offset head 3025 received in the core member 3050. As best seen from FIG. 30d, the offset configuration of the anchor head portion reduces interference between the anchor shank 3022 or other attachment portion and the core inset member 3050. The shank is positioned toward one side of the head 3025 (toward the left in FIG. 30D), so that as the anchor is pivoted forward (toward the right in FIG. 30D) movement is not limited until the neck portion 3024 of the anchor abuts the lower edge 3064 of the insert member. Due to the offset nature of the head portion, one side of the neck 3024 is located much closer to the center of the head than it would be if the head portion were aligned with the axis of the shank. This allows a significantly greater ability of the shank 3022 to pivot in one direction (to the right in FIG. 30d). For instance, the screw may be configured to allow the shank 3022 to pivot 60 degrees or more away from a central axis of the coupling device. The screw may even be configured to achieve a 90 degree angle if desired, so that the shank 3022 is directed to the side of the coupling device.

Figure 31A:
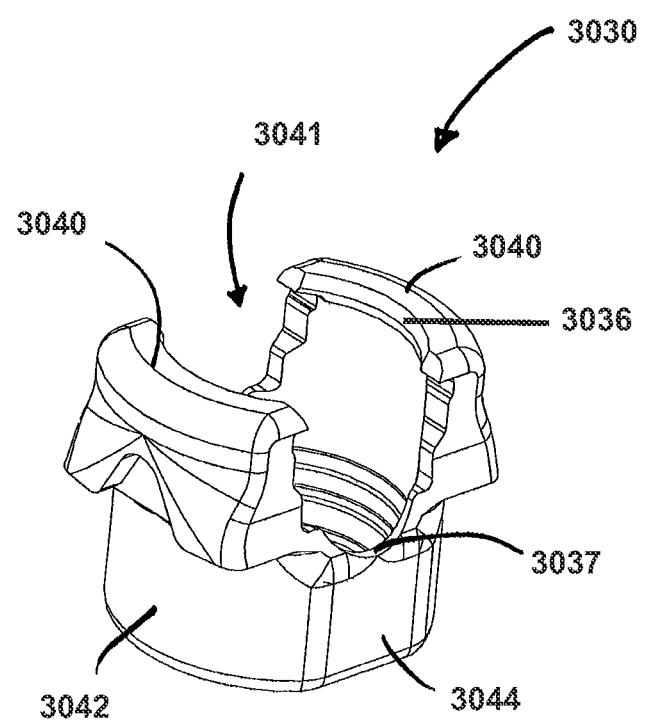
FIGS. 31A and 31B are isometric and cross-sectional views, respectively, of an outer member or yoke of the coupling assembly.
Figure 31B:
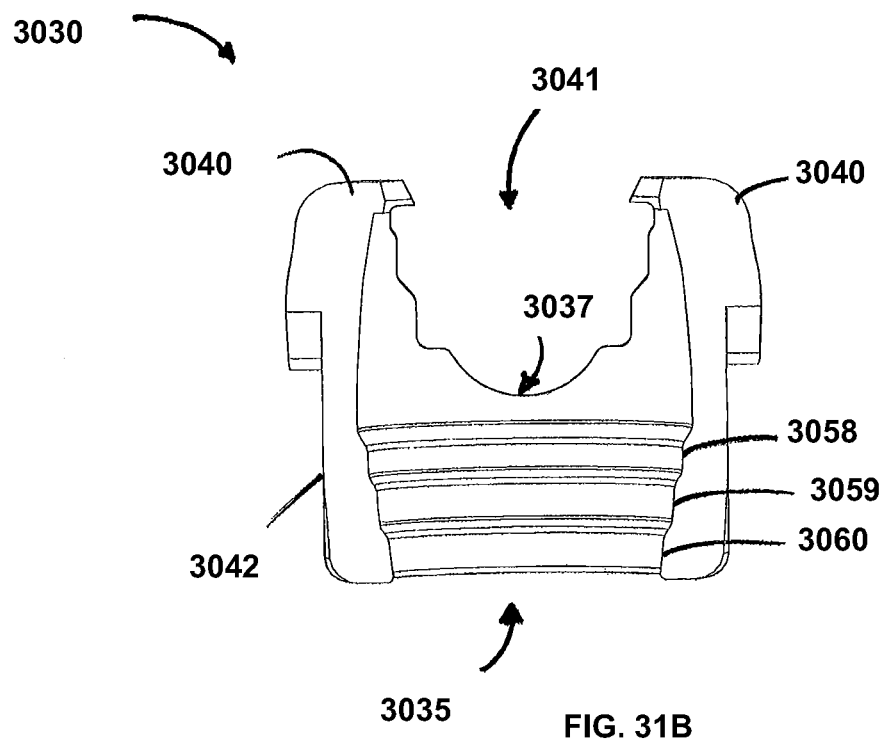
Figure 32A:
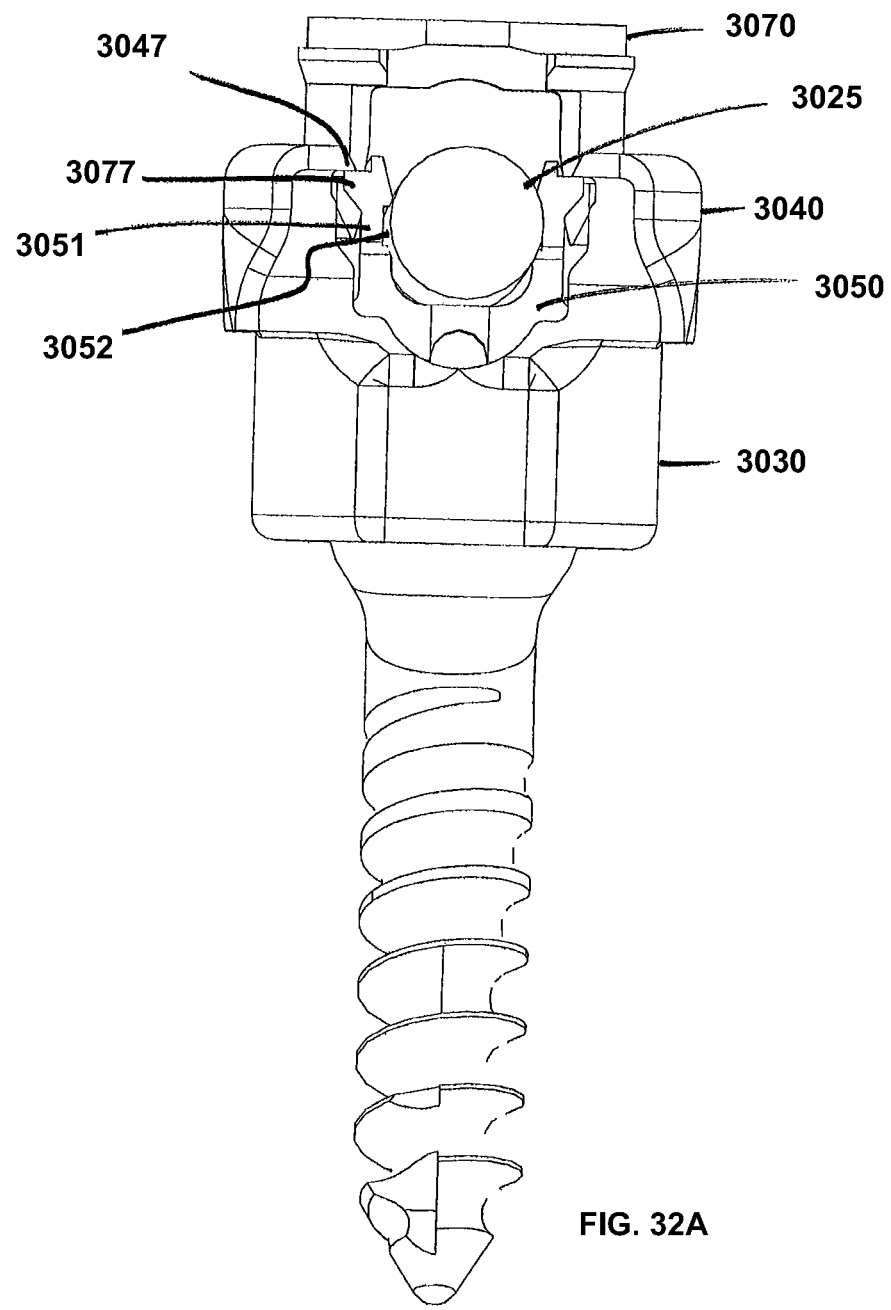
FIGS. 32A-D are front and cross-sectional views demonstrating locking of an exemplary coupling assembly.

As previously described with respect to other embodiments, retention tabs 3077 (FIG. 30A) are located on the arms of the core member 3050 to interact with complementary retention tabs 3047 located on the yoke 3030 (FIGS. 31A, 32A; described below). As the core member 3050 is inserted into the axial bore 3035 of the yoke 3030 (FIGS. 27, 31A-B), retention tabs 3077 on the core will pass retention tabs 3077 on the yoke due to downward sloped surfaces on the core retention tabs 3077 and upward sloped surfaces on the yoke retention tabs 3047, allowing for one-way shifting of the core member 3050 into the space within the yoke.

The yoke member 3030, shown in FIGS. 26-27 is shown in greater detail in FIGS. 31A and 31B and includes upright portions 3040 which form an open channel 3041 in which the rod may be received. In the illustrated embodiment, a large portion of the channel is wider than necessary for the rod to be received between the uprights 3040. A cylindrical recess or seat 3037 is located at the bottom of the channel configured to conform to the surface of the spinal rod. A generally cylindrical axial bore 3035 is formed within the center of the yoke 3030. The interior surface of the axial is bore is stepped to complement the finger-like projections 3062 of the insert member 3050 (FIGS. 30A-D). As shown in FIG. 31B, interior stepped locking features 3085, 3059, and 3060 are positioned concentrically to sequentially compress inward the finger-like projections of the core member (FIGS. 30A-D) as the core is shifted further downward through the open space or bore 3035 in the yoke 3030.

The upright portions 3040 of the yoke 3030 contain laterally extending shoulder portions 3031 which may be grasped to manipulate the outer member. The base portion 3042 of the yoke 3030 is generally cylindrical in shape, but flat surfaces 3044 are located adjacent to the rod channel 3037 in order to reduce the profile of the assembly along the length of the rod. This allows placement of several coupling assemblies adjacent one another along a relatively short length of rod, which is advantageous in areas such as the cervical spine, where the vertebrae are small in size.

As noted above, the yoke 3030 contains retention tabs 3047 located along the rod channel 3041 in order to interact with retention tabs 3077 on the core member. As the core member 3050 (FIGS. 27, 31A-D) is inserted into the axial bore 3035 of the yoke 3030, retention tabs 3077 on the core will pass retention tabs 3077 on the yoke due to downward sloped surfaces on the core retention tabs 3077 and upward sloped surfaces on the yoke retention tabs 3047, allowing for one-way shifting of the core member 3050 into the space within the yoke. The shape of the complementary retention tabs 3047, 3077, having a sloped or ramped surface on one side and an abutment surface on the other side, allows the core member 3050 to be linearly shifted into the yoke 3030 in a downward direction, but prevents retrograde motion once the retention tabs 3047 and 3077 have passed one another, so that the core does not back out of the yoke. If desired, additional retention features could be placed to provide for additional retention points, allowing for linear ratcheted movement of the core member into the yoke.

Figure 32B:
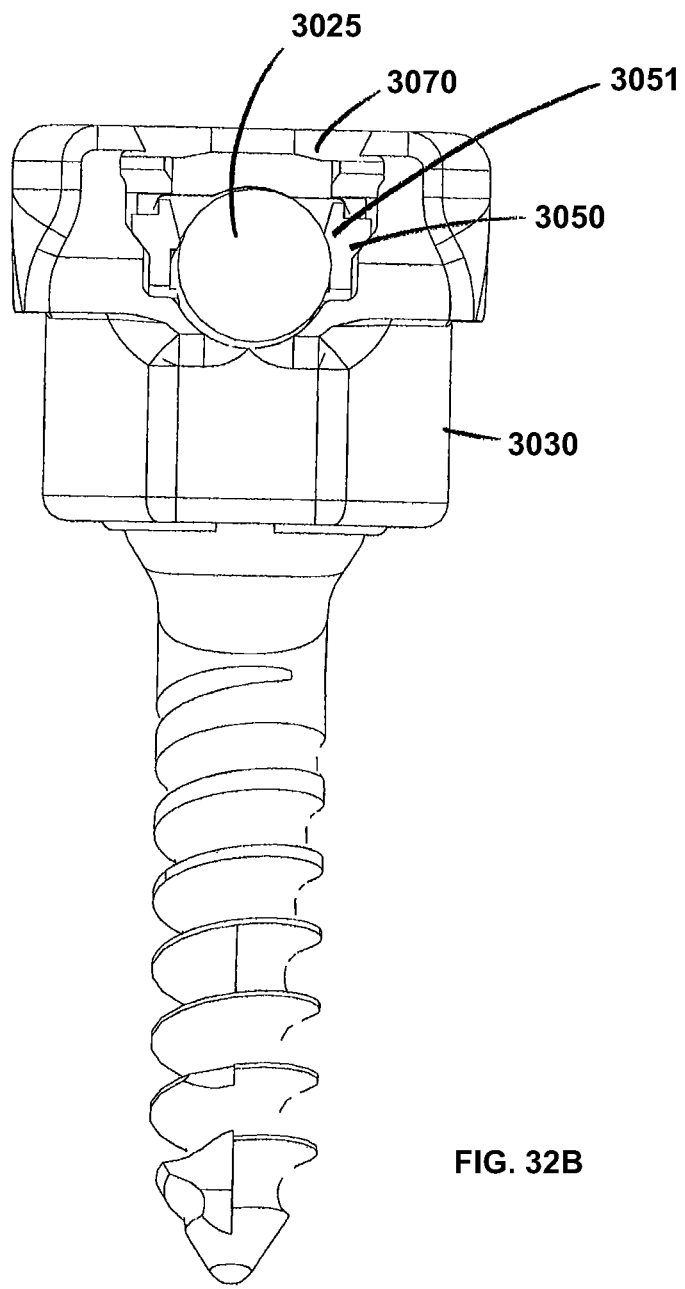
Figure 32C:
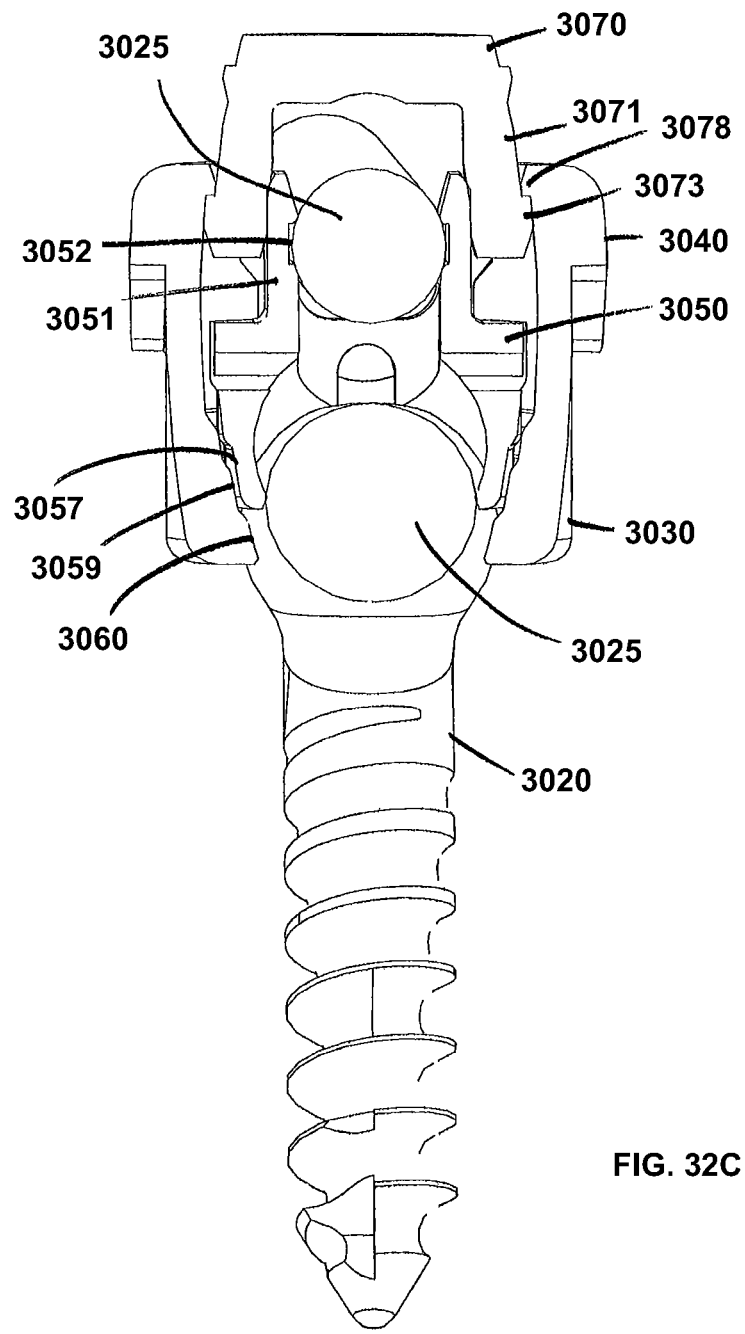

FIGS. 32A-D illustrate locking of the full coupling assembly. In FIGS. 32A and 32C, the core member 3050 is partially inserted into the yoke 3030, and yoke retention tabs 3047 interact with core member retention tabs 3077 to prevent upward movement of the core 3050 out of the space within the yoke 3030. Downward movement of the core 3050 relative to the yoke 3030 is still allowed. The rod 3025 is shown snapped into the core member 3050, received between the arms 3051 of the core member, with the lateral surfaces of the rod 3025 resting in the retention grooves 3052 of the arms. As shown in cross-section (FIG. 32C), the cap is snap-locked into the assembly, with the feet 3073 of the cap legs 3071 retained by a lip 3078 of the yoke 3080. However, the cap legs 3071 are not yet wedged between the arms 3051 of the core 3050 and the upright portions 3040 of the yoke 3030. The anchor member 3020, although coupled to the assembly, is not locked into place, since the locking features on the inside surface of the yoke member hollow space 3030 have not yet been forced into contact with their respective step portions on the finger-like projections of the core member 3050. For instance, the most radially-inward step portion, 3057, is not aligned with the most radially-inward locking feature 3060. Instead, step portion 3057 is aligned with a wider locking feature, 3059. Nevertheless, alignment of step portion 3057 with wider locking feature 3059 may be configured to cause some compression of the lower portion of the core member 3050, retaining the anchor member in place and possibly even applying some frictional force between the core member 3050 and the anchor head 3025 to reduce pivoting of the anchor member 3020.

Figure 32D:
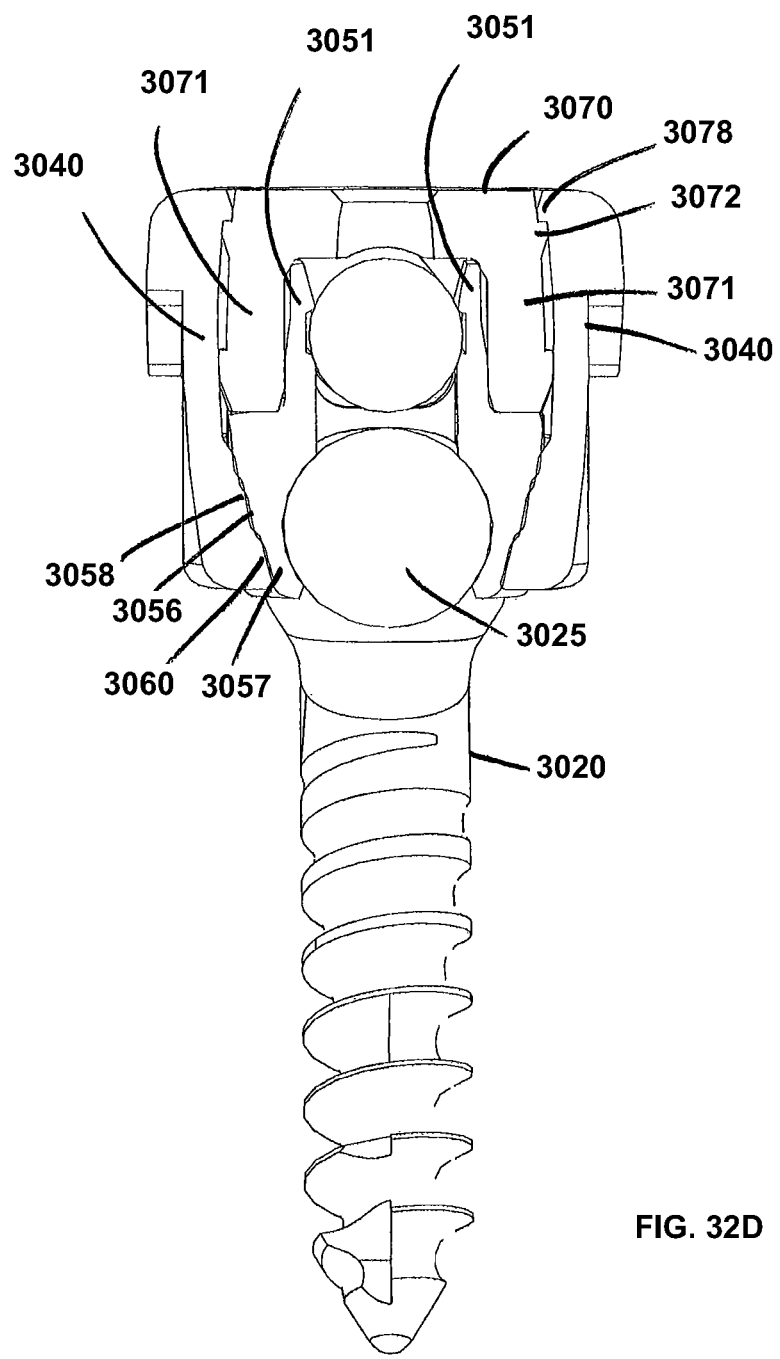

Full locking of the assembly is shown in FIGS. 32B and 32D. In this position, the cap 3070 is fully inserted into the assembly, and legs 3071 of the cap are wedged between the upright arms 3051 of the core member and the upright portions 3040 of the yoke 3030. As seen in cross-section (FIG. 32D), an upper ridge or lip 3072 on the cap 3070 may snap-lock into the yoke 3030 as it is shifted past a lip 3078 of the yoke, further securing the cap 3070 to the assembly. Furthermore, the most radially-inward step portion, 3057, is now aligned with the most radially-inward locking feature 3060. Furthermore, step 3056 is aligned with corresponding locking feature 3058. This configuration provides maximum compression force from the yoke 3030 onto the finger-like projections 3062 of the core, locking the anchor head 3025 at a set position within the core and preventing further pivoting of the anchor member 3020.

Another embodiment of a novel pedicle screw assembly designed for use in the cervical region of the spine is shown in FIGS. 33-37. In many respects this design is similar to that shown in FIGS. 26-32D, but is more streamlined. The pedicle system in FIGS. 33-37, as those described above, includes an outer member or yoke 4030, an insert member or core member 4050 having upright arms 4051 for receiving a spinal rod 4025, a cap member 4070 or other rod locking member, and an anchor member 4020. The illustrated anchor member 4020 is an offset pedicle screw, as described above, which allows the coupling assembly 4010 to be pivoted at extreme angles with respect to the anchor member 4020 even when the anchor member 4020 is initially inserted at an angle.

Figure 33:
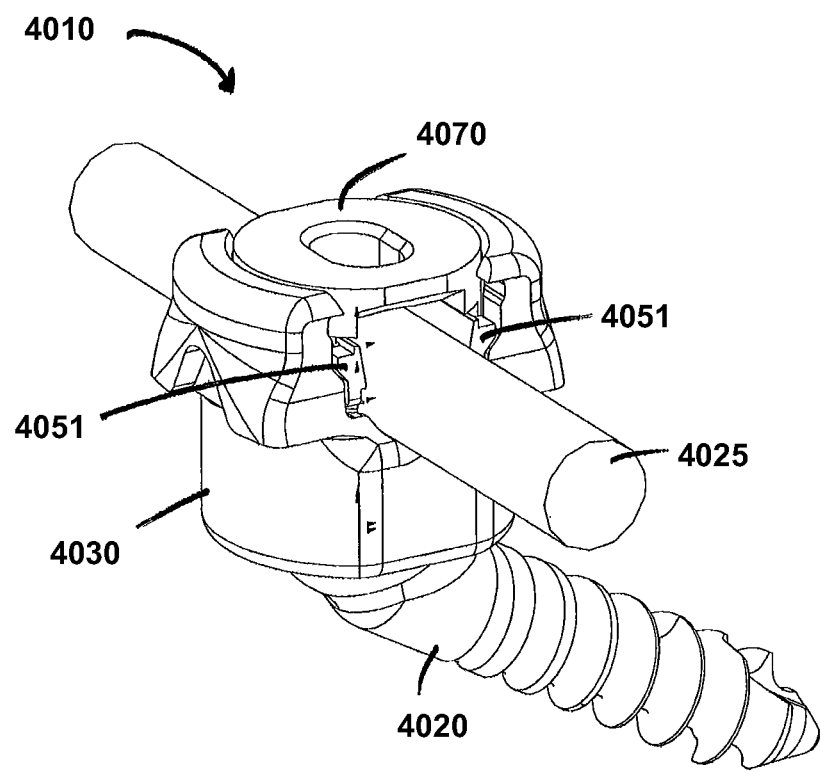
FIG. 33 is a perspective view of another exemplary coupling assembly including the anchor member having offset head and shank portions.
Figure 34:
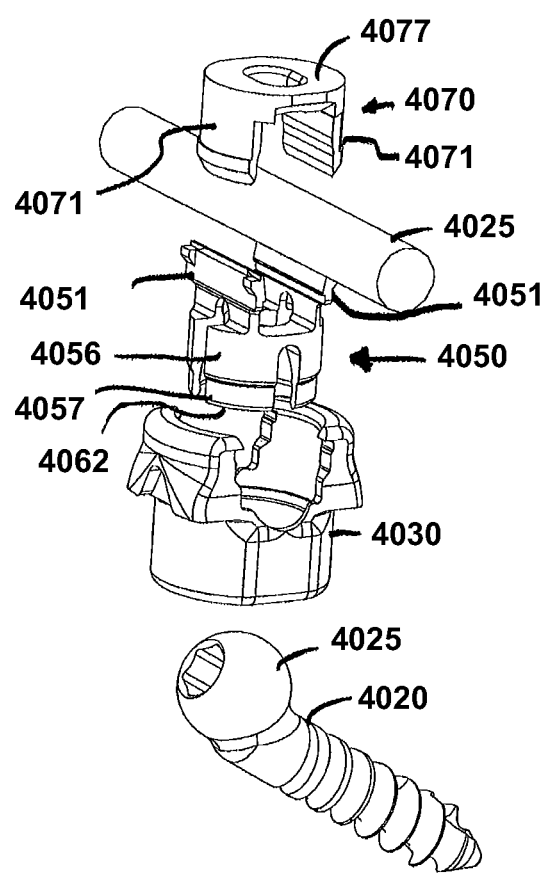
FIG. 34 is an exploded perspective view of the coupling assembly of FIG. 33.

FIG. 34 provides an exploded view of the pedicle screw system of FIG. 33, showing this embodiment of the pedicle screw assembly 4010 in a disassembled state. In this view, details of the individual components of the assembly may be more clearly viewed. Cap member 4070 includes a generally cylindrical or disk-like top portion 4077 having legs 4071 extending downward from the top portion. The cap is shown in more detail in FIGS. 37A-C. Unlike the previously described embodiment (FIG. 27), the cap 4070 does not have a lip near the top portion, reducing the force necessary for full insertion and removal of the cap. The insert member or core member 4050 of the embodiment shown in FIGS. 33-35 contains finger-like projections 4062 with a two-step structure, with step portions 4057 and 4056 for interacting with the interior of the yoke 4030.

Figure 35:
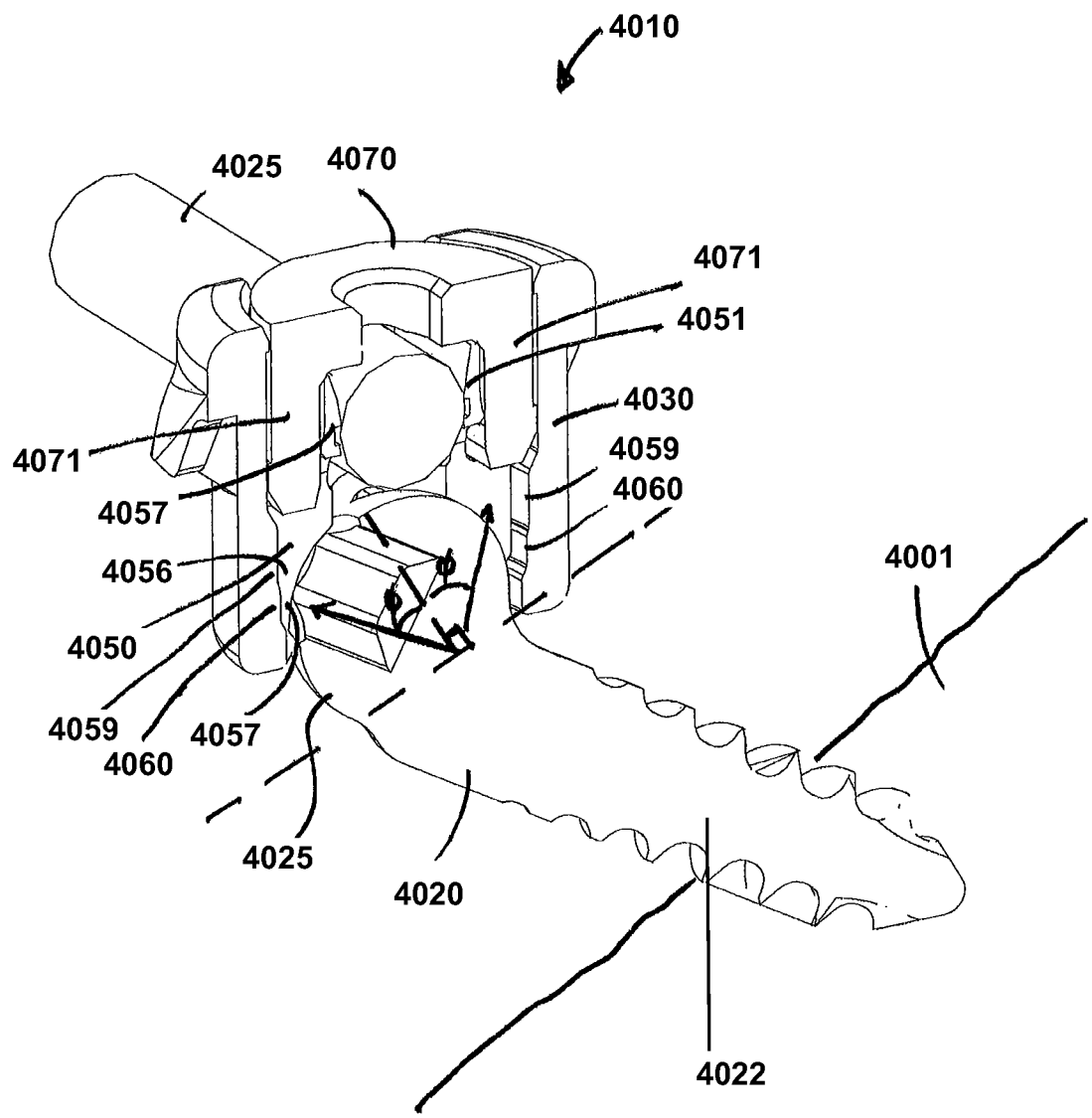
FIG. 35 is a cross-sectional view of the coupling assembly of FIG. 33.

As shown in FIG. 35, the offset anchor member 4020 may be mounted to bone 4001 at an angle and still permit a normal range of motion equivalent to that of a straight anchor member mounted substantially perpendicular to the bone. Since pivoting of the coupling device 4010 with respect to the anchor member head 4025 is limited by abutment of the device 4010 against the anchor shank 4022, offsetting the shank 4020 from the center of the head portion 4025 increases pivotability in one direction while decreasing pivotability in the opposite direction. In essence, this shifts the axis about which the device 4010 pivots when coupled to the anchor head. The anchor member 4020 and its head portion 4025 and shank portion 4022 are configured so that when the anchor is mounted at a specific angle relative to a vertebra and/or a coupling assembly, the head still allows pivoting of the coupling assembly 4010 of Ø in any direction with respect to an axis or plane normal to the surface of the bone 4001 in which the anchor is mounted. The coupling assembly 4010 depicted in FIG. 35 would not be allowed to pivot forward to the extent shown if the anchor head 4025 were mounted along the axis of the anchor's shank 4021. The loss of pivotability in one direction is not detrimental, since the anchor 4020 may be rotated 360° within the generally spherical cavity of the insert member 4050 in order to orient the anchor 4020 so that it points in a desired direction. The positioning of the head portion 4025 with respect to the shank 4022 may be altered if desired, and different configurations will offer different maximum amounts of pivotability.

Figure 36:
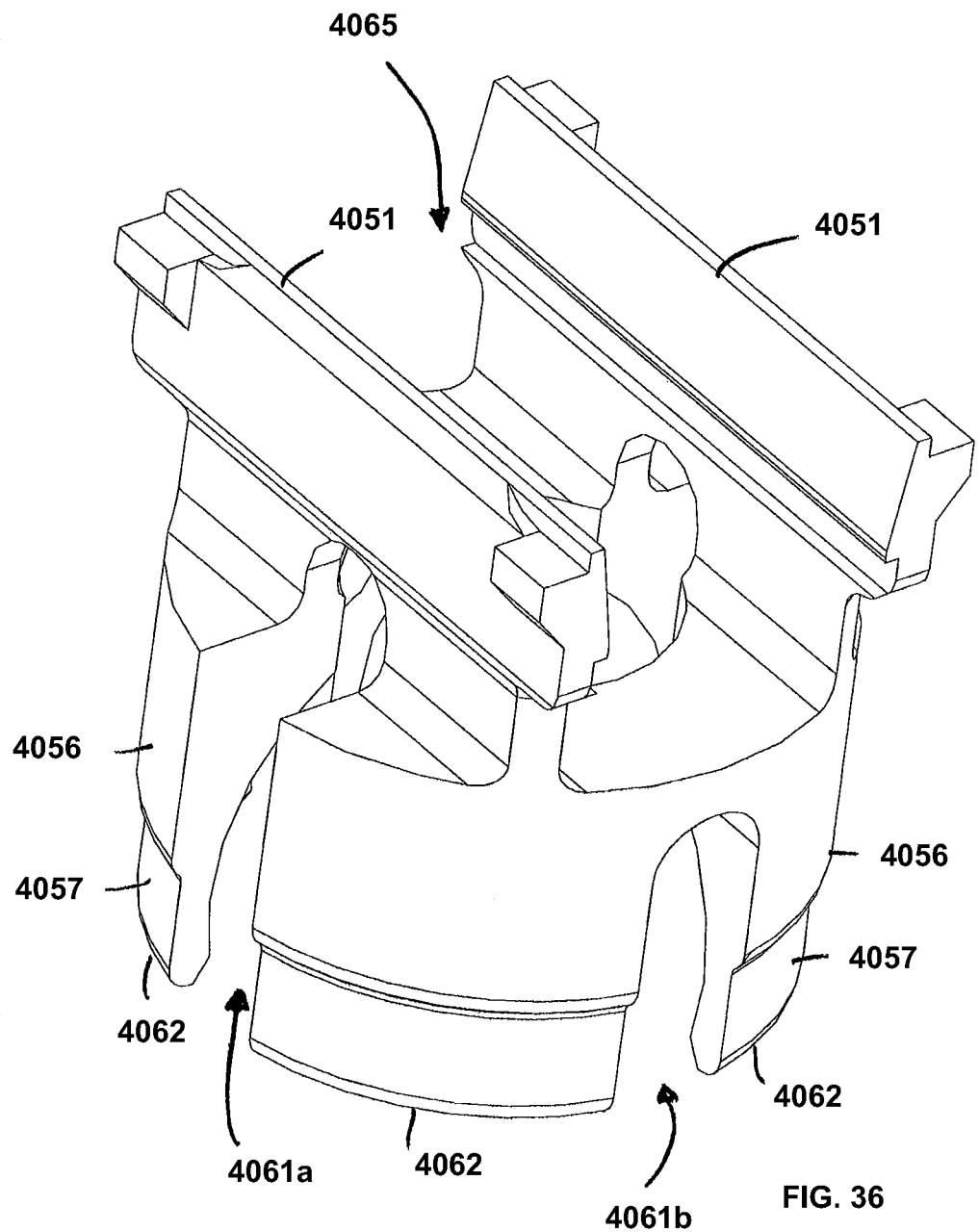
FIG. 36 is an isometric view of an insert member of the coupling assembly of FIG. 33.

The core member 4050 of the device in FIGS. 33-35 is shown in more detail in FIG. 36. Similar to insert core members described above, the core includes a channel 4065 for receiving a rod between two upright arms 4051. The lower portion of the core includes a two-step configuration with a wider portion 4056 and a narrower portion 4057 configured to be disposed against complementary locking surfaces on the interior of the outer member or yoke 4030. In order to lock the anchor member 4020 in position, the step portions 4056 and 4057 are shifted into alignment with locking features 4059 and 4060, respectively. Compression slits 4061a and 4061b allow the wall portions 4062 to be deflected inward against the head of an anchor member received therebetween and are configured to have different heights to take advantage of the increased height of the sides of the core member due to the upright arms 4051.

Figure 37A:
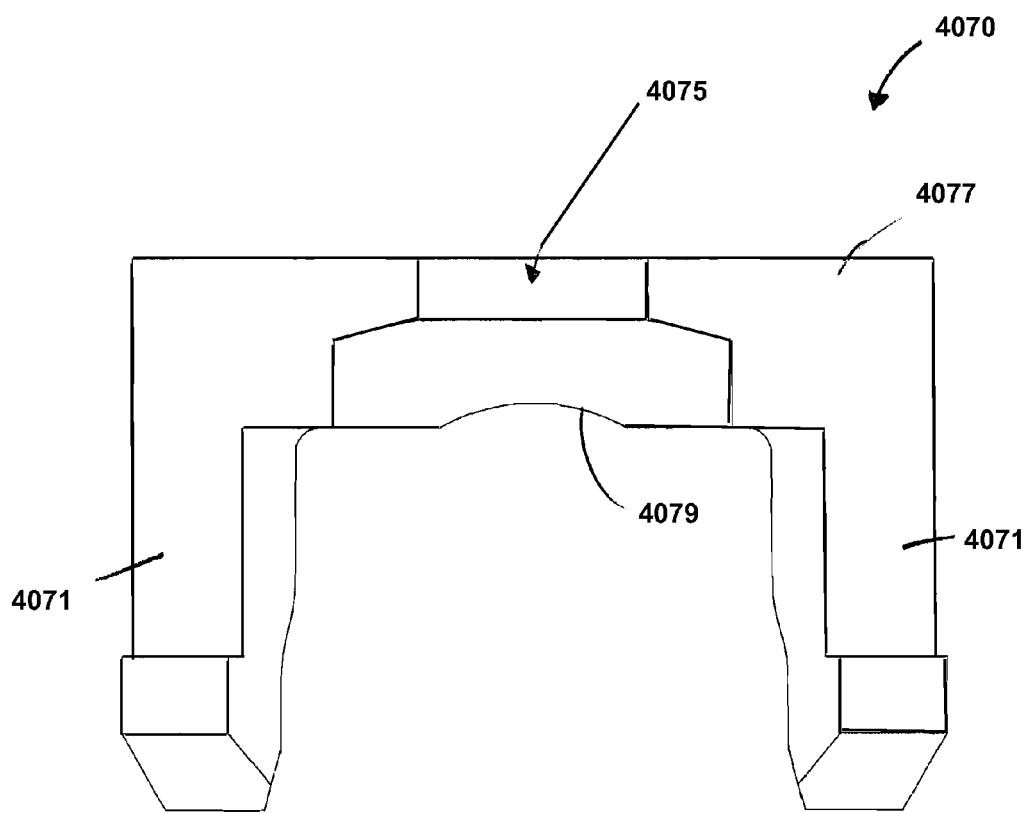
FIGS. 37A, 37B, and 37C are front, upper isometric, and lower isometric views, respectively, of a cap member for coupling assembly of FIG. 33.
Figure 37B:
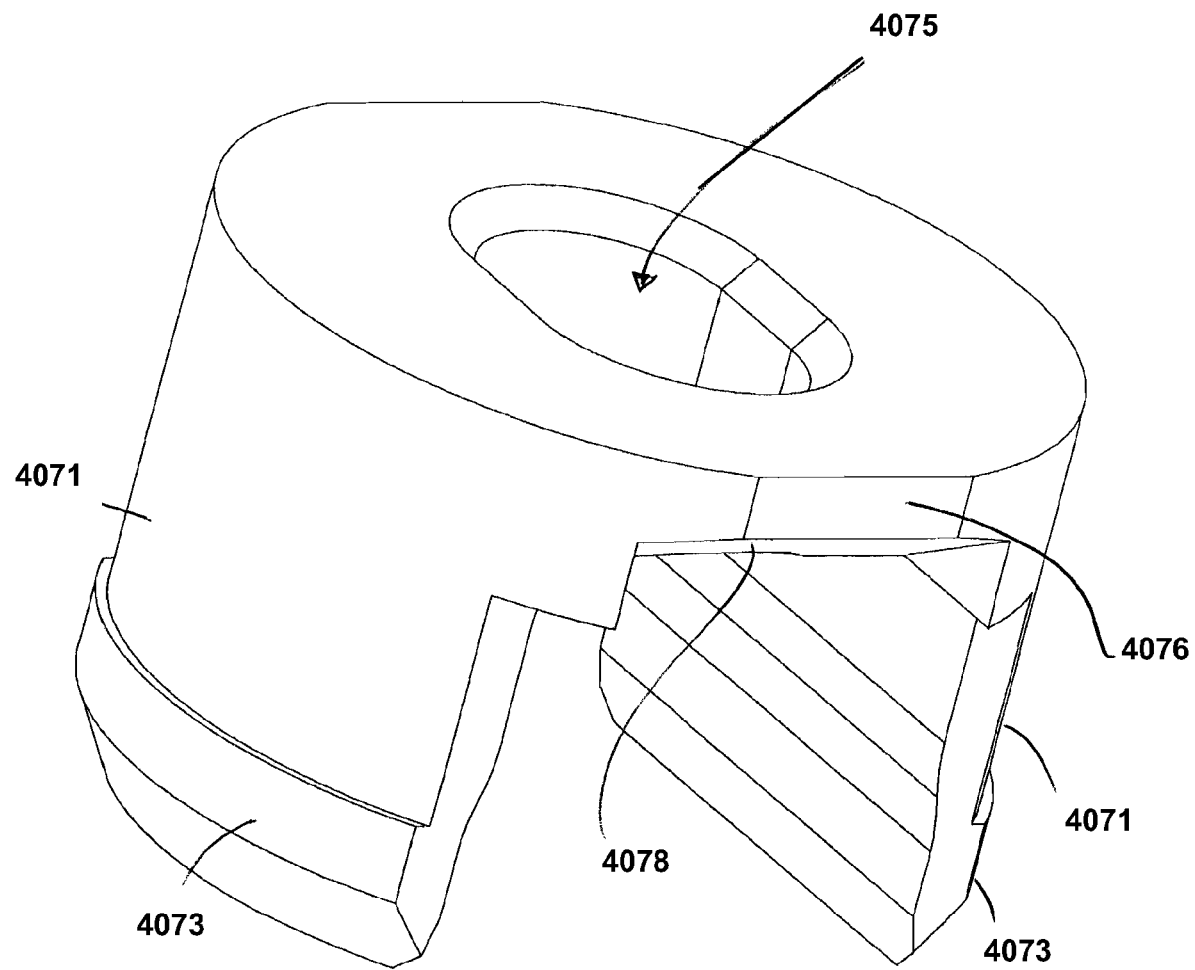
Figure 37C:
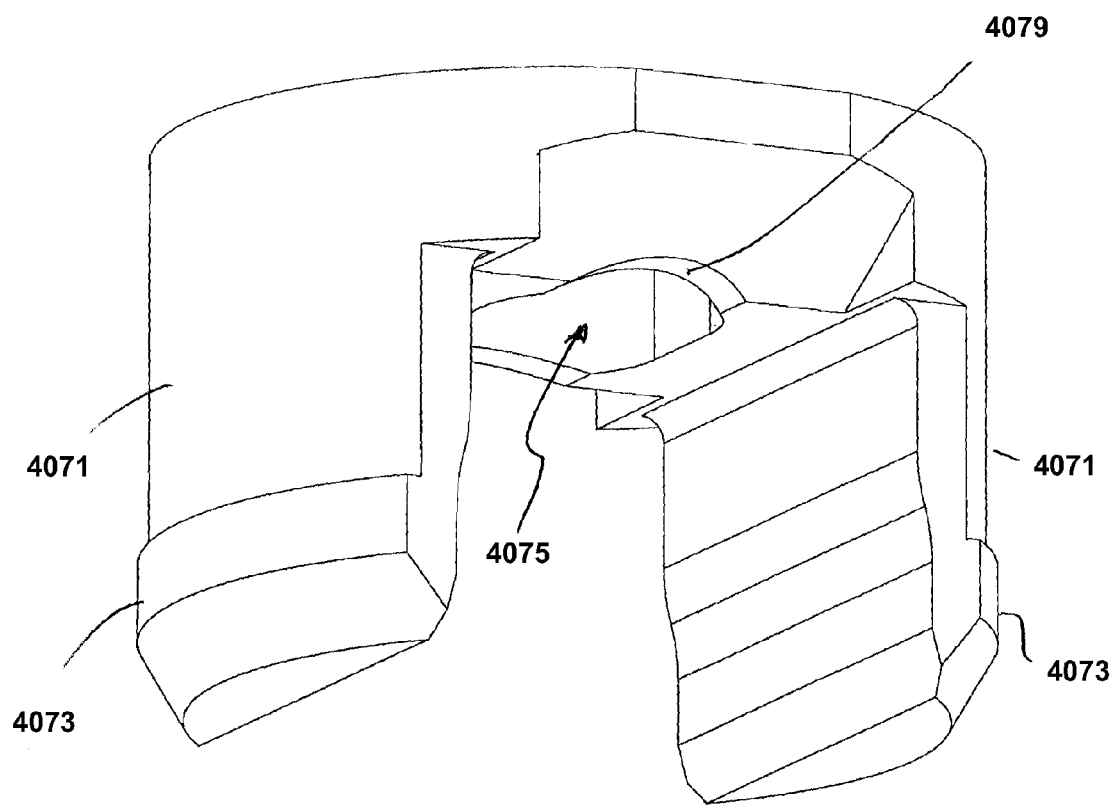

The cap member 4070 of the device in FIGS. 33-35 is shown in further detail in FIGS. 37A, 37B, and 37C. The cap member 4070 includes a relatively thin body portion 4077 and relatively thick and rigid leg portions 4071. The leg portions 4071 are thicker near the cap body portion 4077 in order to provide greater locking force when the cap is fully inserted than when the cap is partially inserted between the core member 4050 and outer yoke member 4030. The underside 4079 of the cap member has a partially cylindrical recess that can be either configured to sit flush with the exterior of the spinal rod or avoid contact with the spinal rod, depending on the length of the cap legs 4071 and the thickness of the cap body 4077. A central aperture 4075 provides a point of attachment for a cap insertion instrument, and also reduces the mass of the cap. Outwardly-directed feet 4073 on the leg portions allow the cap to be provisionally held within the outer body portion 4030 as previously described in connection with other embodiments.

Yet another embodiment of a pedicle screw system appropriate for use in the cervical spine is shown in FIGS. 38-41. As can bee seen, this embodiment has a thicker cap 5070, and an extremely slim profile when viewed from the side. The illustrated anchor member is straight, although an offset-angle anchor member may also be used.

Figure 38:
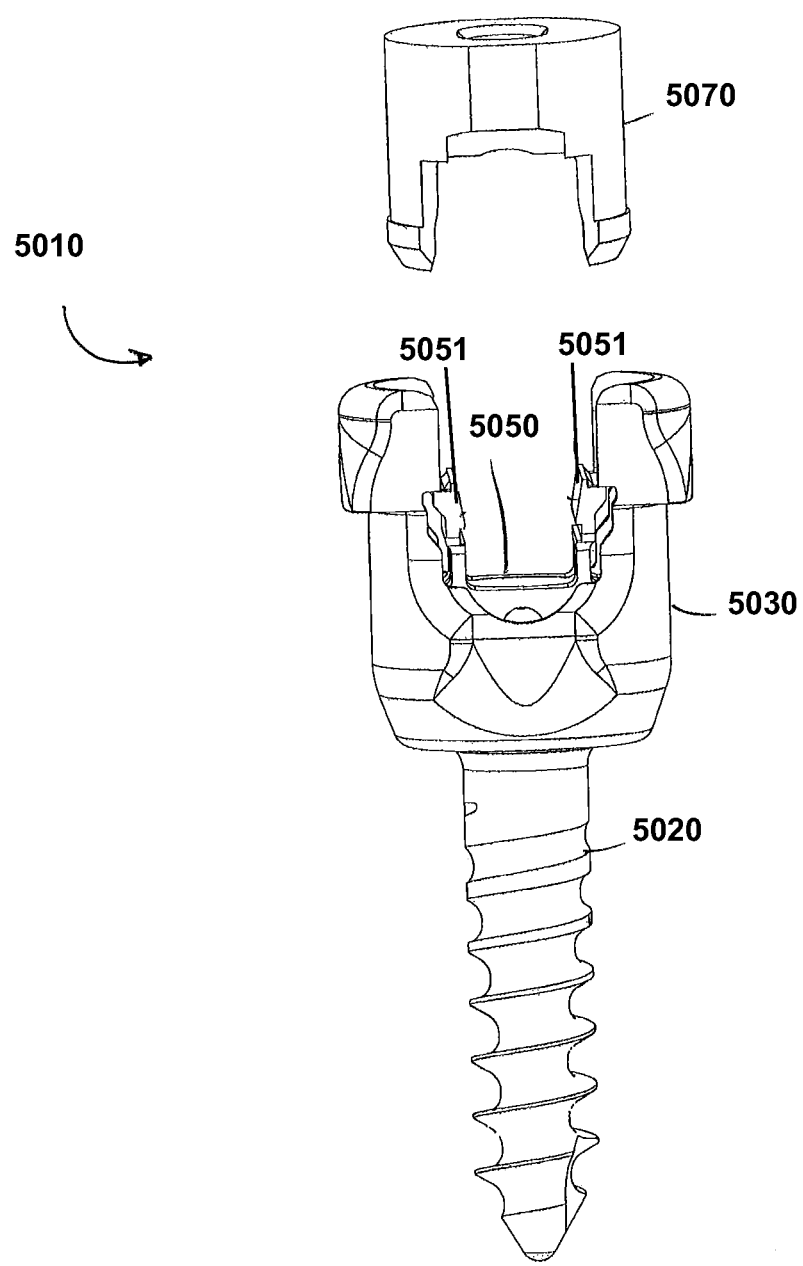
FIG. 38 is a front view of an additional embodiment of a coupling assembly.

The pedicle system contains an outer member or yoke 5030, an insert member or core member 5050 having upright arms 5051 for receiving a spinal rod, a cap member 5070 or other rod locking member, and an anchor member 5020. The illustrated anchor member 5020 is a traditional pedicle screw, although alternatively an offset-head pedicles screw as discussed above may be used to allow the coupling assembly 5010 to be pivoted at extreme angles with respect to the anchor member even when the anchor member is initially inserted at an angle. FIG. 38 shows the anchor 5020, the yoke 5030, and the core insert 5050 assembled, with the cap member 5070 removed. The above structures are shown in cross-section in FIG. 39, which shows that the core insert may have a two-stepped exterior configuration to provide a partial lock and final lock when positioned against corresponding surfaces on the interior surface of the yoke member 5030.

Figure 40:
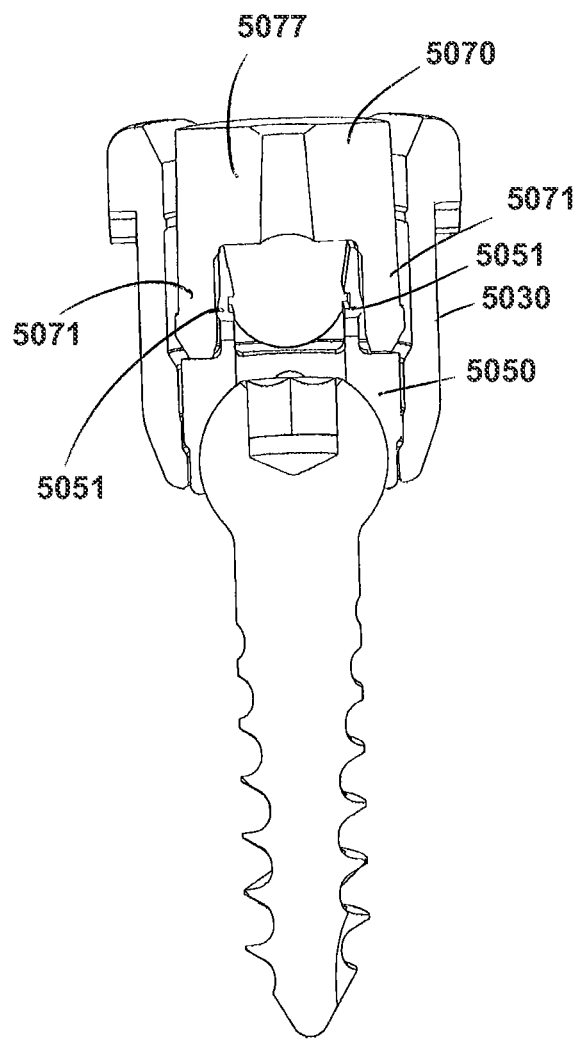
FIG. 40 is a cross-sectional view of the coupling assembly of FIG. 38 when fully locked.

Insertion of the cap member 5070 is shown in FIG. 40. The legs 5071 of the cap member 5070 are designed to be wedged between the upright arms 5051 of the insert member 5050 and the interior surface of the outer yoke member 5030. The generally cylindrical body 5077 of the cap member 5070 has a substantial thickness to provide additional rigidity to the coupling assembly when fully locked.

Figure 39:
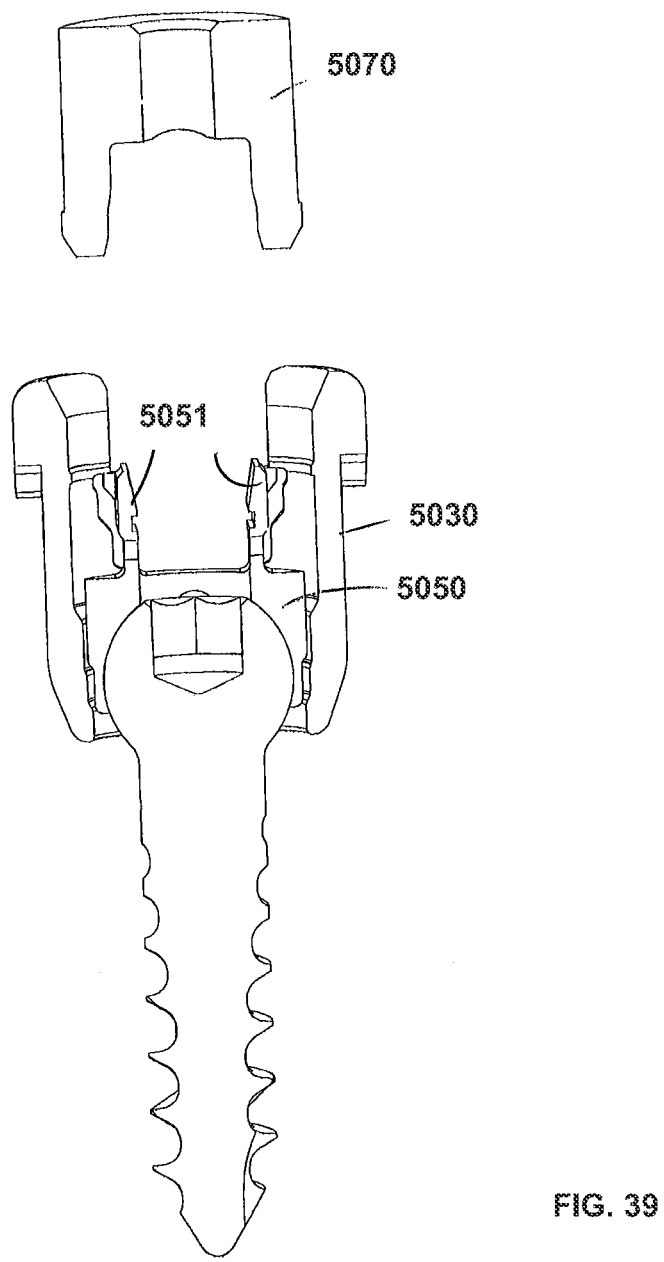
FIG. 39 is a cross-sectional view of the coupling assembly of FIG. 38.
Figure 41:
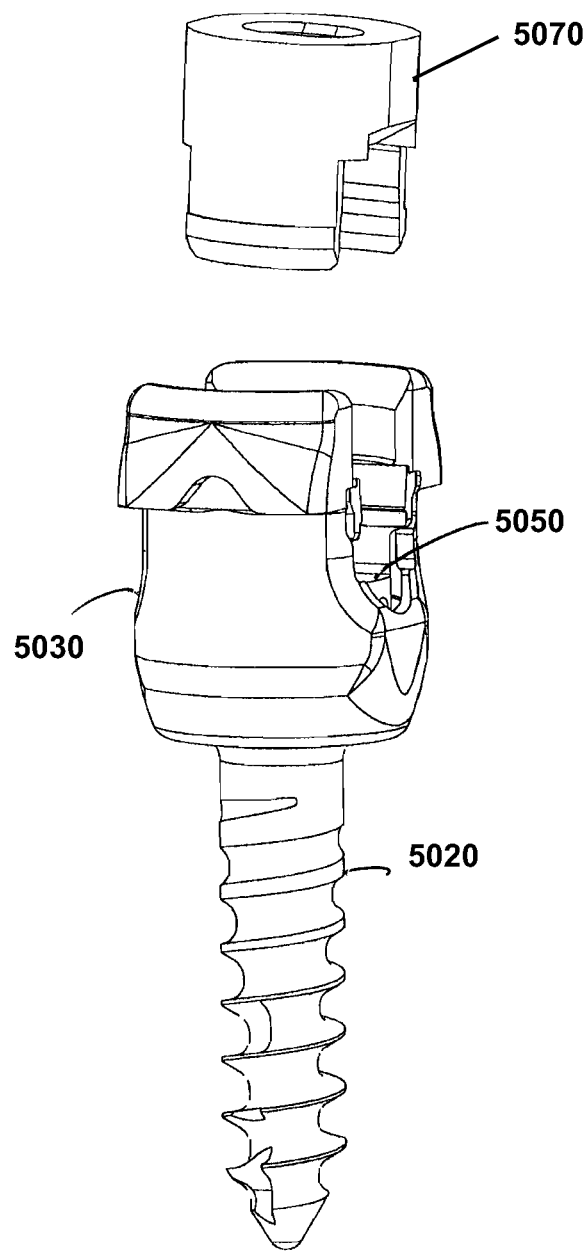
FIG. 41 is a perspective view of the coupling assembly of FIG. 38 with the cap removed.

The assembly of FIGS. 38-40 is shown from the exterior in perspective in FIG. 41. The shoulders of the yoke contain features to be engaged by an instrument for locking or manipulating the assembly. The outer surface of the outer yoke 5030 is curved toward the bottom to reduce the overall profile of the assembly.

FIG. 34 provides an exploded view of the pedicle screw system of FIG. 33, showing this embodiment of the pedicle screw assembly 4010 in a disassembled state. In this view, details of the individual components of the assembly may be more clearly viewed. Cap member 4070 includes a generally Cylindrical or disk-like top portion 4077 having legs 4071 extending downward from the top portion. The cap is shown in more detail in FIGS. 37A-C. Unlike the previously described embodiment (FIG. 27), the cap 4070 does not have a lip near the top portion, reducing the force necessary for full insertion and removal of the cap. The insert member or core member 4050 of the embodiment shown in FIGS. 33-35 contains finger-like projections 4062 with a two-step structure, with step portions 4057 and 4056 for interacting with the interior of the yoke 4030. The core member 4050 is shown in more detail in FIG. 36. In order to lock the anchor member 4020 in position, the step portions 4056 and 4057 are shifted into alignment with locking features 4059 and 4060, respectively.

As shown in FIG. 35, the offset angle anchor member 4020 may be mounted to bone 4001 at an angle and still permit a normal range of motion equivalent to that of a straight anchor member mounted substantially perpendicular to the bone. The anchor member 4020 and its head portion 4025 are designed so that when the anchor is mounted at a specific angle, the head still allows pivoting of the coupling assembly 4010 of Ø in any direction with respect to an axis normal to the surface of the bone 4001 in which the anchor is mounted. The coupling assembly 4010 depicted in FIG. 35 would not be allowed to pivot forward to the extent shown if the anchor head 4025 were mounted along the axis of the anchor's shank 4021.

Exemplary Screw Inserter Tools for Use with Offset Angle Screws

Figure 42:
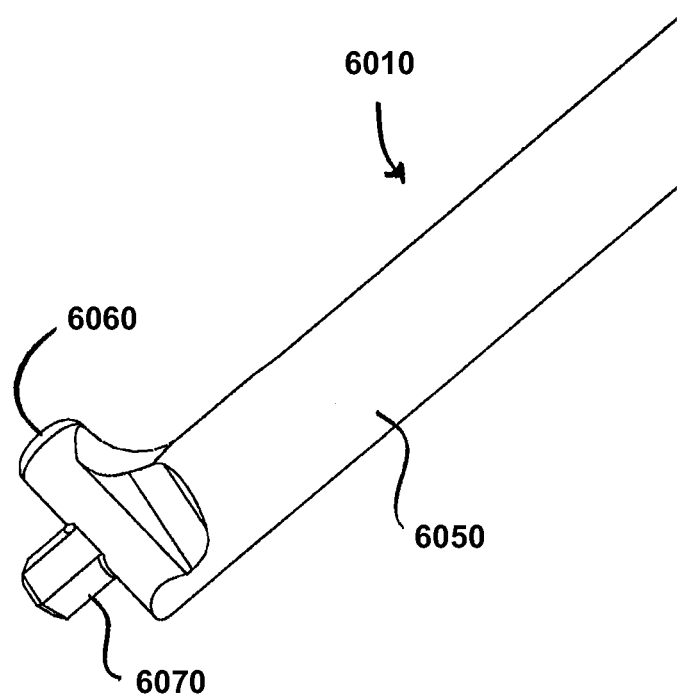
FIG. 42 is an elevational view of a screw inserter tool with an offset interface portion for engaging the offset head portion of the anchor member of FIGS. 28A and 28B.
Figure 43:
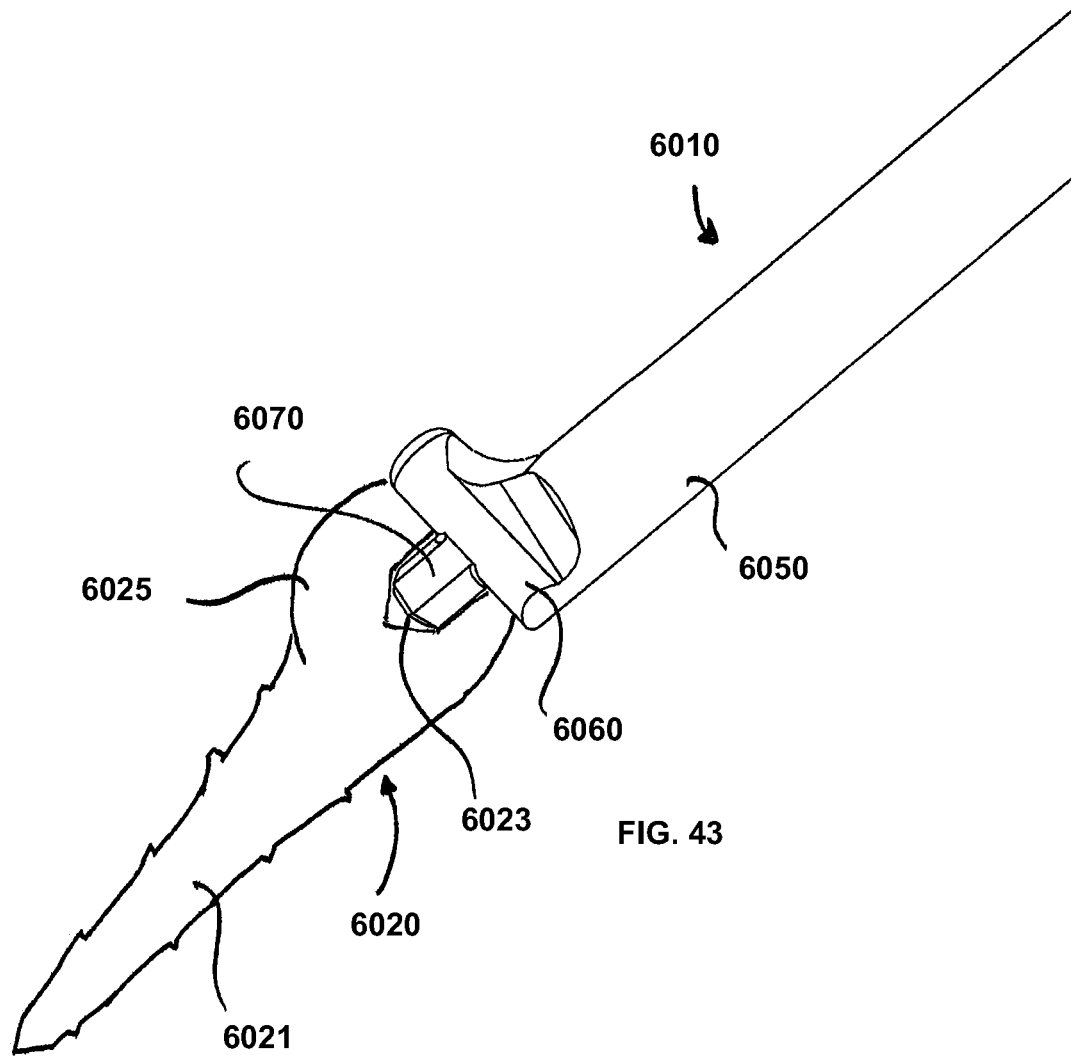
FIG. 43 is an elevational view of the screw inserter of FIG. 42 interfacing with the offset screw head.
Figure 44A:
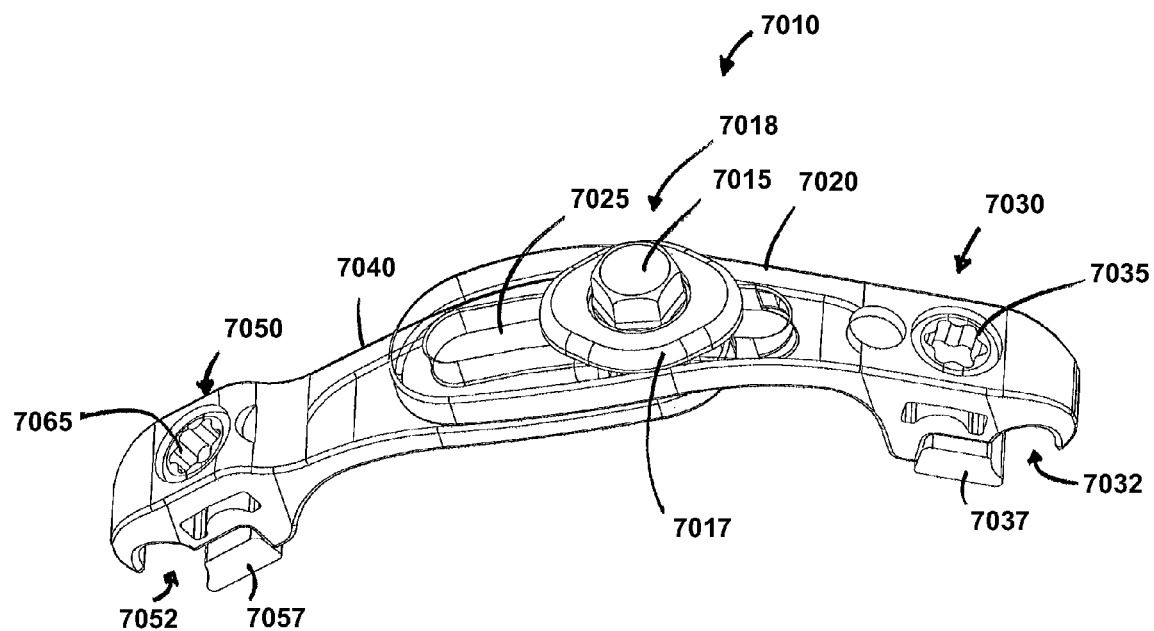
FIGS. 44A and 44B are perspective and exploded views, respectively, of a transverse connector device.
Figure 44B:
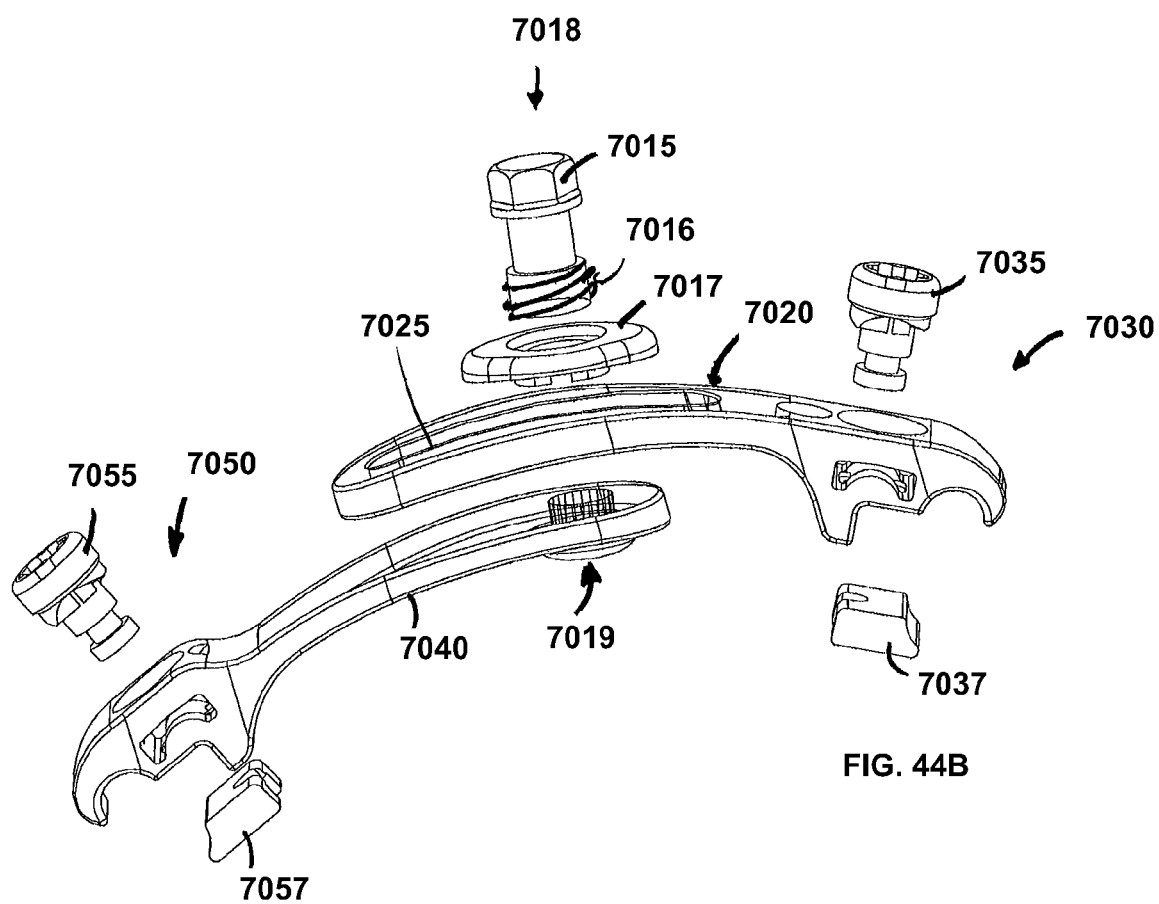

FIGS. 42-43 depict a screw inserter and driver for use with an offset angle screw as described above. The illustrated inserter 6010 has a shaft 6050 and an interface drive portion or projection 6070 for interfacing with the drive socket 6023 of the offset head portion 6025 of a pedicle screw 6020 (or, for instance, the drive socket 3023 of the offset head portion 3025 of a pedicle screw 3020 of FIG. 28B). The drive projection 6070 is not aligned with the axis of the shaft 6050. As shown in FIG. 43, since the drive projection 6070 is not aligned with the central axis of the shaft portion 6050 of the tool, it may be used to interface with the head 6025 of the offset pedicle screw 6020 so that the threaded shank 6021 of the screw is aligned along the shaft axis of the inserter tool. In other words, since both the tool drive projection 6070 and the screw head 6025 are out of alignment and offset from their associated axial portions by an equal and offset amount, aligning the tool's drive projection 6070 with the recess 6023 in the screw head 6025 aligns the tool shaft 6050 with the screw shank 6021 just as a normal, straight screw shank is aligned with the shaft of a normal insertion tool. Therefore, rotation of the tool shaft 6050 rotates the drive projection 6070 received in the screw head socket 6023 and the offset screw head 6025 orbitally around the screw shank 6021 so that the screw shank 6021 is rotated about its axis in order to threadingly drive the shank into bone. In order to facilitate connection between the inserter tool 6010 and the screw head 6025 with such an offset configuration, the tool's drive projection 6070 and the recess 6023 in the screw head 6025 may be configured to only fit together in one orientation.

The screw inserter 6010 may also include a core lock member 6060 configured much like a spinal rod and positioned to extend transversely to the tool shaft 6050. The core lock member 6060 imitates a spinal rod and may be used to capture a core member or insert of a pedicle screw system, such as the type described above, to insert a screw into bone when the screw is already coupled to the core member. The core lock member 6060 is disposed within the rod channel of the core member (e.g. 3065 of FIG. 30A) and the drive protrusion 6070 is disposed in the drive socket 6023 of the offset head portion 6025 held within the core member 3065 so that both the core member 3065 and the screw 6020 are rotated by rotation of the tool. Due to the offset nature of the screw head 6025, the core member 3065 will rotate orbitally around the axis of the screw shank and the axis of the tool shaft 6050.

Other inserter tools and variations of the described embodiment may also be used. The interface portion 6070 may, for instance, be aligned along the tool axis 6050, or the core lock member 6060 may be removed. Traditional inserters may also be used, but are not preferred.

Exemplary Transverse Connection Devices

When a series of pedicles screws are used to mount two or more rods to a patient's spine, a transverse connector or cross connector may be used to link two spinal rods. An exemplary transverse connector is shown in FIGS. 44A-47. The transverse connector 7010 includes a first arm 7020 having a first head 7030 for receiving a first spinal rod, and a second arm 7040 having a second head 7050 for receiving a second spinal rod. The first head 7030 has a cam actuator member 7035 that when rotated shifts a clamp member or jaw member 7037 upward to clamp a spinal rod in place within the rod seat 7032 in the first head. Likewise, the second head 7050 has a cam actuator member 7055 that shifts a clamp member or jaw 7057 upward to clamp a spinal rod in place within the rod seat 7052 in the second head. Advantageously, the cam members are each generally cylindrical with an axis therethrough, and have non-threaded contoured surfaces that cause them to shift axially in the head portions when rotated so that the clamp members 7057 and 7037 move from fully open to fully clamped when the cam members 7055 and 7035 are rotated less than 360°. However, alternatively other actuator members may be used in place of the illustrated cam members 7035 and 7055. For instance, threaded screws may be used to shift clamp members 7057 and 7037, with the threading on the screws configured to match complementary threading on the interior of the head portions 7030 and 7050.

Figure 45:
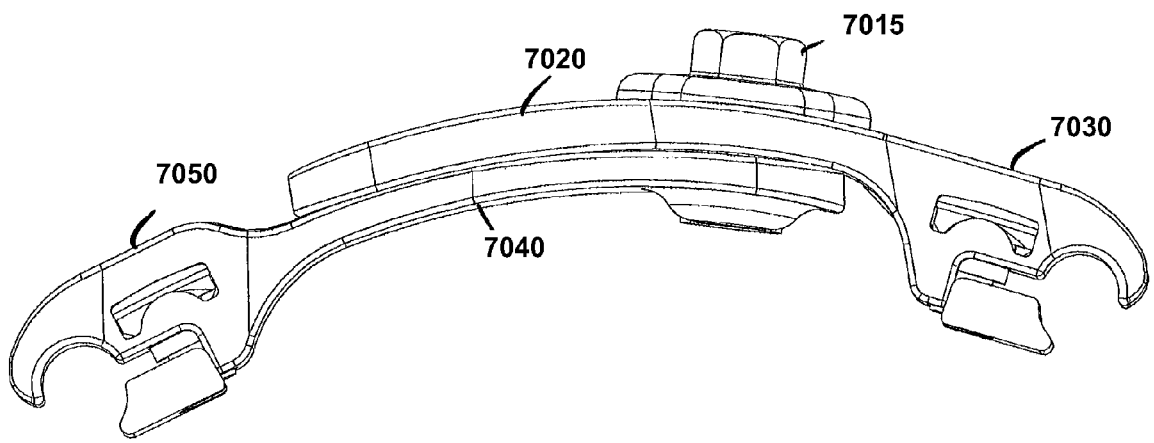
FIG. 45 is a front plan view of a transverse connector device.
Figure 46:
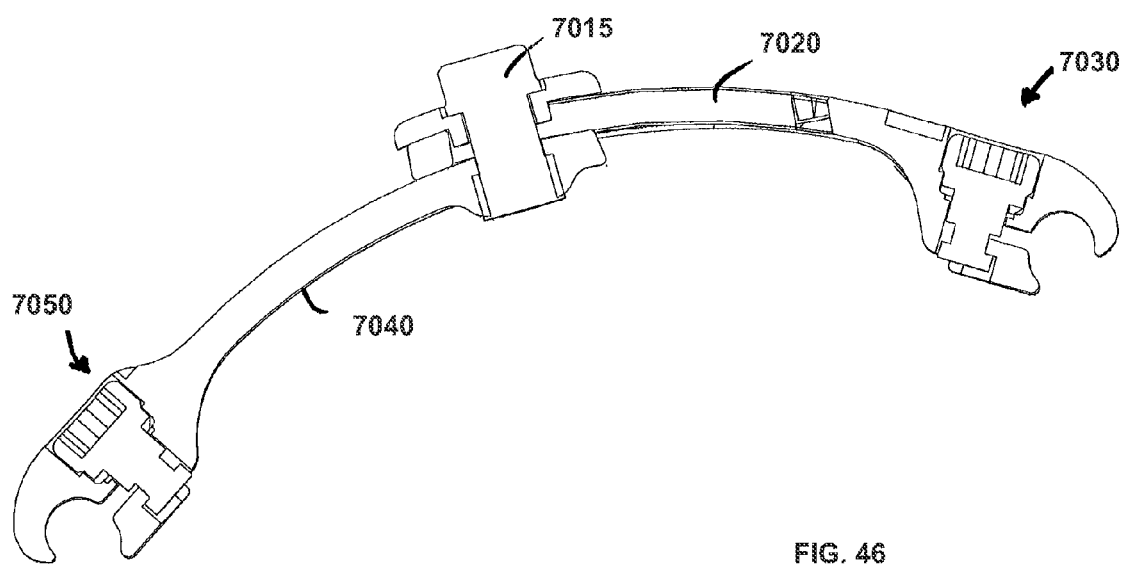
FIGS. 46-47 are front cross-sectional views of a transverse connector device in a compact configuration and an extended configuration, respectively.
Figure 47:
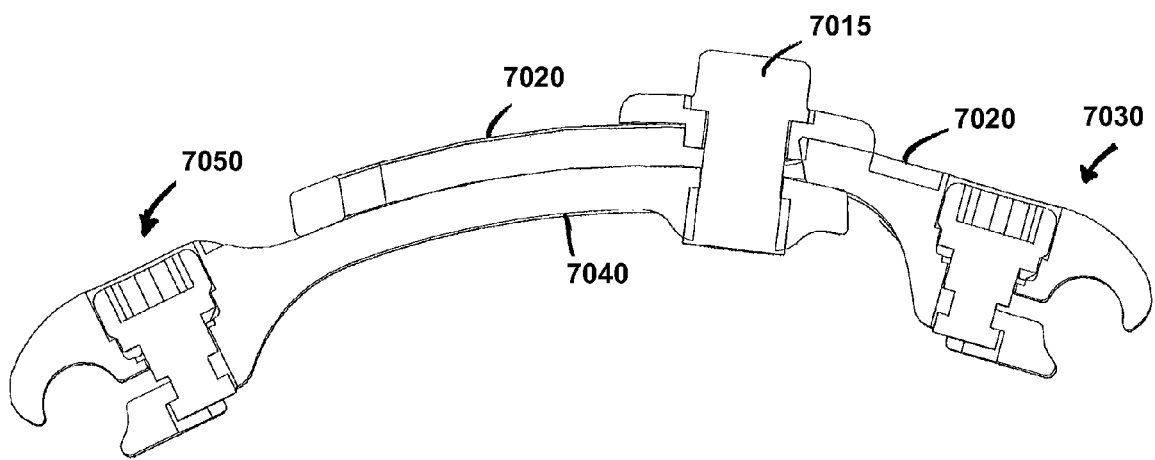

The two arms 7020 and 7040 of the transverse connector 7010 are positioned relative to one another using an adjustment device. The illustrated adjustment device 7018 has a head portion 7015 that may be turned to lock and unlock the arms. The head portion 7015 is connected to a threaded portion 7016 that is threaded into a threaded orifice 7019 in the second arm 7040. Rotating the head portion 7015 and associated threaded portion 7017 clamps the arms 7020 and 7040 together, preventing relative movement of the two arms. A washer member 7017 is provided to facilitate clamping of the arms and to prevent accidental unlocking. When the adjustment device 7018 is unlocked, the arms may be shifted linearly to increase or decrease the width of the device. During linear adjustment, the adjustment device 7018 moves back and forth through a slot 7025 in the first arm 7020. FIG. 45 shows the transverse connector in a compact configuration, where the arms 7020 and 7040 almost completely overlap. FIG. 46, in contrast, shows an extended configuration wherein there is minimal overlap between the two arms. In addition to linear adjustment, the arms 7020 and 7040 may be pivoted with respect to one another so that the heads 7030 and 7050 may capture non-parallel portions of spinal rods. The arms 7020 and 7040 pivot about the adjustment device 7018 when it is in the unlocked configuration. Upon turning of the adjustment device 7018, the arms are clamped together, preventing both sliding and pivoting of the arms. Thus, the single adjustment device is sufficient to lock the transverse connector against further linear and angular adjustment. Although shown as a threaded member, the adjustment device 7018 may incorporate a cam actuator similar to those in the head portions or other such devices to clamp the arms of the connector together.

In the illustrated embodiment, the arms 7020 and 7040 are relatively flat in order to substantially reduce the profile of the transverse connector. In addition, both arms 7020 and 7040 are arched, in order to provide clearance underneath the cross-connector. This allows the transverse connector to connect spinal rods across bony protrusions or other tissue without interfering with such tissues or requiring their removal.

Exemplary Reducer/Inserter Instrument

A reducer/inserter tool may also be provided for reducing a spinal rod into a coupling device and inserting a cap member to lock the position of the rod. One exemplary reducer/inserter tool is shown in FIGS. 48-52. One advantage of the reducer inserter tool is the ability to quickly and efficiently provide rod reduction and cap locking in one tool. Another advantage of the present reducer inserter tool is the simplicity in design and operation. The reducer inserter tool operates through manipulation of a lever 10321 configured to actuate a reducing mechanism and a handle 10413 to actuate a cap driving mechanism. The simple operation simplifies manufacturing, reduces training, and improves reliability of the reducer inserter tool.

Finally, another advantage present in the reducer inserter tool is the low weight of the reducer inserter tool. The reducer inserter tool may be made from materials such as titanium, Nitinol, stainless steel alloys, or combinations thereof, and the amounts of those materials may be minimized to reduce weight of the tool. The manufacture and material composition of the tool is not readily apparent to the user but functions to reduce surgeon fatigue after repeated operations of the tool and to reduce the risk of injury to the patient. The risk of injury to the patient is minimized because the light weight of the tool prevents excessive momentum and force from building as the tool moves from one location on the spine to another. Should the tool impact the spine the reduced weight of the tool reduces the corresponding impact on the spine and attached spinal cord.

The reducer/inserter tool 10001 shown in FIGS. 48-54 secures a spinal rod in a coupling device of the type described in connection with FIGS. 1-41. The tool 10001 reduces the spinal rod into the device and then inserts a cap or other lock member into the device to lock the rod in place. In one form, the assembly manipulated by the reducer/inserter tool 10001 has an insert member that couples to a screw and a rod, an outer member that shifts in a first direction over the insert to lock the screw in place, and a cap member that is inserted between the insert and outer members in a second direction opposite the first direction to lock the position of the rod. The reducer inserter tool contains structures to shift the outer member and cap member relative to the insert member to secure the rod and lock the screw in the assembly to prevent pivoting therebetween.

Figure 48A:
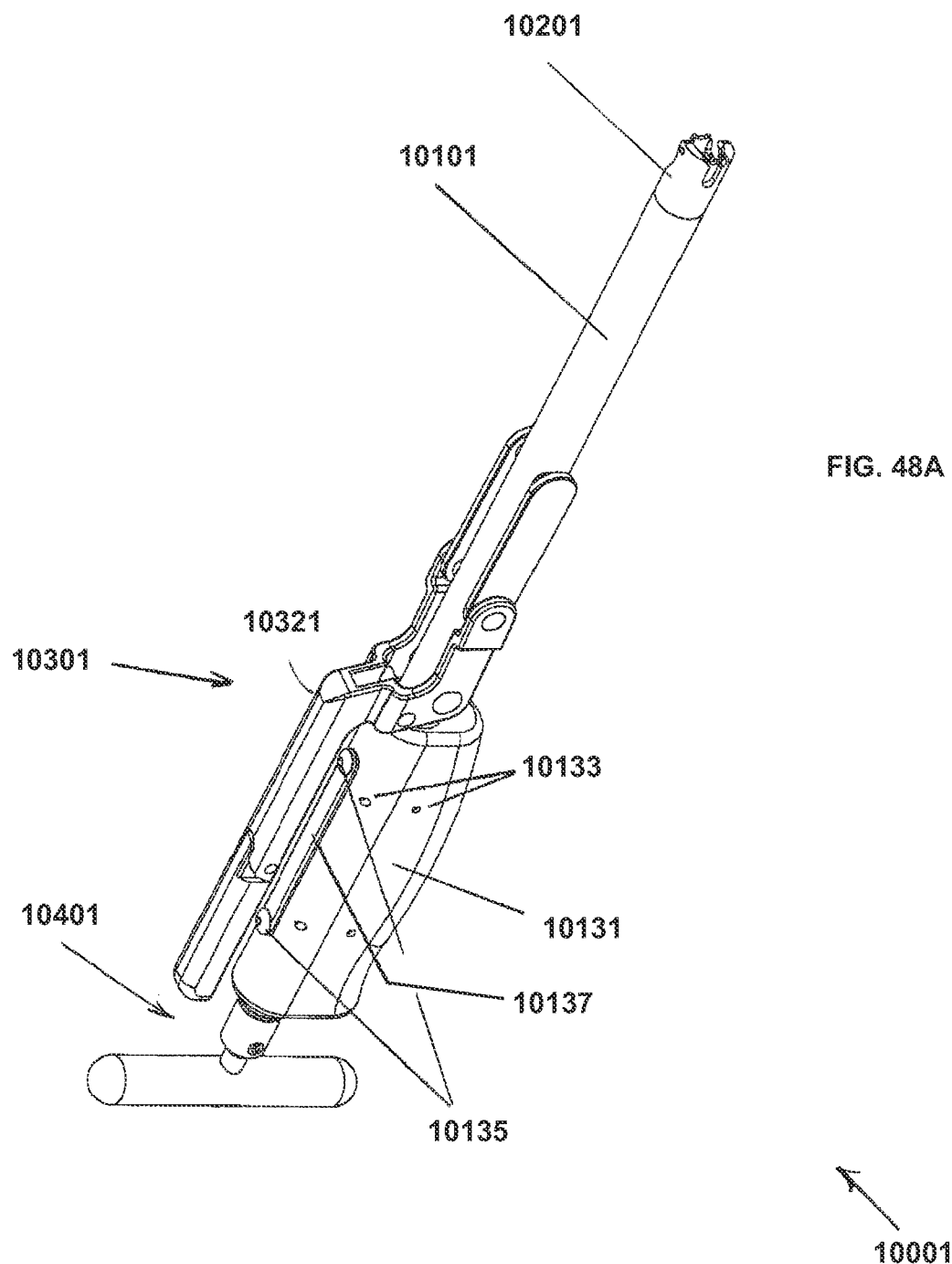
FIGS. 48A-B are perspective views of a reducer/inserter tool for locking a coupling device.
Figure 48B:
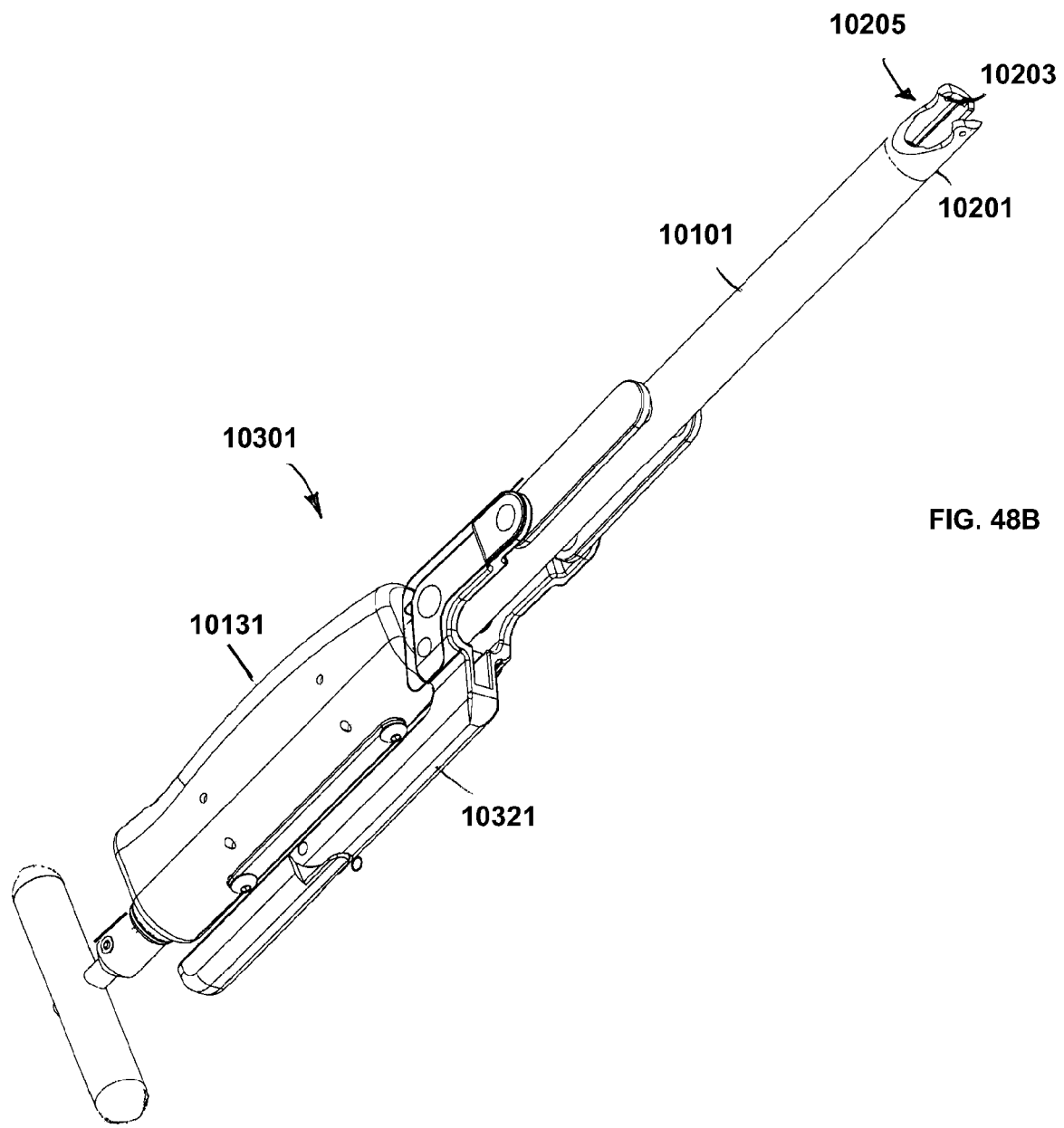

The reducer/inserter tool includes an outer shaft portion 10101 that has a distal head portion 10201 as shown in FIG. 48 for grasping the outer member of the coupling device. As shown in FIG. 48B, the outer shaft head portion has an access port 10205 that receives the coupling device from a side of the tool. The head portion 10201 is open at the end to allow the anchor member of the coupling device to pass therethrough when the coupling device is received in the head portion 10201. The coupling device is received through a side access port 10205 so that the enlarged shoulder portion of the coupling device outer member (or a similar structure designed to be grasped by a tool) may slide above projections 10203 on the interior of the outer member. The projections 10203 prevent the coupling device from being pushed out through the opening in the bottom of the head portion 10201 when downward force is applied by the tool to reduce the spinal rod into the coupling device.

Figure 51A:
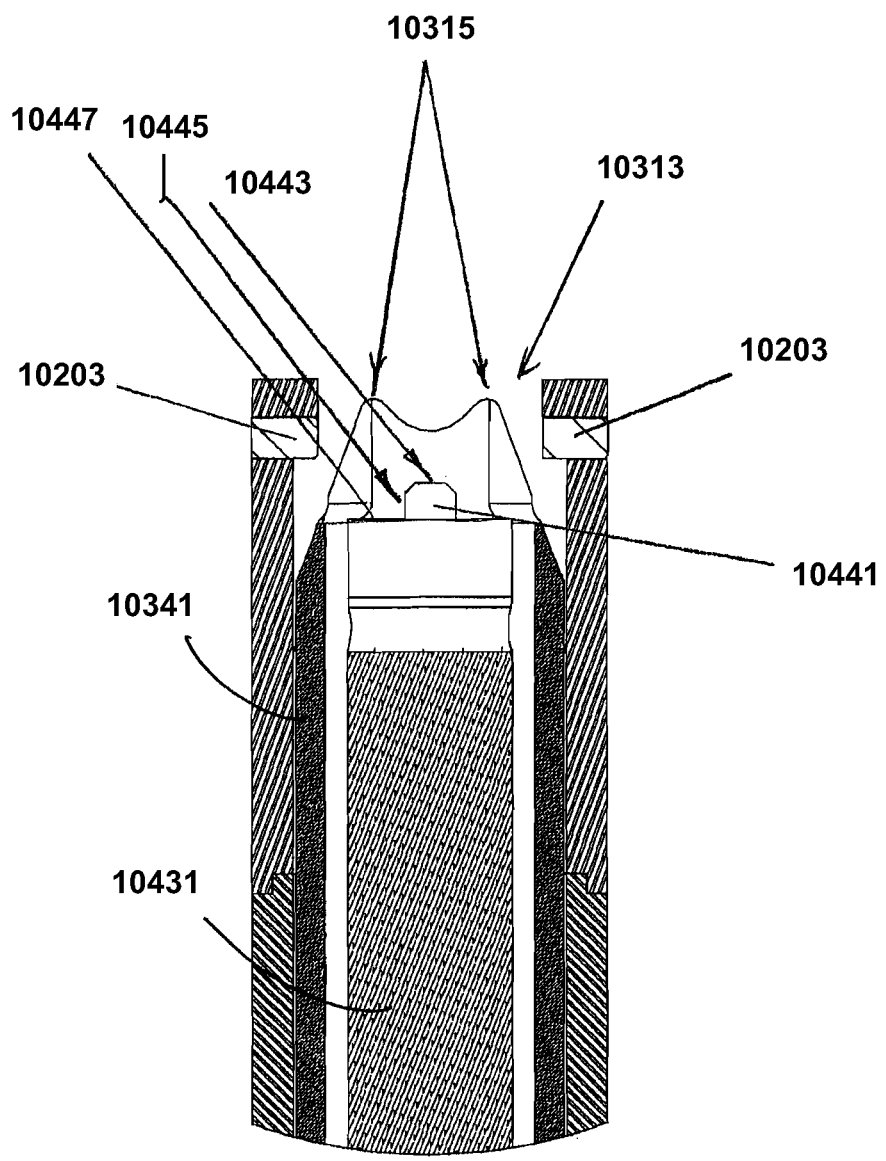
FIG. 51A-B are detailed cross-sectional views of the head portion of the reducer inserter tool.
Figure 51B:
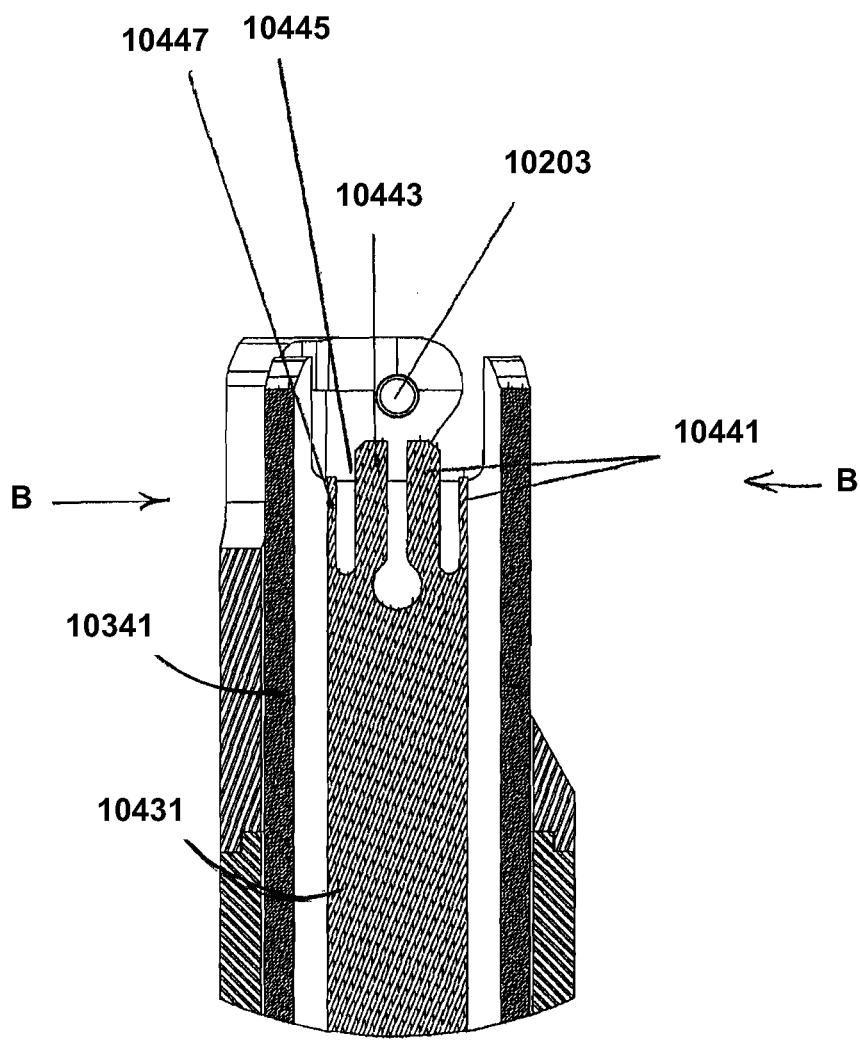
Figure 52:
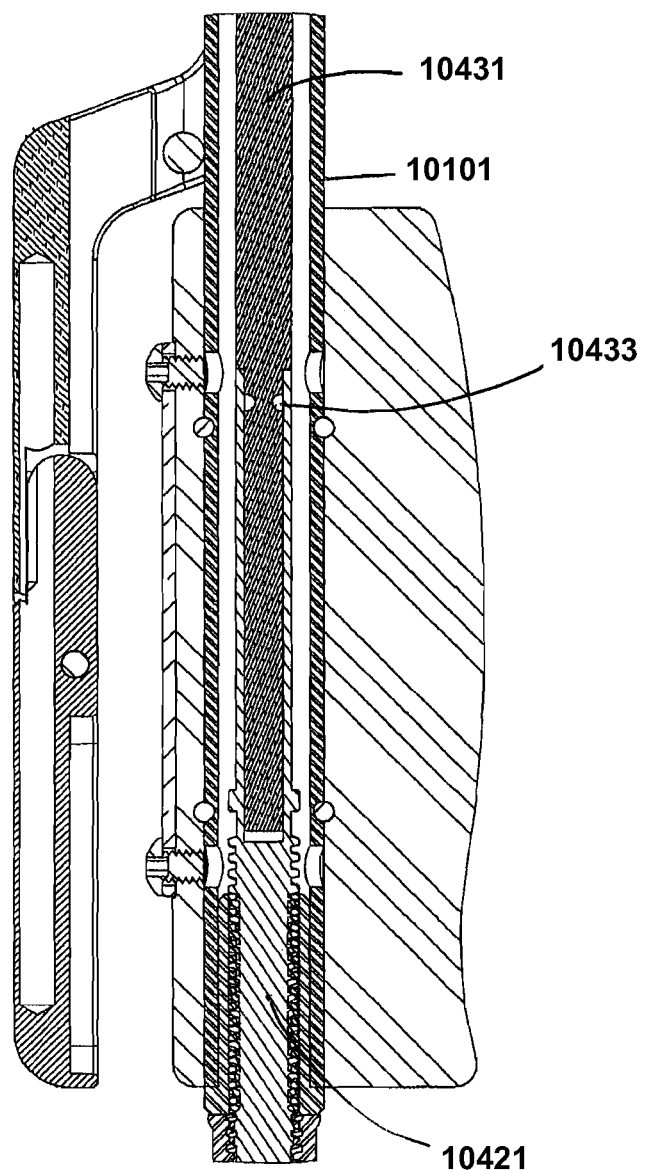
FIG. 52 is a detailed cross-sectional view of the cap driving mechanism of the reducer/inserter tool.

The head portion is shown in greater detail in FIGS. 51A and 51B. Projections 10203 on the interior of the head portion 10201 allow the head portion 10201 to grasp the coupling device from the underside of a shoulder portion or other surface feature (for example, shoulder recess 3033 in FIG. 26). When the coupling device is under compressive loading during the reduction of the rod into the insert member, then the shoulder recess 3033 in the underside of the shoulder of the screw assembly will self-center the projection 10203.

As shown in FIGS. 48A-B, the outer shaft portion 10101 is coupled to a handle 10131 to allow the surgeon to grasp the tool 10001. As illustrated in FIGS. 48A-B, the handle 10131 is connected to the exterior of the outer shaft 10101 by pins 10133, screws 10135, and a plate 10137, although other methods may alternatively be used.

Figure 49:
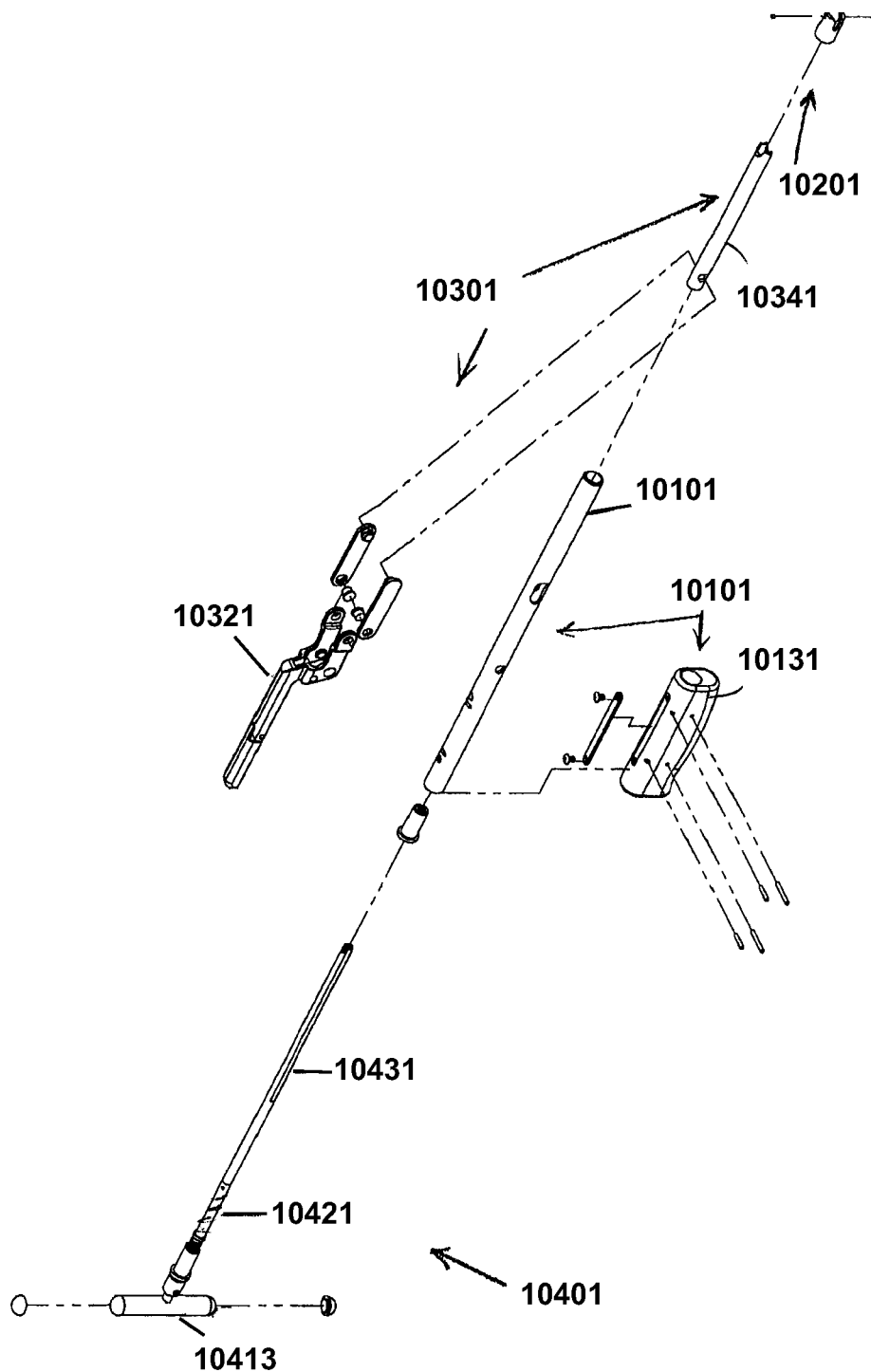
FIG. 49 is an exploded perspective view of the reducer/inserter tool.

Rod reduction is accomplished by manipulation of the reducing lever 10321. As shown in FIG. 49, the hollow reducing shaft 10341 is disposed concentrically within the outer shaft 10101 and connected to the reducing lever 10321 via a linkage. The linkage connects the lever 10321 to the reducing shaft 10341 through elongate openings in the outer shaft 10101 so that pivoting of the lever 10321 causes axial shifting of the reducing shaft 10341 within the outer shaft 10101. The tip of the reducing shaft is configured to interface with the exterior of a spinal rod, so that linear shifting of the reducer shaft 10341 is capable of driving the spinal rod into the coupling member with significant force.

After rod reduction, locking of the cap within the coupling device is achieved by turning of a T-bar handle 10413. A threaded drive portion 10421 is connected to the handle 10413 and configured to mate with threading on the interior of the outer shaft 10101 so that turning of the handle causes advancement of the drive mechanism 10421 through the interior of the outer shaft 10101. A drive shaft 10431 is rotatable coupled to the threaded drive portion 10421 so that advancement of the drive portion by turning of the handle linearly advances the drive shaft 10431 without rotation. The end of the drive shaft 10431 is configured to receive a cap member and drive the cap member into contact with a coupling member received in the head portion 10201 of the tool. The above structures are shown in an assembled state in FIG. 50.

Figure 50:
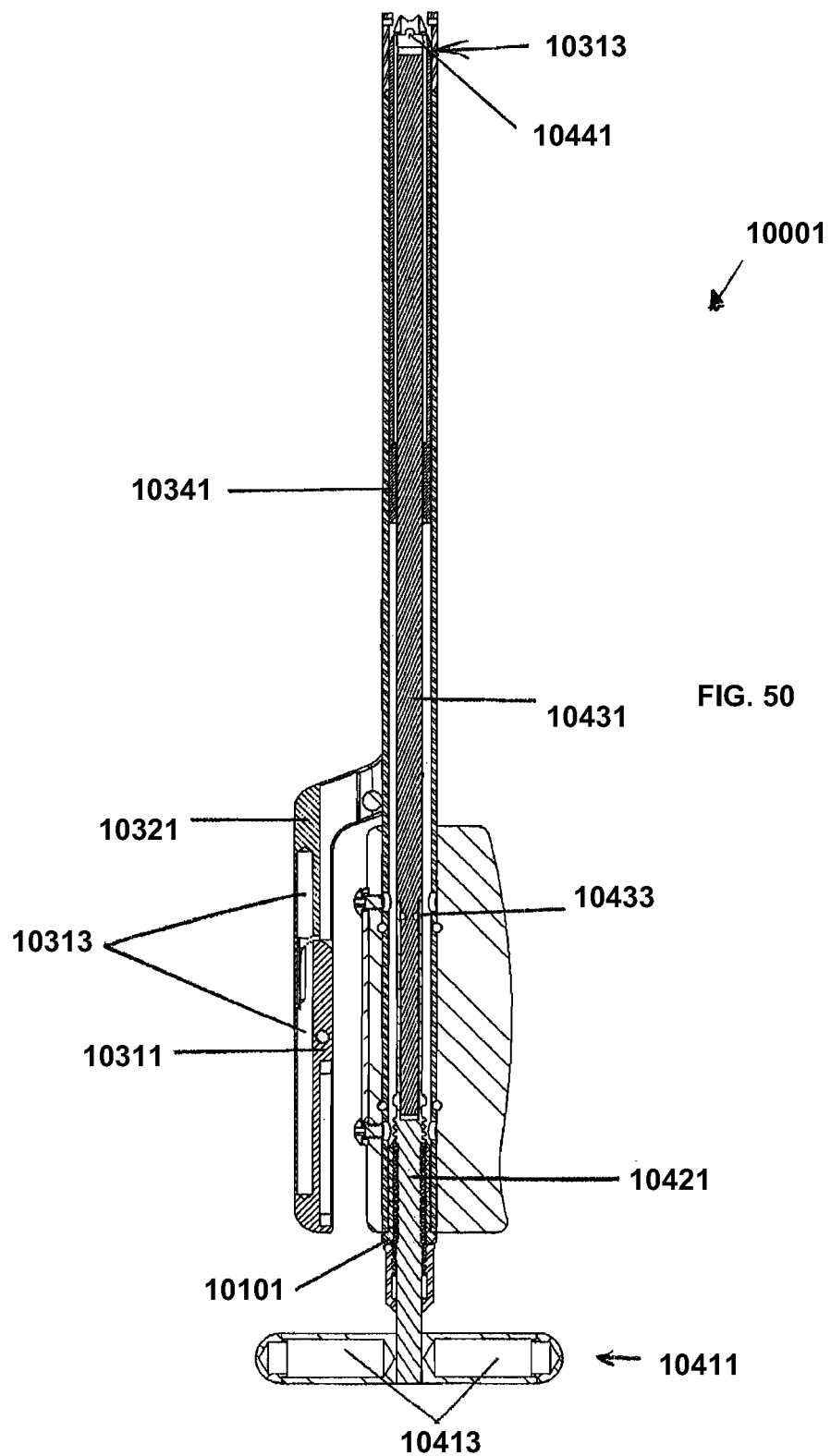
FIG. 50 is a cross-sectional view of the reducer/inserter tool.

The reducing mechanism 10301 of the tool is shown in greater detail in the cross-sectional view of FIGS. 50 and 51. FIG. 50 illustrates the main components of the reducing mechanism: the access lever 10311, the reducer lever 10321, and the reducing shaft 10341. The reducer assembly mechanically operates kinematically as a four-bar linkage to shift the reducing shaft 10341 in order to advance the rod into the screw assembly.

The lever 10321 mechanically locks or bottoms out to prevent the pitching or crushing injury to the hand of the operator. The lever 10321 is mounted to the outer shaft 10101 via a pivot pin which allows the lever 10321 to pivot on the outer shaft 10101. The lever 10321 provides the operator with a mechanical advantage multiplied by the linkage 10331 to linearly drive the reducing shaft 10341. The linkage 10331 is connected to the reducing shaft 10341 by a pin 10323 to allow motion and force to be transmitted from the lever 10321 to the reducing shaft 10341 in a linear fashion, i.e. back and forth in a proximal or distal direction.

The operator of the reducer inserter tool 10001 is able to place their fingers underneath the lever 10321 through the operation of the access lever 10311. The access lever 10311 deflects out of position to allow the operator access to operate the lever 10321. The access lever 10311 may be provided with Nitinol springs or rods placed within the spring recesses 10313 in order to assist in resilient deflection of the access lever.

The reducing shaft 10341 interfaces with the rod at the distal shaft tip 10313 shown in FIGS. 50, 51A, and 51B. The reducing shaft 10341 has a bearing surface 10315 that interfaces and contacts the spinal rod. The bearing surface may be contoured to match the exterior surface of the rod. The rod is forced into position because the projections 10203 of the tool's head portion hold the yoke of the screw assembly while the bearing surface 10315 forces the rod into position.

The cap driving mechanism 10401 of the tool consists of four main components shown in FIG. 50: the driver handle portion 10411, the threaded portion 10421, the shaft portion 10431, and the coupling 10441.

The handle portion 10411 is the only visible portion of the cap driving mechanism 10401 when the tool 10001 is assembled. The handle portion 10411 may have hollowed out recesses 10413 in order to reduce weight of the tool 10001. Weight of the tool may be kept to a minimum to reduce inertia and the risk of impact force from the tool contacting the cervical region of the spine.

A threaded portion 10421 of the cap driving mechanism connects to the handle portion 10411 and is complementary to threading on the outer shaft member so that rotation of the handle and threaded portion advances the cap driving mechanism toward the head of the tool. The threaded portion 10421 may have, for instance, double lead acme threading that interfaces with the outer shaft 10101 to act as a threaded drive for the tool 10001. Double lead threading allows for quick action of the drive member 10401, i.e. reduced rotation of the handle 10411 is required for linear driving of the cap into the screw assembly. The acme threading allows for extremely high loadings to be applied to the threaded drive member 10401 yet allows for smooth and reliable operation.

An inner shaft portion 10431 for driving a cap member into a coupling device received in the tool head portion 10201 may be rotatably mounted to the threaded portion 10421. In one form, the threaded portion and shaft portion may be rotatably coupled by a pin 10433 attached to the threaded portion and received in an annular channel in the exterior of the drive shaft. The pin 10433 transmits the linear motion of the threaded portion 10421 to the shaft portion 10431. The shaft portion 10431 then translates within the outer shaft 10101 and the reducing shaft 10341 without rotation. These structures are shown in greater detail in FIG. 52.

A coupling may be provided on the inner shaft 10431 to hold a cap member of the coupling device thereto. The type of coupling will, of course, depend upon the type of cap member to be used. A coupling 10441 for connection to a cap of the type shown in FIG. 27 (cap member 3070) or in FIG. 38 (cap member 5070) is located at the most distal end of the shaft portion 10431 as shown in FIGS. 51A-B. The coupling 10441 provides a non-rotatable connection to the cap of the screw assembly. The coupling 10441 includes a snap fit post 10443, a cap bearing surface 10445, and a drive post 10447.

The snap fit posts 10443 will deflect inward and act as a cantilever spring to allow a snap fit connection to the central opening of a cap of the screw assembly. The pressure of the bearing surface 10445 on the cap created by the cantilever spring action of the snap fit post 10443 keeps the cap secured to the coupling 10441. Optionally, the cap can be securely attached by the operator driving the cap into the coupling 10441 with the assistance of a cap caddy (not shown). The cap locks into place and is supported by the drive post 10447 during the final locking of the cap into the insert member. The cap may be properly oriented during the final locking of the cap to the insert member by providing the snap fit post 10443 with an elliptical shape matching an elliptical opening in the center of the cap member.

When the handle 10411 is rotated and the cap is driven into the insert member of the screw assembly, the coupling 10441 will maintain position of the cap. The drive post 10447 then applies a compressive force to the head of the cap to lock the cap into the insert member. The locking force of the insert member on the cap then secures the cap allowing the cap to disengage the snap fit post 10443 when the drive member 10401 is driven in the proximal direction.

The reducer inserter tool 10001 can be manufactured by standard turning, milling, and Electro Discharge Machining (EDM). The reducer inserter tool 10001 can be made from any suitable, structurally strong materials. The reducer inserter tool 10001 can be constructed of suitable materials which are compatible with the uses and environments into which the device will be utilized. Preferably, the reducer inserter tool 10001 is constructed of metallic materials such as stainless steel or titanium. The reducer inserter tool 10001 may be sterilized through a number of methods, including the use of an autoclave, i.e. steam.

Once the screw assembly has been surgically implanted on the chosen vertebrae, then the spinal rod and cap are added with the assistance of the reducer inserter tool 10001. Typically, the drive member 10401 will be extended to its furthest distal position by rotating the handle 10411 in a clockwise manner. The reducer inserter tool 10001 may optionally be driven into a cap in a cap caddy (not shown) to lock the cap to the coupling 10441. The handle 10411 will typically then be rotated in a counter-clockwise manner to move the coupling 10441 and the cap in a proximal direction to keep the cap from mechanically interfering with the reduction of the rod on the insert member.

The reduction process begins with placing the spinal rod within the screw assembly. The rod may, for instance, snap temporarily into place for temporary positioning. The screw assembly and rod are then captured in the head of the reducer inserter. The lever 10321 will be pivoted to cause the reducer assembly 10301 to move to the proximal direction out of the way for further operation of the tool 10001. The head of the reducer inserter tool 10001 will then be placed around the screw assembly and spinal rod, shifting the coupling assembly into the access port 10205 at the distal tip of the reducer inserter tool 10001. The reducer lever 10321 will then be pivoted toward the handle of the instrument to cause the reducer shaft 10341 to shift toward the distal direction to force the spinal rod into the screw assembly. The lever 10321 will lock into position to secure the rod into its final position within the insert member of the screw assembly. In the types of coupling devices shown in FIGS. 1-41, the reducer assembly may also shift the insert core member with respect to the outer member held by the tool, thus locking the anchor member in place during the rod reduction process.

Since the reducer shaft is hollow, a cap member for locking the coupling assembly may be inserted therethrough while the reducer shaft holds the rod in place within the coupling assembly. To insert the cap member, the handle 10411 will be rotated, typically in a clockwise manner, to move the coupling 10441 and the cap in the distal direction. The handle 10411 is rotated until the drive member can no longer be rotated and thus fully inserting the cap into the insert member. The cap will then be locked into the insert member. The cap drive handle 10411 will then be rotated in a counter-clockwise manner to disengage the coupling 10441 from the cap. The lever is then pivoted to disengage the reducer assembly 10301. The entire assembled coupling device is freed from the distal tip of the reducer inserter tool 10001 by moving the tool sideways so that the coupling device exists through the access port 10205 to complete the rod reduction and cap insertion process.

Each of the above embodiments are only examples of the present inventions, and the present inventions are not restricted to the above embodiments.

What is claimed is:

1. A pedicle screw assembly for securing a spinal rod to a vertebral bone, the pedicle screw assembly comprising:
   a coupling device configured for receiving a spinal rod seated therein and having a central axis with the spinal rod extending generally orthogonal to the central axis when seated in the coupling device;
   a through passageway of the coupling device extending along the coupling device central axis;
   an elongate screw anchor member having proximal and distal ends, an elongate threaded shank portion configured for being rotated to be anchored to a vertebral bone, a central longitudinal axis extending along the elongate threaded shank portion and about which the elongate threaded shank portion is rotatable for being driven into a vertebral bone, and an enlarged, generally spherical head portion at the screw anchor member proximal end and having a center;
   a bottom opening of the coupling device through passageway;
   an engagement surface of the coupling device for engaging the screw anchor member head portion with the screw anchor member extending out of the bottom opening for anchoring the elongate threaded shank portion thereof to a vertebral bone; and a non-threaded neck portion of the elongate screw anchor member connected to the enlarged head portion and the elongate shank portion to extend therebetween and having a central axis extending therealong obliquely to the threaded shank portion central longitudinal axis so that the enlarged head portion is proximally spaced from the elongate threaded shank portion and the center thereof is offset from the shank portion central longitudinal axis to allow the coupling device to be pivoted toward the elongate shank portion by a greater amount in one direction than in an opposite direction and to allow for 360° relative rotation between the coupling device and the screw anchor member head portion so that the greater amount of pivoting between the coupling device and the elongate shank portion in the one direction is accessible by relative rotation, if necessary, between the coupling device and the screw anchor member head portion, wherein the generally spherical enlarged head portion of the elongate screw anchor member has a truncated upper portion in which a drive recess is formed and has an axis extending centrally through the drive recess and the enlarged head portion center that is offset and generally parallel to the threaded shank portion longitudinal axis due to the obliquely extending neck portion therebetween, and wherein the generally spherical enlarged head portion of the screw anchor member has one spherical surface portion along one side thereof that extends to and between the truncated upper portion and the anchor member neck portion in a proximal-to-distal direction down along the one side of the generally spherical enlarged head portion for a longer distance than a diametrically opposite spherical surface portion along a diametrically opposite side of the generally spherical enlarged head portion with the opposite spherical surface portion extending to and between the truncated upper portion and the anchor member neck portion in the proximal-to-distal direction down along the opposite side of the generally spherical enlarged head portion.

2. The pedicle screw assembly of claim 1 wherein the coupling device has a lower edge extending about the through passageway bottom opening, and the greater amount of pivoting of the coupling device in the one direction comprises 60 degrees of pivoting of the coupling device relative to the threaded shank portion until abutment of the anchor member neck portion with the coupling device lower edge occurs.

3. The pedicle screw assembly of claim 1 wherein the one spherical surface portion has a juncture with the neck portion, the coupling device has a lower edge extending about the through passageway bottom opening, and the increased pivoting of the coupling device toward the threaded shank portion in the one direction occurs until the coupling device lower edge abuts the juncture between the one spherical surface portion and the neck portion.

4. The pedicle screw assembly of claim 1 wherein the coupling device comprises an outer yoke member and an insert member configured to be received in the outer yoke member and having a generally spherical cavity formed by the coupling device engagement surface.

\* \* \* \* \*